(12) United States Patent
Kinney et al.

(10) Patent No.: US 8,795,688 B2
(45) Date of Patent: *Aug. 5, 2014

(54) DENGUE SEROTYPE 2 ATTENUATED STRAIN

(75) Inventors: Richard Kinney, Fort Collins, CO (US); Claire Y. H. Kinney, Fort Collins, CO (US); Véronique Barban, Craponne (FR); Jean Lang, Mions (FR); Bruno Guy, Lyons (FR)

(73) Assignees: Sanofi Pasteur, Lyons (FR); Centers for Disease Control and Prevention, Atlanta, GA (US)

( * ) Notice: Subject to any disclaimer, the term of this patent is extended or adjusted under 35 U.S.C. 154(b) by 198 days.

This patent is subject to a terminal disclaimer.

(21) Appl. No.: 13/281,255

(22) Filed: Oct. 25, 2011

(65) Prior Publication Data

US 2012/0083585 A1    Apr. 5, 2012

Related U.S. Application Data

(60) Continuation of application No. 12/633,459, filed on Dec. 8, 2009, now Pat. No. 8,067,566, which is a division of application No. 11/453,344, filed on Jun. 15, 2006, now Pat. No. 7,641,908.

(60) Provisional application No. 60/691,274, filed on Jun. 17, 2005.

(51) Int. Cl.
*A61K 39/12*    (2006.01)
*C12N 7/00*    (2006.01)
*C12N 7/08*    (2006.01)

(52) U.S. Cl.
USPC .............. 424/218.1; 424/186.1; 435/235.1; 435/236; 435/237

(58) Field of Classification Search
None
See application file for complete search history.

(56) References Cited

U.S. PATENT DOCUMENTS 7,641,908 B2 * 1/2010 Kinney et al. .............. 424/218.1
2004/0137013 A1  7/2004 Katinger et al.

FOREIGN PATENT DOCUMENTS

| EP | 1159968 A1 | 12/2001 |
| WO | WO-9640933 A1 | 12/1996 |
| WO | WO-0057907 A2 | 10/2000 |
| WO | WO-02095075 A1 | 11/2002 |
| WO | WO-03092592 A2 | 11/2003 |

OTHER PUBLICATIONS

Butrapet et al., "Attenuation markers of a candidate dengue type 2 vaccine virus, strain 16681 (PDK-53), are defined by mutations in the 5' noncoding region and nonstructural proteins 1 and 3," *J Virol* 74(7):3011-3019 (2000).
Gowen et al., "Animal models of highly pathogenic RNA viral infections: hemorrhagic fever viruses," *Antiviral Res* 78(1):79-90 (2008).
Kinney et al., "Construction of infectious cDNA clones for dengue 2 virus: strain 16681 and its attenuated vaccine derivative, strain PDK-53," *Virology* 230(2):300-8 (1997).
Kinney et al., "Development of new vaccines against dengue fever and Japanese encephalitis," *Intervirology* 44(2-3):176-97 (2001).
Montagnon et al., "Experience with Vero cells at Pasteur Mérieux Connaught," *Dev Biol Stand* 98:137-40 (1999).
Putnak et al., "Development of a purified, inactivated, dengue-2 virus vaccine prototype in Vero cells: immunogenicity and protection in mice and rhesus monkeys," *J Infect Dis* 174(6):1176-84 (1996).
Sanchez et al., "Innate and adaptive cellular immunity in flavivirus-naive human recipients of a live-attenuated dengue serotype 3 vaccine produced in Vero cells (VDV3)," *Vaccine* 24(23):4914-26 (2006).

* cited by examiner

*Primary Examiner* — Stacy B. Chen
(74) *Attorney, Agent, or Firm* — Clark & Elbing LLP

(57) ABSTRACT

The invention relates to live attenuated VDV2 (VERO-Derived Vaccine Dengue serotype 2) strains which have been derived from the wild-type dengue-2 strain 16681 by passaging on PDK and Vero cells and nucleic acids thereof. The invention further relates to a vaccine composition which comprises a VDV2 strain.

7 Claims, 6 Drawing Sheets

| Den2-16681/6PDK50 | LAV-2 pre-master P0 |

| TV100 | Transfection on Vero cells FPr/6 transf D09 P1 |

| LST 003 LST007 | Amplifications P2 to P4 |

| Clone 71 Clone 72 Clone 73 | Plaque Purification 1 P5 |

| Clone 721 Clone 722 | Plaque Purification 2 P6 |

| Clone 722 | Amplification 1 P7 |

| TV 722 | Amplification 2 P8 |

| VDV2 | Adaptation passages P9 to P11 |

FIG.1

```
Vero Working Cell Bank                    VDV2 passage 9
         |                                      |
         | Cell cultivation            Virus inoculation on Vero cells
         |                             Virus cultivaton on Vero cells
         ▼                                      ▼
  Vero cells suspension                  VDV2 passage 10
         |                                      |
         └──────────────┬───────────────────────┘
                        ▼
                  Crude Harvest
                        |
                        ▼
                Clarified Harvest
                        |
                        ▼
               Concentrated Harves
                        |
                        ▼
                 VDV2 passage 11
                    monovalent
                        |
                        ▼
                Final Bulk Product
                    monovalent
                        |
                        ▼
                  Filled Product
                    monovalent
```

FIG.2

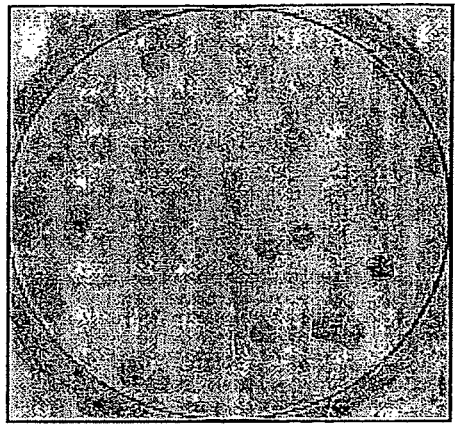
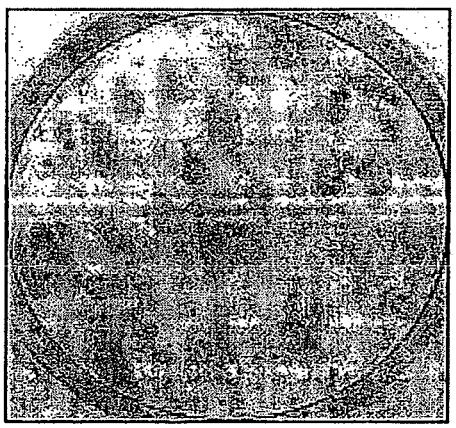
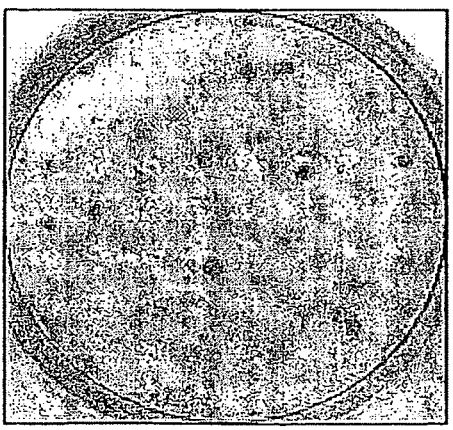
FIG.4

DENGUE SEROTYPE 2 ATTENUATED STRAIN

CROSS-REFERENCE TO RELATED APPLICATIONS

The present application is a continuation of U.S. application Ser. No.: 12/633,459, filed Dec. 8, 2009 (U.S. Pat. No. 8,067,566), which is a divisional of U.S. application Ser. No.: 11/453,344, filed Jun. 15, 2006 (U.S. Pat. No. 7,641,908), which claims the benefit of U.S. provisional application 60/691,274, filed on Jun. 17, 2005, all of said references incorporated herein by reference.

The invention relates to new live attenuated VDV2 (VERO-Derived Dengue serotype 2 virus) strains which are derived from the wild-type dengue-2 strain 16681 by passaging on PDK and Vero cells sanitization. The invention further relates to a vaccine composition which comprises such VDV2 strain.

Dengue diseases are caused by four closely related, but antigenically distinct, virus serologic types (Gubler, 1988; Kautner et al., 1997; Rigau-Perez et al., 1998; Vaughn et al., 1997), of the genus Flavivirus (Gubler, 1988). Infection with a dengue virus serotype can produce a spectrum of clinical illnesses ranging from a non-specific viral syndrome to severe, fatal haemorrhagic disease. The incubation period of dengue fever (DF) after the mosquito bite averages 4 days (range 3-14 days). DF is characterised by biphasic fever, headache, pain in various parts of the body, prostration, rash, lymphadenopathy and leukopenia (Kautner et al., 1997; Rigau-Perez et al., 1998). The viremic period is the same as of febrile illness (Vaughn et al., 1997). Recovery from DF is usually complete in 7 to 10 days but prolonged asthenia is common. Leukocytes and platelets counts decreases are frequent.

Dengue haemorrhagic fever (DHF) is a severe febrile disease characterised by abnormalities of homeostasis and increased vascular permeability that can lead to hypovolemia and hypotension (dengue shock syndrome, DSS) often complicated by severe internal bleeding. The case fatality rate of DHF can be as high as 10% without therapy, but below 1% in most centres with therapeutic experience (WHO Technical Guide, 1986).

Routine laboratory diagnosis of dengue infections are based on virus isolation and/or the detection of dengue virus-specific antibodies.

Dengue disease is the second most important tropical infectious disease after malaria, with over half of the world's population (2.5 billion) living in areas at risk for epidemic transmission. An estimated 50 to 100 million cases of dengue, 500,000 hospitalised DHF patients and 25,000 deaths occur each year. Dengue is endemic in Asia, the Pacific, Africa, Latin America, and the Caribbean. More than 100 tropical countries have endemic dengue virus infections, and DHF have been documented in more than 60 of these (Gubler, 2002; Monath, 1994). A number of well described factors appear to be involved in dengue infections: population growth, unplanned and uncontrolled urbanisation particularly in association with poverty, increased air travel, lack of effective mosquito control, and the deterioration of sanitary and public health infrastructure (Gubler, 2002). The awareness of dengue in travellers and expatriates is increasing (Shirtcliffe et al., 1998). Dengue has proven to be a major cause of febrile illness among US troops during deployments in dengue-endemic tropical areas (DeFraites et al., 1994).

The viruses are maintained in a cycle that involves humans and *Aedes aegypti*, a domestic, day-biting mosquito that prefers to feed on humans. Human infection is initiated by the injection of virus during blood feeding by an infected *Aedes aegypti* mosquito. Salivary virus is deposited mainly in the extravascular tissues. The primary cell subset infected after inoculation is dendritic cells, which subsequently migrate to draining lymph nodes (Wu et al., 2000). After initial replication in the skin and draining lymph nodes, virus appears in the blood during the acute febrile phase, generally for 3 to 5 days.

Monocytes and macrophages are with dendritic cells among the primary target of dengue virus. Protection against homotypic reinfection is complete and probably lifelong, but cross-protection between dengue types lasts less than 12 weeks (Sabin, 1952). Consequently a subject can experience a second infection with a different serotype. A second dengue infection is a theoretical risk factor of developing severe dengue disease. However, DHF is multifactorial including: the strain of the virus involved, as well as the age, immune status, and genetic predisposition of the patient. Two factors play a major role in the occurrence of DHF: a rapid viral replication with high viremia (the severity of the disease being related to the level of viremia (Vaughn et al., 2000) and an important inflammatory response with release of high levels of inflammatory mediators (Rothman and Ennis, 1999).

There is no specific treatment against Dengue diseases. The management of DF is supportive with bed rest, control of fever and pain with antipyretics and analgesics, and adequate fluid intake. The treatment of DHF needs correction of fluid loss, replacement of coagulation factors, and infusion of heparin.

Preventive measures presently rely on vector control and personal protection measures, which are difficult to enforce and expensive. No vaccine against dengue is currently registered. Since the 4 serotypes of dengue are circulating worldwide and since they are reported to be involved in cases of DHF, vaccination should ideally confer protection against all 4 dengue virus serotypes.

Live attenuated vaccines (LAVs), which reproduce natural immunity, have been used for the development of vaccines against many diseases, including some viruses belonging to the same genus as dengue (examples of commercially available flavivirus live-attenuated vaccines include yellow fever and Japanese encephalitis vaccines). The advantages of live-attenuated virus vaccines are their capacity of replication and induction of both humoral and cellular immune responses. In addition, the immune response induced by a whole virion vaccine against the different components of the virus (structural and non-structural proteins) reproduced those induced by natural infection.

A dengue vaccine project was initiated in Thailand at the Centre for Vaccine Development, Institute of Sciences and Technology for Development Mahidol University. Candidate live-attenuated vaccines were successfully developed, at a laboratory scale, for dengue serotype 1 (strain 16007, passage 13), serotype 2 (strain 16681, passage 53=LAV2), and serotype 4 (strain 1036, passage 48) viruses in Primary Dog Kidney (PDK) Cells, and for serotype 3 (strain 16562) in Primary Green Monkey Kidney (PGMK) cells (passage 30) and Fetal Rhesus Lung (FRhL) cells (passage 3). These vaccines have been tested as monovalent (single serotype), bivalent (two serotypes), trivalent (three serotypes), and tetravalent (all four serotypes) vaccines in Thai volunteers. Those vaccines were found to be safe and immunogenic in children and in adults (Gubler, 1997). These LAV 1-4 strains have been described in EP 1159968 in the name of the Mahidol University and were deposited before the CNCM (CNCM I-2480; CNCM I-2481; CNCM I-2482 and CNCM I-2483 respectively).

The Den-2 strain 16681 was recovered from serum of a DHF (Dengue Hemorrhagic Fever) patient in Bangkok in 1964 (Halstead et al., 1970). The original viremic serum had been passaged 4 times on BSC-1 cells (African Green Monkey kidney cells) and 5 times on continuous LLC-MK.sub.2 cells (Rhesus Monkey kidney cells). In 1977, the virus was passaged once in vivo, in susceptible monkeys (*Macaca Mulatta*), and then again in LLC-MK.sub.2 cells. Two additional passages in mosquitoes (*Toxorhynchites amboinensis*) were conducted in 1980. Virus attenuation was performed by passages at 32.degree. C. on PDK cells (Primary Dog Kidney cells). Attenuation of the strain was checked according to several in vitro and in vivo markers. Passage 50 fullfilled all these attenuation criteria and was chosen as master seed for vaccine production (1982), at passage 53. DEN-2 PDK53 vaccine candidate was evaluated in humans and found to be strongly immunogenic with no untoward clinical signs and symptoms (Bhamarapravati et al., 1989).

The complete sequence of the Dengue 2 Live-Attenuated Virus strain (LAV2) was established by R. Kinney et al. (CDC, Fort Collins) in 2001. Sequence differences between parent DEN-2 strain 16681 (SEQ ID No.3) and LAV2 (SEQ ID No.38) strain are described in Table 1. Thus, genetic comparison of the wild-type virus strain 16681 and LAV2 strain showed a set of 9 point mutations which could be linked to LAV2 attenuation.

TABLE 1

DEN-2 16681 and DEN-2 16681/
PDK53 (LAV2) Sequence Differences

| coordinates | | LAV2 | | 16681 | |
| --- | --- | --- | --- | --- | --- |
| Gene-aa | position | Nt | Aa | nt | aa |
| Non coding | Nt-57 | T | — | C | — |
| PrM-29 | Nt-524 | T | Val | A | Asp |
| E-373 | Nt-2055 | T | Phe | C | Phe |
| NS1-53 | Nt-2579 | A | Asp | G | Gly |
| NS2A-181 | Nt-4018 | T | Phe | C | Leu |
| NS3-250 | Nt-5270 | A/T | Val/Glu | A | Glu |
| NS3-342 | Nt-5547 | C | Arg | T | Arg |
| NS4A-75 | Nt-6599 | C | Ala | G | Gly |
| NS5-334 | Nt-8571 | T | Val | C | Val |

Nucleotide changes modifying the corresponding codon are indicated in bold.

The LAV2 strain which was initially established in 1983 was further rapidly identified as potential vaccine candidate (Bhamarapravati and Yoksan, 1997).

However, at that time, transmission to humans of Spongiform Encephalitis through mammalian cultures was not perceived as a risk and the virus was routinely maintained in Primary Dog Kidney cells (PDK). Furthermore, this LAV2 strain corresponds to a heterogeneous population. This heterogeneity represents an additional risk due to a potential in vitro or in vivo selection of one of the strain present in the composition.

In view of these increasing concerns, the Applicant decided to set up a sanitization process in order to get rid of any such risks. By transfecting Vero cells with the purified genomic RNA of LAV2, followed by three cycles of amplification in Vero cells, and two successive steps of virus plaque purification the Applicant produced a new Vero-Derived serotype 2 virus (VDV2).

This new VDV2 strain which has been thus derived by transfer to VERO cells and biological cloning differs from the LAV2 strain by sequence, an homogenous plaque size and temperature sensitivity but importantly has conserved some phenotypic and genotypic features of the LAV2 such as e.g. attenuation spots, small plaque phenotype, growth restriction at high temperature and has conserved the immunogenic features of the LAV2 strains. These features make this new strain a valuable vaccine candidate for prophylactic immunization in humans.

Definitions

"Dengue viruses" are positive-sense, single-stranded RNA viruses belonging to the Flavivirus genus of the flaviridae family. In the case of dengue serotype 2 (DEN-2) strain 16681, the entire sequence is 10723 nucleotides long (SEQ ID No.3). The RNA genome contains a type I cap at the 5'-end but lacks a 3'-end poly (A)-tail. The gene organization is 5'-noncoding region (NCR), structural protein (capsid (C), premembrane/membrane (prM/M), envelope (E)) and non structural protein (NS1-NS2A-NS2B-NS3-NS4A-NS4B-NS5) and 3' NCR. The viral RNA genome is associated with the C proteins to form nucleocapsid (icosahedral symmetry). As with other flaviviruses, the DEN viral genome encodes the uninterrupted open reading frame (ORF) which is translated to a single polyprotein.

Serial passaging of a virulent (disease-causing) strain of dengue-2 results in the isolation of modified virus which are "live attenuated", i.e., infectious, yet not capable of causing disease. These modified viruses are usually tested in monkeys to evaluate their attenuation. However, Humans are the only primates that exhibit signs of clinical disease. The viruses that cause mild (i.e. acceptable in terms of regulatory purposes as presenting a positive benefit/risk ratio) to low or no secondary effects (i.e. systemic events and/or biological abnormalities and/or local reactions) in the majority of the tested humans but still infect and induce an immune response are called "live attenuated".

The term "LAV" denotes live attenuated Dengue viral strains. In the context of the invention "LAVs" are live attenuated strains initially derived from the Dengue serotype 2 (DEN-2) strain 16681 by passages in Primary Dog Kidney (PDK) Cells. For instance "LAV2/PDK53" is the attenuated strain established after 53 passages of strain 16681 in PDK cells (DEN-2 16681/PDK53). "LAV2/PDK50" is the attenuated strain established after 50 passages of strain 16681 in PDK cells (DEN-2 16681/PDK50). LAV2/PDK53 nucleotide sequence is shown in SEQ ID No.38.

"VDV2" is meant a LAV obtainable by the sanitization process disclosed in the present application. A VDV2 is thus a biological clone (homogeneous) VERO-adapted Dengue serotype 2 virus capable of inducing a specific humoral immune response including neutralizing antibodies in primate especially in humans. The VDV2 strains of the invention can be easily reconstructed starting directly from the here disclosed VDV2 sequences. The induction of a specific humoral immune response can be easily determined by an ELISA assay. The presence of neutralising antibody in the serum of a vaccinee is evaluated by the plaque reduction neutralization test as described in section 4.1.1.2.2. A serum is considered to be positive for the presence of neutralizing antibodies when the neutralizing antibody titer thus determined is at least superior or equal to 1:10.

The terms "mutation" means any detectable change in genetic material, e.g. DNA, RNA, cDNA, or any process, mechanism, or result of such a change. Mutations include substitution of one or more nucleotides. In the context of the instant application, mutations identified in dengue-2 virus genomic sequence or polyprotein are designated pursuant to the nomenclature of Dunnen and Antonarakis (2000). As defined by Dunnen and Antonarakis at the nucleic acid level, substitutions are designated by ">", e.g. "31A>G" denotes that at nucleotide 31 of the reference sequence a A is changed to a G.

Variations at the protein level describe the consequence of the mutation and are reported as follows. Stop codons are designated by X (e.g. R97X denotes a change of Arg96 to a termination codon). Amino acid substitutions a designated for instant by "59G", which means that Ser in position 9 is replaced by Gly.

VERO-Derived Dengue Serotype 2 Viruses (VDV2)

The composition of the previously developed dengue-2 vaccine candidate LAV2 was improved by a sanitization process.

The VERO-Derived Vaccine Dengue serotype 2 (VDV2) disclosed herein uses the DEN-2 16681 virus attenuated by serial passages on PDK cells. VDV2 contains the genomic sequence of the whole live-attenuated DEN-2 virus, and bears the same attenuation spots which have been linked to attenuation as the original LAV2 strain that was tested in humans.

Sanitization of the LAV2 vaccine was performed by removing proteins and introducing only purified viral genomic material into Vero cells. More specifically, sanitization of the strain was performed by purifying and transfecting viral RNA into Vero cells. The process comprises the following steps:

a) extracting and purifying viral RNA from plaque-purified LVA2 strain, e.g. DEN-2 16681/PDK50 viruses;

b) advantageously associating of the purified RNA with cationic lipids;

c) transfecting Vero cell, in particular Vero cell LS10;

d) recovering of the neo-synthesized virus; and e) purifying a VDV strain by plaque purification and optionally amplifying it in host cells, especially Vero cells.

The Vero cell technology is a well-known technology which has been used for different commercial products (injectable and oral polio vaccines, rabies vaccine). In the present invention qualified Vero cells were advantageously used to guarantee the absence of any risks potentially linked to the presence of adventitious agents. By "qualified VERO cells" is meant cells or cell lines for which culture conditions are known and is such that the said cells are free from any adventitious agents. These include e.g. the VERO cell LS10 of Sanofi Pasteur.

The thus isolated VDV strains are classically stored either in the form of a freezed composition or in the form of a lyophilised product. For that purpose, the VDV can be mixed with a diluent classically a buffered aqueous solution comprising cryoprotective compounds such a sugar alcohol and stabilizer. The pH before freezing or lyophilisation is advantageously settled in the range of 6 to 9, e.g. around 7 such as a pH of 7.5.+−.0.2 as determined by a pH meter at RT. Before use, the lyophilised product is mixed with a pharmaceutically diluent or excipient such as a sterile NaCl 4% solution to reconstitute a liquid immunogenic composition or vaccine.

The Glu variant of LAV2 vaccine strain, at position NS3-250, was selected during transfection and cloning, and positions 5'NC-57 and NS1-53, also identified as critical for attenuation of LAV2 vaccine, were both conserved in VDV2 sequence.

Sequencing, at attenuation-specific loci, of virus recovered after transfection, did not reveal any mutation, compared to SEQ ID No.38. The biologically cloned VDV2 virus exhibits a homogenous plaque phenotype and a remarkable genetic stability with regard to its LAV2 parent as it can be deduced especially from the conservation of the attenuation genotype.

VDV2 (passage 11) strain was sequenced and compared with the serotype 2 Dengue Live Attenuated Virus (LAV2) strain sequence (SEQ ID No.38). A set of 10 nucleotide differences was identified, triggering six amino acid substitutions located in M and Env structural peptides, and also in non-structural peptides NS3 and NS5. None of these differences corresponds to any of the LAV2 attenuation positions.

TABLE 2

Sequence comparison between LAV2/PDK53 and VDV2 passage 11 strains.

| Nucleotides | | | Amino Acids | | |
|---|---|---|---|---|---|
| Position | LAV2 | VDV2 | Region Position | LAV2 | VDV2 |
| 736 | G | C | M 9 | G | R |
| 1619 | G | A | E 228 | G | E |
| 1638 | A | G | E 234 | K | K |
| 2520 | G | A | NS1 33 | K | K |
| 4723 | T | A | NS3 69 | S | T |
| 5062 | G | C | NS3 181 | D | H |
| 9191 | G | A | NS5 541 | R | K |
| 9222 | A | G | NS5 551 | E | E |
| 10063 | T | A | NS5 832 | S | T |
| 10507 | A | G | 3'nc | — | — |

Grey shading: differences in structural proteins; Bold characters: differences in non-structural proteins.

The invention thus provides for live attenuated dengue-2 virus strains that have been obtained from the wild type virus DEN-2 16681 attenuated by serial passages on PDK cells and then by sanitization on VERO cells. In particular the attenuated strains of the invention comprise at least the identified sequence mutations (non-silent and optionally silent) relative to the nucleotide sequence or polyprotein sequence of the wild-type DEN-2 16681 and LAV2/PDK53 strains.

Accordingly, the invention relates to an isolated live attenuated dengue-2 virus strain which comprises, or consists of, the sequence of LAV2/PDK53 strain (SEQ ID No.38) wherein at least nucleotides at positions 736, 1619, 4723, 5062, 9191, 10063, and 10507, and optionally 1638, 2520, 9222, and 10361, are mutated, with the proviso that the following nucleotides are not mutated: 57, 524, 2055, 2579, 4018, 5547, 6599, and 8571. Preferably, the mutations are substitutions. Preferably, the nucleotide at position 736 is C, the nucleotide at position 1619 is A, the nucleotide at position 4723 is A, the nucleotide at position 5062 is A, the nucleotide at position 9191 is A, the nucleotide at position 10063 A, and the nucleotide at position 10507 is G.

The nucleotide at position 5270 may be A or T, preferably A.

Still preferably, the isolated strain according to the invention comprises the sequence SEQ ID No.38 wherein said sequence comprises at least the mutations 736 G>C, 1619 G>A, 4723 T>A, 5062 G>C, 9191 G>A, 10063 T>A, and 10507 A>G, and optionally the mutation 1638 A>G, 2520 G>A, and/or 9222 A>G.

Hence, a live attenuated dengue-2 virus strain according to the invention may comprise, or consist of, the sequence of wild-type dengue-2 strain 16681 (SEQ ID No.3) wherein said sequence comprises at least the mutations 57 C>T, 524 A>T, 736 G>C, 1619 G>A, 2055 C>T, 2579 G>A, 4018 C>T, 4723 T>A, 5062 G>C, 5547 T>C, 6599 G>C, 8571 C>T, 9191 G>A, 10063 T>A, and 10507 A>G. Preferably, a live attenuated strain according to the invention further comprises the mutation 1638 A>G, 2520 G>A, and/or 9222 A>G by reference to the nucleotide sequence of wild-type strain 16681 (SEQ ID No.3).

The live attenuated dengue-2 virus strains according to the invention may include variant strains that comprise a sequence SEQ ID No.38 mutated at positions 736, 1619, 4723, 5062, 9191, 10063, and 10507, as defined above, and that further comprise a substitution of one or more nucleotides in a given codon position that results in no alteration in the amino acid encoded at that position.

Advantageously, the live attenuated dengue-2 virus strain according to the invention comprises a sequence which differs by a limited number of mutations, e.g. no more than 5, still preferably no more than 2, from SEQ ID No.1.

Preferably, the genomic sequence of a dengue-2 virus strain according to the invention consists of the nucleotide sequence SEQ ID No.1.

The invention also relates to live attenuated dengue-2 strains that may be derived from the VDV2 strain of sequence SEQ ID No.1 by further passages on cells, in particular Vero cells.

The invention also relates to an isolated nucleic acid which comprises, or consists of, the DNA sequence SEQ ID No.1 or its equivalent RNA sequence.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix.

As used herein, by RNA sequence "equivalent" to SEQ ID No.1 is meant a sequence SEQ ID No.1 wherein deoxythymidines have been replaced by uridines. As SEQ ID No.1 constitutes VDV2 cDNA sequence, the equivalent RNA sequence thus corresponds to the positive strand RNA of VDV2.

The invention further relates to the polyprotein of sequence SEQ ID No.2 and to fragments thereof. SEQ ID No.2 is the sequence of the polyprotein encoded by SEQ ID No.1 A "fragment" of a reference protein is meant a polypeptide which sequence comprises a chain of consecutive amino acids of the reference protein. A fragment may be at least 8, at least 12, at least 20, amino acid long.

Said fragments of the polyprotein of sequence SEQ ID No.2 comprise at least an arginine at position 9 of M protein (position 214 of SEQ ID No.2), and/or a glutamic acid at position 228 of E protein (position 508 of SEQ ID No.2), and/or a threonine at position 69 of NS3 protein (position 1543 of SEQ ID No.2), and/or a histidine at position 181 of NS3 protein (position 1656 of SEQ ID No.2), and/or a lysine at position 541 of NS5 protein (position 1725 of SEQ ID No.2), and/or a threonine at position 832 of NS5 protein (position 3032 of SEQ ID No.2).

According to an embodiment the fragment of the polyprotein encoded by SEQ ID No.1 is or comprises M protein, and/or E protein, and/or NS3 protein and/or NS5 protein.

Immunogenic and Vaccine Compositions

The invention also relates to an immunogenic composition, suitable to be used as a vaccine, which comprises a VDV2 strain according to the invention.

The immunogenic compositions according to the invention elicit a specific humoral immune response toward the dengue virus comprising neutralizing antibodies.

Preferably, the immunogenic composition is a vaccine.

According to an embodiment, the immunogenic is a monovalent composition, i.e. it elicits en immune response and/or confers protection against Dengue-2 virus only.

According to another embodiment, the invention relates to a multivalent dengue immunogenic composition. Such a multivalent immunogenic composition or vaccine may be obtained by combining individual monovalent dengue vaccines. The immunogenic or vaccine composition may further comprise at least a live attenuated dengue virus of another serotype. In particular, the immunogenic or vaccine composition may comprise a VDV2 according to the invention in combination with at least a live attenuated dengue virus selected from the group consisting of serotype 1, serotype 3, and serotype 4.

Preferably, the immunogenic or vaccine composition may be a tetravalent dengue vaccine composition, i.e. a vaccine composition that comprises a VDV2 according to the invention in combination with a live attenuated dengue-1 virus strain, a live attenuated dengue-3 virus strain and a live attenuated dengue-4 virus strain.

Live attenuated dengue-1, dengue-3 and dengue-4 virus strains have been described previously. Reference may be made to the live-attenuated vaccines that were developed by Mahidol University by passaging dengue serotype 1 (strain 16007, passage 13; LAV1), and serotype 4 (strain 1036, passage 48, LAV4) viruses in Primary Dog Kidney (PDK) Cells, and for serotype 3 (strain 16562) in Primary Green Monkey Kidney (PGMK) cells (passage 30) and Fetal Rhesus Lung (FRhL) cells (passage 3) (LAV3). The nucleotide sequences of LAV1 (SEQ ID No.40), LAV3 (SEQ ID No.41), and LAV4 (SEQ ID No.42) are shown in the annexed sequence listing.

Advantageously, a live attenuated dengue-1 strain may correspond to a VDV1 strain which has been obtained from the LAV1 strain developed by Mahidol by the process of sanitization according to the invention. In particular a live attenuated dengue-1 strain (VDV1) may comprise, and advantageously consists of the sequence SEQ ID No.39.

Immunogenic compositions including vaccines may be prepared as injectables which can correspond to liquid solutions, suspensions or emulsions. The active immunogenic ingredients may be mixed with pharmaceutically acceptable excipients which are compatible therewith.

The immunogenic compositions or vaccines according to the present invention may be prepared using any conventional method known to those skilled in the art. Conventionally the antigens according to the invention are mixed with a pharmaceutically acceptable diluent or excipient, such as water or phosphate buffered saline solution, wetting agents, fillers, emulsifier stabilizer. The excipient or diluent will be selected as a function of the pharmaceutical form chosen, of the method and route of administration and also of pharmaceutical practice. Suitable excipients or diluents and also the requirements in terms of pharmaceutical formulation, are described in Remington's Pharmaceutical Sciences, which represents a reference book in this field.

Preferably, the immunogenic composition or vaccine corresponds to an injectable composition comprising an aqueous buffered solution to maintain e.g. a pH (as determined at RT with a pH meter) in the range of 6 to 9.

The composition according to the invention may further comprise an adjuvant, i.e. a substance which improves, or enhances, the immune response elicited by the VDV2 strain. Any pharmaceutically acceptable adjuvant or mixture of adjuvants conventionally used in the field of human vaccines may be used for this purpose.

The immunogenic compositions or vaccines according to the invention may be administered by any conventional route usually used in the field of human vaccines, such as the parenteral (e.g. intradermal, subcutaneous, intramuscular) route In the context of the present invention immunogenic compositions or vaccines are preferably injectable compositions administered subcutaneously in the deltoid region.

Method for Immunizing

The invention further provides for a method of immunizing a host in need thereof against a dengue infection which comprises administering the host with an immunoeffective amount of a vaccine composition according to the invention.

A "host in need thereof" denotes a person at risk for dengue infection, i.e. individuals travelling to regions where dengue virus infection is present, and also inhabitants of those regions.

The route of administration is any conventional route used in the vaccine field the choice of administration route depends on the formulation that is selected preferably, the immunogenic composition or vaccine corresponds to an injectable composition administered via subcutaneous route, advantageously in the deltoid region.

The amount of LAV or VDV, in particular VDV2, in the immunogenic compositions or vaccines may be conveniently expressed in viral plaque forming unit (PFU) unit or Cell Culture Infectious Dose 50% ($CCID_{50}$) dosage form and prepared by using conventional pharmaceutical techniques. For instance, the composition according to the invention may be prepared in dosage form containing 10 to $10^6$ $CCID_{50}$, or $10^3$ to $10^5$ $CCID_{50}$ of LAV or VDV, for instance a dose of $4\pm0.5$ $\log_{10}$ $CCID._{50}$ of VDV2 strain for a monovalent composition. Where the composition is multivalent, to reduce the possibility of viral interference and thus to achieve a balanced immune response (i.e. an immune response against all the serotype contained in the composition), the amounts of each of the different dengue serotypes present in the administered vaccines may not be equal.

An "immunoeffective amount" is an amount which is capable of inducing a specific humoral immune response comprising neutralising antibodies in the serum of a vaccinee, as evaluated by the plaque reduction neutralization test as described in section 4.1.1.2.2; a serum being considered to be positive for the presence of neutralizing antibodies when the neutralizing antibody titer thus determined is at least superior or equal to 1:10.

The volume of administration may vary depending on the route of administration. Subcutaneous injections may range in volume from about 0.1 ml to 1.0 ml, preferably 0.5 ml.

The optimal time for administration of the composition is about one to three months before the initial exposure to the dengue virus. The vaccines of the invention can be administered as prophylactic agents in adults or children at risk of Dengue infection. The targeted population thus encompasses persons which are naive as well as well as non-naive with regards to dengue virus. The vaccines of the invention can be administered in a single dose or, optionally, administration can involve the use of a priming dose followed by a booster dose that is administered, e.g. 2-6 months later, as determined to be appropriate by those of skill in the art. The invention will be further described in view of the following figures and examples.

FIGURES

FIG. 1 is a summary of History of VDV2 seed.

FIG. 2 is a flow chart that summarises the developed manufacturing process that gives rise to the Filled Product (monovalent), "ready to use" doses.

Figure 3:
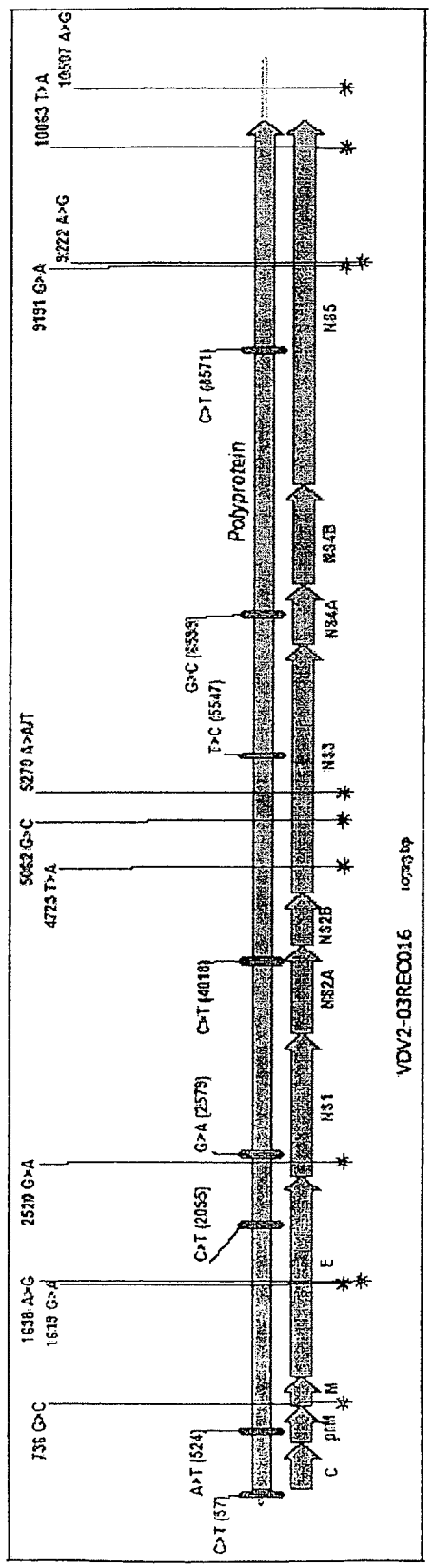

FIG. 3 is a diagrammatic representation of VDV2 genome map. The above arrow is the polyprotein coding sequence. The below arrows represent mature peptides coding sequence. The vertical bars symbolize the nucleotidic variations between wild-type dengue 2 strain 16681 and LAV2 strain. The stars designate the nucleotidic variations between LAV2 and VDV2.

FIG. 4 shows plaque size analysis after 7 days of incubation at 37° C. for dengue-1 viruses LAV2, VDV2, and strain 16681.

Figure 5:
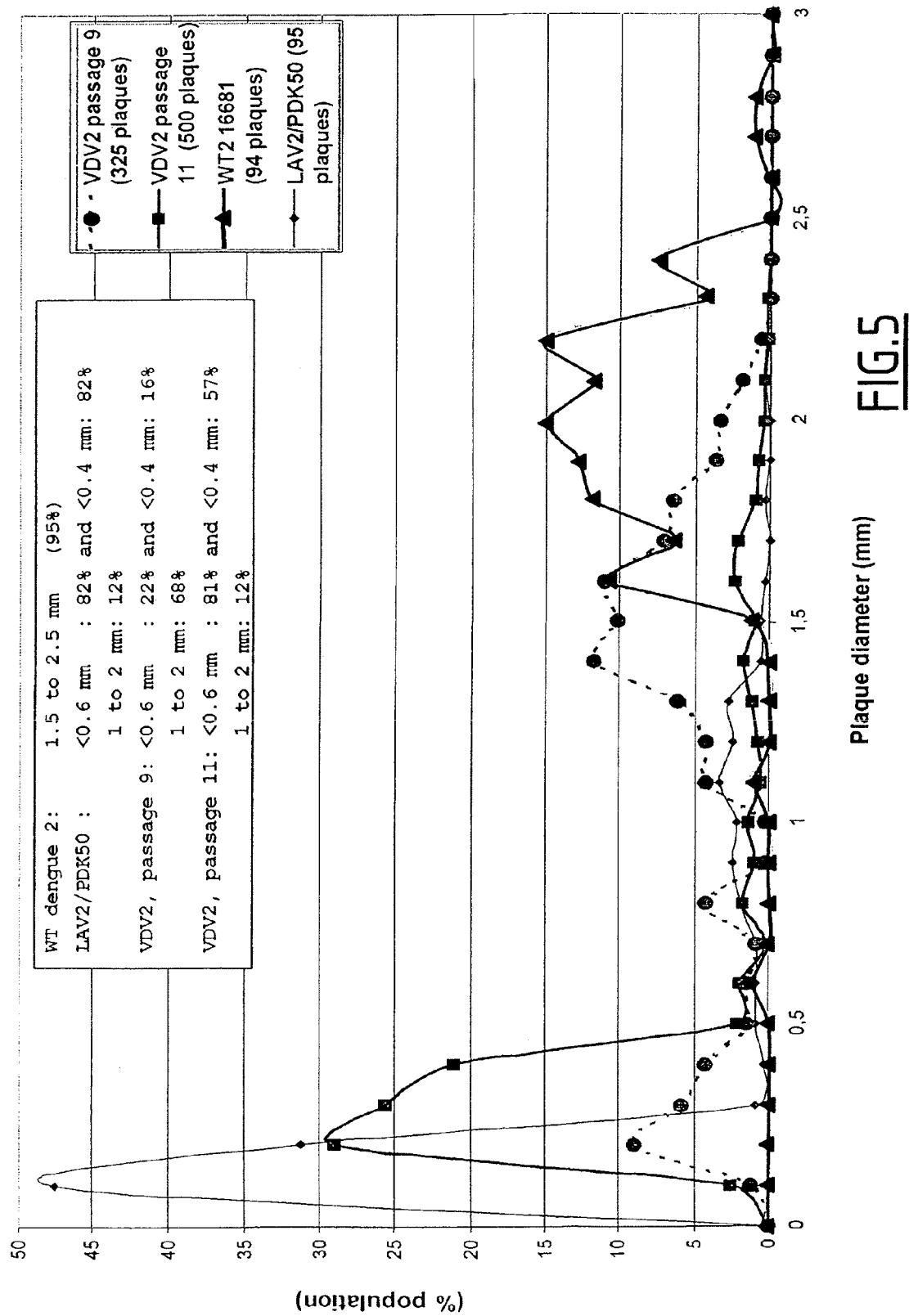

FIG. 5 is a graphic analysis showing plaque size distribution for dengue-2 viruses LAV2, VDV2, and strain 16681.

Figure 6:
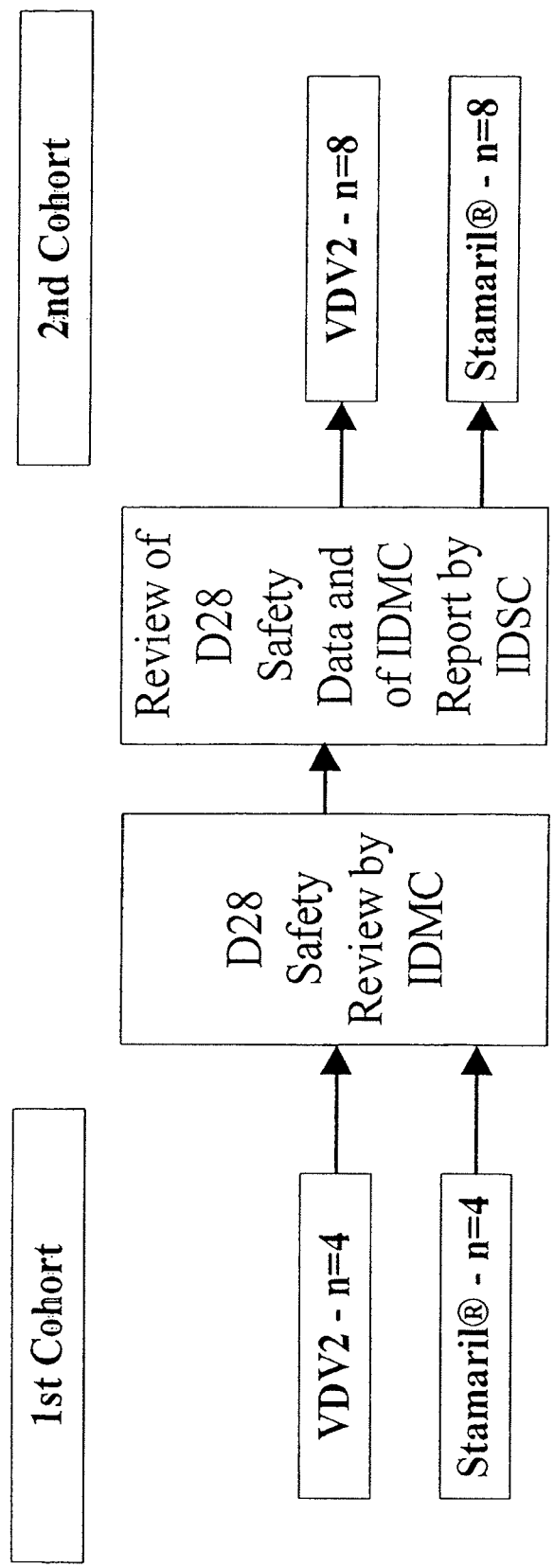

FIG. 6 is a summary of Trial Design for assessment of safety of VDV2 monovalent in healthy flavivirus-naive adults.

EXAMPLES

Example 1

Sanitization 1.1 Viral RNA Purification

The RNA purification and transfection process was performed as follows. DEN-2/PDK50 suspension was resuspended in 0.5 ml of water and diluted in order to contain at least $3\times10^4$ and up to $3\times10^7$ $TCID_{50}$ or PFU of virus per milliliter. One unit of benzonase diluted in 0.01 ml of William's medium was added to 0.5 ml of virus, in order to digest DNA or RNA molecules from cellular origin, and the solution was incubated for 2 hours at 4° C. on an agitator. At the end of incubation step, 0.65 ml of a denaturing buffer containing guanidium chloride, detergent (SDS), and pmercaptoethanol (RTL-.beta.mercaptoethanol buffer, provided in the kit RNeasy Mini kit, Qiagen Ref. 74104) were added and proteins were extracted once with phenol/chloroform (1/1) vol/vol and once with chloroform vol/vol, followed by centrifugation for 5 min at 14,000 rpm at room temperature. After each extraction, the aqueous phase was collected, taking care not to collect material (white precipitate) at the interface, and transferred to a clean 1 ml-Eppendorf tube. The RNA solution was then applied onto a QIAgen column following the recommendations of the manufacturer (RNeasy minikit, QIAgen), in order to remove traces of solvent, and eluted with 0.06 ml of nuclease-free $H_2O$ water. The presence of viral RNA was confirmed by quantitative RT-PCR, using a reference curve established with known quantities of virus, in $TCID_{50}$/ml.

1.2 Transfection of Vero Cells with Purified RNA

Transfection was performed using lipofectamine (LF2000 Reagent, Life Technologies), a mixture of cationic lipids that associate to RNA through charge interactions and allows transfer of the complexes into the cytoplasm of the cells by fusion with the cell membrane. The optimal quantity of LF2000 reagent was determined in a preliminary experiment by incubating Vero cells, plated 16 to 24 hours before (0.3-$0.5\times10.sup.^6$ cells per well in a 6 wells plate) with increasing doses (5 to 20 µl) of lipofectamine. Cells were then incubating 4 to 5 hours at 32° C., 5% $CO_2$, before replacing the medium by fresh culture medium without FCS, and the incubation was continued overnight at 32° C. Toxicity (round, refringent or floating cells, homogeneity of the cell monolayer) was checked regularly for 48 hours, under an inverted microscope. The highest dose of lipofectamine that was not toxic under these conditions was 10 µl and was chosen for RNA transfection.

Four transfections were carried out in parallel, using ¼ of the RNA preparation (about $2\times10^4$ log eq$TCID_{50}$, according to qRT-PCR). Twenty-five microliters of viral RNA solution were diluted in 500 .mu.l of OptiMEM medium (GIBCO) containing 15 .mu.l of LF2000 Reagent (a mixture of cationic lipids that associate to RNA through charge interactions, and allow transfer of the complexes into the cytoplasm of the cells by fusion with the cell membrane). 200 ng of yeast tRNA were added as carrier in 2 out of the 4 reactions.

The 4 transfection mixes were allowed to precipitate for 10 min at room temperature before addition to 6-wells plates of confluent Vero cells, and incubation at 36.degree. C. After four hours, transfection mix was removed and cells were rinsed once in PBS. Three milliliters of post-transfection medium (Williams, GIBCO) were added, and incubation was continued for 5 days at 32° C. Culture medium was then replaced by 3 ml of Dengue infection medium (Williams supplemented with 10 mM $MgSO_4$).

A focus of cells presenting typical cytopathic effects (round, refringent cells) was detected at day 8 post-transfection in 1 out of the 2 wells transfected in presence of tRNA. Release of virus in the supernatant of these cells was confirmed by qRT-PCR. Eleven days post-transfection, marked cytopathic effects were detected in this only well, while the supernatant of the three other transfected-wells remained negative.

The viral solution recovered after transfection was re-named TV100 (instead of 16681 PDK50Nero-2) and exhibited an infectious titer of 5.8 log $TCID_{50}$/ml after dilution at ½ in an aqueous buffered solution comprising cryoprotective agents (pH=7.5).

1.3 Characterization of Viruses Recovered After Transfection

Spot sequencing of specific loci important for attenuation was performed by R. Kinney (CDC, Fort Collins). Data are presented in Table 3.

TABLE 3

Sequencing of transfected virus at attenuation-specific positions

| Virus | 5'-NC-57 Nt 57 | NS1-53 Nt 2579 (aa) | NS3-250 Nt 5270 (aa) |
|---|---|---|---|
| DEN-2 16681 | C | G (Gly) | A (Glu) |
| DEN-2 PDK53 | T | A (Asp) | T/A (Val/Glu) |
| TV100 | T | A (Asp) | A (Glu) |

VDV2 has retained the important attenuating loci at 5'NC-57 and NS1-53, and the wild-type 16681 locus of the NS3-250-Glu variant in the PDK53 vaccine. The NS3-250-GluNal mix in the PDK53 vaccine was observed to be stable between passages PDK45 and PDK53 suggesting that selection has occurred in Vero cells. Previous analysis of DEN-2 vaccine isolated from serum of a vaccinee had demonstrated that this selection could also occur in humans.

Viral plaques diameters were measured in Vero cells. Briefly, Vero cells were plated at a density of 1.000.000 cells/$cm^2$ in culture medium containing 4% of FBS. After overnight incubation, the medium was removed and cells were infected with serial twofold or fivefold dilutions of virus. After 1.5 hour at 37° C. 5% $CO_2$, the inoculum was removed and cells were incubated at 37° C. 5% $CO_2$ in Mimimal Eagle Medium (MEM) containing 1.26% methylcellulose and 10% FBS. After 11 days of incubation, plates were fixed 20 minutes in cold acetone at −20° C. and revealed by immunocoloration with a flavivirus-specific mAb, diluted at 2.5 μg/ml. Viral plaques were measured using an image analysis software (Saisam/Microvision). VDV2 was compared to LAV2 16681/PDK50 seed (Table 4) and exhibited similar homogeneous small plaques of 1-3 mm diameter.

TABLE 4

Plaques size of LAV2 16681/PDK50 and VDV2

| Step | Virus | LP/MP | SP |
|---|---|---|---|
| Before transfection | LAV2 PDK50 | 0 | 319 |
| After transfection | Uncloned VDV2 | 0 | 183 |

LP/MP: Number of Large/Medium Plaques in 6 wells
SP: Number of Small Plaques in 6 wells

1.4 Plaque-Purifications

Three additional amplification passages (P2 to P4) were performed on the virus recovered after transfection. Biological cloning by plaque-purification was performed on P3 and P4 passaged virus (named LST 003 and LST 007, respectively).

Briefly, Vero cells were plated in 6-well plates and infected with serial dilutions of virus, in order to get between 1 and 20 plaques by plate. After 1.5 hour at 37° C. 5% $CO_2$, the inoculum was removed and cells were incubated under 3 ml of solid medium composed of MEM-10% FCS pre-heated at 42° C. and mixed extemporaneally with 2% of melted agarose equilibrated at 42° C. The medium was allowed to solidify at room temperature for 30 min; under flow hood, and plates were incubated in inverted position for 10 days at 32° C.-5% $CO.sub.2$. A second layer of the same medium supplemented with 0.01% of neutral red was then added and plates were incubated for an additional night at 32° C. Six well-isolated small plaques were picked under sterile conditions using a micro-pipet equipped with an 0.1 ml tip, and transferred into sterile tubes containing 0.2 ml of MEM4% FCS: three from P3 passage (identified as clones 31, 32 and 33), and three from P4 passage (identified as clones 71, 72 and 73). The suspension was homogenised by vortexing, serially diluted in the same medium, and immediately used to infect 6-well plates of Vero cells. The protocol was repeated and a second picking of two SP was done on clones 32, 33, 71 and 72, and one SP on clone 31. Each picked plaque was diluted in 1 ml of medium, before amplification on Vero cells, in T25 $cm.sup.2$ flasks. Culture medium was collected at day 6 post-infection, diluted with the same volume of an aqueous buffered solution comprising cryoprotective agent (pH 7.5) and frozen at −70° C. All these steps were performed at 32° C.

Plaque purified virus were named 311, 321, 322, 331, 332, 341, 342, 351, 352, 711, 712, 721 and 722, respectively.

Infectious titers were determined on Vero cells at the end of the first amplification (see below)

| | |
|---|---|
| Clone 311: 3.95 $LogCCID_{50}$/ml | |
| Clone 321: 5.20 $LogCCID_{50}$/ml | Clone 322: 5.45 $LogCCID_{50}$/ml |
| Clone 331: 5.55 $LogCCID_{50}$/ml | Clone 332: 4.95 $LogCCID_{50}$/ml |
| Clone 341: 2.80 $LogCCID_{50}$/ml | Clone 342: 4.85 $LogCCID_{50}$/ml |
| Clone 351: 5.35 $LogCCID_{50}$/ml | Clone 352: 5.50 $LogCCID_{50}$/ml |
| Clone 711: 5.45 $LogCCID_{50}$/ml | Clone 712: 5.65 $LogCCID_{50}$/ml |
| Clone 721: 5.30 $LogCCID_{50}$/ml | Clone 722: 5.60 $LogCCID_{50}$/ml |

A second amplification on Vero cells was carried out for three clones: clones 331, 352, and 722. Culture supernatants were collected at day 8 post-infection, diluted at ½ with an aqueous buffered solution comprising cryoprotective agent (pH 7.5) and named TV331, TV352 and TV722.

1.5 Characterization of Cloned Virus

After the $1^{st}$ amplification, all amplified viruses exhibited same plaque size phenotype and titers equivalent to, or higher than 5 log $CCID_{50}$/ml (except clones 311 and 341 which were significantly lower). Sequencing at attenuation-specific positions was performed on 6 clones from the $1^{st}$ amplification (clones 321, 331, 351, 352, 711, 721) and the three clones from the $2^{nd}$ amplification, and revealed no mutation.

In absence of any significant difference between the clones, TV722 was selected and amplified in VERO cells in order to generate a VDV2 vaccine candidate strain.

TABLE 5

Sequencing at attenuation-specific spots of DEN-2 viruses

| | | 5'-UTR | prM | E | NS1 | NS2a | NS3 | | NS4A | NS5 |
|---|---|---|---|---|---|---|---|---|---|---|
| Step/cell | Virus | 57 | 524 | 2055 | 2579 | 4018 | 5270 | 5547 | 6599 | 8571 |
| Wild-type/PGMK | 16681 | C | A | C | G | C | A | T | G | C |
| Vaccine/PDK | PDK53 | T | T | T | A | T | A/T | C | C | T |
| | TV 321 | T | T | T | A | T | A | C | C | T |
| | TV 331 | T | T | T | A | T | A | C | C | T |
| 2nd plaque-purification/VERO | TV 342 | T | T | T | A | T | A | C | C | T |
| | TV 352 | T | T | T | A | T | A | C | C | T |
| | TV 711 | T | T | T | A | T | A | C | C | T |
| | TV 722 | T | T | T | A | T | A | C | C | T |
| 2$^{nd}$ amplification/VERO | TV722PM | T | T | T | A | T | A | C | C | T |

Nucleotides position are indicated below each gene and referred to published sequence of DEN-2 16681 strain.

In conclusion, a total number of 11 passages was necessary to obtain a biological clone of DEN-2 166681/PDK50 adapted on VERO cells.

Further characterizations have been performed then by determining VDV2 passage 11 complete sequence and phenotypic testing.

Example 2

Sequencing

The complete sequence of the virus was generated according to the following strategy. Viral genomic RNA was purified. The full genome was amplified by 16 overlapping RT-PCR reactions. Each PCR was designed so that sequencing tags were added on each DNA strand. This allowed simpler sequence reactions, all driven by a single pair of universal sequencing primers. Each PCR product was individually sequenced on both DNA strands. All results were reassembled to reconstruct the full VDV2 genome.

2.1 Materials
2.1.1 Viruses

The viruses to which it is referred here are DEN-2 16681; LAV-2/PDK53; VDV2, the sequences of which are given in the attached sequence listing.

The complete genome sequence of these viruses is 10723 nucleotides in length.

2.1.2 Primers

All primers have been designed in Seqweb bioinformatics package (Accelrys), primer design module (Table 6).

TABLE 6 list of RT-PCT and sequencing primers

| Name | Primers sequences | NtStart | NtEnd | Primer length | RT-PCR length | Overlap |
|---|---|---|---|---|---|---|
| D2 01 + | GTTTTCCCAGTCACGACacgtggaccgacaaagacag (SEQ ID No. 4) | 13 | 32 | 37 | 978 | -32 |
| D2 01 - | AACAGCTATGACCATGttcctcctgaaacccttcc (SEQ ID No. 5) | 991 | 972 | 36 | | 371 |
| D2 02 + | GTTTTCCCAGTCACGACatcacgtacaagtgtcccc (SEQ ID No. 6) | 583 | 601 | 36 | 949 | |
| D2 02 - | AACAGCTATGACCATGagcaacaccatctcattgaag (SEQ ID No. 7) | 1532 | 1512 | 37 | | 163 |
| D2 03 + | GTTTTCCCAGTCACGACtgcaaccagaaaacttggaatacac (SEQ ID No. 8) | 1325 | 1349 | 42 | 948 | |
| D2 03 - | AACAGCTATGACCATGgctccatagattgctccaaagac (SEQ ID No. 9) | 2273 | 2251 | 39 | | 203 |
| D2 04 + | GTTTTCCCAGTCACGACcccagtcaacatagaagcagaacc (SEQ ID No. 10) | 2025 | 2048 | 41 | 878 | |
| D2 04 - | AACAGCTATGACCATGccaaagccatagtcttcaacttcc (SEQ ID No. 11) | 2903 | 2880 | 40 | | 155 |
| D2 05 + | GTTTTCCCAGTCACGACatcatgcaggcaggaaaac (SEQ ID No. 12) | 2707 | 2725 | 36 | 949 | |
| D2 05 - | AACAGCTATGACCATGaccataaccatcactcttccc (SEQ ID No. 13) | 3656 | 3636 | 37 | | 240 |
| 02 06 + | AACAGCTATGACCATGaccataaccatcactcttccc (SEQ ID No. 14) | 3368 | 3386 | 36 | 930 | |
| D2 06 - | AACAGCTATGACCATGgctctctccagttccaaatc (SEQ ID No. 15) | 4298 | 4279 | 36 | | 146 |
| D2 07 + | GTTTTCCCAGTCACGACaagaaccagcaagaaaaggag (SEQ ID No. 16) | 4113 | 4133 | 38 | 868 | |
| 02 07 - | AACAGCTATGACCATGcaccattaccataaagacccac (SEQ ID No. 17) | 4981 | 4960 | 38 | | 226 |

TABLE 6-continued list of RT-PCT and sequencing primers

| Name | Primers sequences | NtStart | NtEnd | Primer length | RT-PCR length | Overlap |
|---|---|---|---|---|---|---|
| D2 08 + | GTTTTCCCAGTCACGACttgaaccatcatgggcggac (SEQ ID No. 18) | 4715 | 4734 | 37 | 910 | |
| D2 08 − | AACAGCTATGACCATGtcctgcttttatacttggaacgaac (SEQ ID No. 19) | 5625 | 5601 | 41 | | 208 |
| D2 09 + | GTTTTCCCAGTCACGACaagcccatttcacagaccc (SEQ ID No. 20) | 5375 | 5393 | 36 | 920 | |
| D2 09 − | AACAGCTATGACCATGtcaatttcttcctttcccttc (SEQ ID No. 21) | 6295 | 6274 | 38 | | 158 |
| D2 10 + | GTTTTCCCAGTCACGACgagaggagaagcaaggaaaac (SEQ ID No. 22) | 6096 | 6116 | 38 | 923 | |
| D2 10 − | AACAGCTATGACCATGagggacacattcactgagg (SEQ ID No. 23) | 7019 | 7001 | 35 | | 233 |
| D2 11 + | GTTTTCCCAGTCACGACacagagaacaccccaagac (SEQ ID No. 24) | 6750 | 6768 | 36 | 929 | |
| D2 11 − | AACAGCTATGACCATGtccacttcctggattccac (SEQ ID No. 25) | 7679 | 7661 | 35 | | 308 |
| D2 12 + | GTTTTCCCAGTCACGACacaagtaatgctcctagtcctc (SEQ ID No. 26) | 7332 | 7353 | 39 | 935 | |
| D2 12 − | AACAGCTATGACCATGttcactgatgacactatgttcc (SEQ ID No. 27) | 8267 | 8246 | 38 | | 211 |
| D2 13 + | GTTTTCCCAGTCACGACgtcatcaccaaatcccacag (SEQ ID No. 28) | 8016 | 8035 | 37 | 937 | |
| D2 13 − | AACAGCTATGACCATGgcttcttctctcttttcccatc (SEQ ID No. 29) | 8953 | 8931 | 39 | | 140 |
| D2 14 + | GTTTTCCCAGTCACGACaaggtgagaagcaatgcag (SEQ ID No. 30) | 8773 | 8791 | 36 | 937 | |
| D2 14 − | AACAGCTATGACCATGtggaaatggtgtgaacagaag (SEQ ID No. 31) | 9710 | 9690 | 37 | | 209 |
| D2 15 + | GTTTTCCCAGTCACGACgcattcagcacctaacaatcac (SEQ ID No. 32) | 9641 | 9482 | 39 | 9335 | |
| D2 15 − | AACAGCTATGACCATGggcatttatgatggcctgac (SEQ ID No. 33) | 10396 | 10377 | 36 | | — |
| D2 16i + | ccatggaagctgtacgc (SEQ ID No. 34) | 10480 | 10496 | 64 | 234 | |
| D2 16i − | AACAGCTATGACCATGtgattcaacagcaccattcc (SEQ ID No. 35) | 10714 | 10695 | 36 | | −28 |

2.2 Methods

2.2.1 Viral RNA Purification

From previous experience, a minimal of 1000 DICC.sub.50 is required to get a positive RT-PCR reaction in the next steps. This means that a mimimum virus titer of $10^4$ DICC$_{50}$/mL is necessary. Virus genomic RNA was purified using QIAamp viral RNA mini kit (Qiagen), according to the manufacturer's recommendations. Briefly, a volume of 140 μl from a crude viral sample was incubated in the presence of the lysis solution, and loaded onto a kit column. After washing steps, the purified viral RNA was eluted by 60 μl of sterile nuclease-free water containing 1 μl (40 units) of RNAse inhibitor (RNAse Out, Sigma).

2.2.2 Reverse Transcription

Viral RNA was reverse transcribed into cDNA by a reverse transcriptase (reverse iT) from ABGene. Again, standard operating conditions were applied, using 10 μl of purified RNA, in a final reaction volume of 20 μl. The reaction was initiated by hybridization of the minus strand primers. One RT reaction per PCR was performed. The cDNA synthesis was obtained by 45 min incubation at 47° C.

2.2.3 PCR

All PCR were performed with Expand High Fidelity PCR system (Roche diagnostics), using all 16 pairs of primers (+) and (−) from Table 6. PCR conditions were the following ones:

| RT | 2 μl | PCR program | | |
|---|---|---|---|---|
| 10x buffer | 2.5 μl | Denaturation | 94° C. | 2 min |
| dNTP mix (10 mM) | 2 μl | Denaturation | 94° C. | 15 sec |
| Primers | 0.8 μl each | Hybridization | 55° C. | 30 sec  40 |
| H20 | 16.4 μl | Elongation | 68° C. | 1 min  cycles |
| Enzyme | 0/5 μl | Elongation | 68° C. | 5 min |

All PCR products were controlled by electrophoresis on agarose gel.

2.2.4 Sequencing

The major part of the sequence reactions has been outsourced to Genome Express. Genome extremities, ambiguities, some inter-PCR junctions, and regions not sequenced by Genome Express for technical reasons were performed in-house.

Sequencing at Genome Express: PCR products were shipped at +4° C., and sequencing results were received as informatic sequence files. Text file, quality files and chromatograms are available for each individual sequence. After sequence alignment, all discrepancies were checked on the chromatogram, and corrected if identified as sequence algorithm errors.

In-house sequencing: Sequence reactions were performed on thermocycler PTC-200 (MJ Research), with Sequitherm Excell II LC kit (Epicentre). Each PCR product was sequenced on both strands independently in a single reaction. Reactions were loaded onto a sequence electrophoresis gel. Run and analysis of sequence were performed on the automated sequencer Gene ReadIR 4200 (Li-Cor).

Sequence reaction

| DNA | up to 200/ 250 ng | PCR program | | | |
|---|---|---|---|---|---|
| Reaction buffer | 7.2 µl | Denaturation | 92° C. | 2 min | |
| Primers (1-2 pM) | 1.5 µl each | Denaturation | 92° C. | 15 sec | |
| Enzyme | 1 µl | Hybridization | 50° C. | 30 sec | 30 |
| H₂O | up to 20 µl | Elongation | 70° C. | 1 min | cycles |
| | | Elongation | 70° C. | 10 sec | |

Addition of 3 µl of denaturating/loading buffer.

Denaturation of samples 3 min at 95° C. and ice cooling just before samples loading.

Sequence Electrophoresis

| Electrophoresis parameters | | Gel parameters | |
|---|---|---|---|
| Voltage | 1500 V | Gel hight | 41 cm |
| Current | 35 mA | Gel thickness | 0.2 mm |
| Power | 40 W | Temperature | 45° C. |
| Run time | 9H00 | Scan speed | 3 |

2.3 Results

All PCR fragments were sequenced from both ends using a common PCR added ail, i.e. a specific motif which has been added at 5' end of all primers:

5' primers: M13SEQ-GTTTTCCCAGTCACGAC (SEQ ID No.36)

3' primers: M13REV-AACAGCTATGACCATG (SEQ ID No.37)

M13-SEQ and -REV sequences correspond to universal M13 primers motifs (New England Biolabs references).

For final contig assembly, a quick analysis was performed in Vector NTi, in ContigExpress module (Informax). The LAV2 reference sequence was compared with all individual sequencing results. In such conditions, all results could be aligned at the right place on the complete genome, even when some regions were still missing contig assembly, giving a quick visualization of the overall genome alignment.

2.3.1 Complete VDV2 Sequence Assembly

The final sequence alignment was performed in Vector NTi, AlignX module (Informax). The classical multiple sequence alignment algorithm ClustalW (Thompson et al., 1994) was used by the software to build the global alignment. All the sequence results were aligned together with the LAV2 reference sequence, thus allowing for a better reconstruction of the genome. Any discrepancy in the sequence with regard to the reference required a confirmation on another independent sequence reaction. The complete sequence of VDV2 is shown in SEQ ID No.1.

Some ambiguities are often found in single sequences, especially near sequence extremities. This is inherent to the somewhat poor quality of the reaction at both ends of any PCR fragment. Such poor quality sequences were excluded from the alignment, until two other independent sequence reactions were available from other PCR products. Discrepancy towards the reference was not taken into account in the final alignment when not confirmed in at least two independent other PCR sequences matching the consensus. Conversely, any discrepancy confirmed on two independent sequences was kept in the final sequence.

Table 7 summarizes the characteristics of each individual sequence reaction, indicating start, end and length. Overlaps between adjacent PCR are also indicated, as well as differences with regard to the reference sequence in the last column.

TABLE 7

Dengue VDV2 individual sequences characteristics

| Name | Start | End | Size | Overlap | Comments |
|---|---|---|---|---|---|
| D2 01 + | 33 | 365 | 332 | 0 | 2 sequences |
| D2 01 − | 619 | 79 | 540 | 5 | 2 sequences |
| D2 02 + | 614 | 1334 | 720 | | 736 G>C (M9-G>R) |
| D2 02 − | 1488 | 654 | 834 | 127 | 736 G>C (M9-G>R) |
| D2 03 + | 1361 | 2135 | 774 | | 1619 G>A (E228 G>E); 1638 A>G (E234K s) |
| D2 03 − | 2227 | 1416 | 811 | 179 | 1619 G>A (E228 G>E); 1638 A>G (E234K s) |
| D2 04 + | 2048 | 2774 | 726 | | 2520 G>A (NS1-33K s) |
| D2 04 − | 2866 | 2210 | 656 | 133 | 2520 G>A (NS1-33K s) |
| D2 05 + | 2733 | 3495 | 762 | | |
| D2 05 − | 3619 | 2819 | 800 | 251 | |
| D2 06 + | 3393 | 4196 | 803 | | |
| D2 06 − | 4257 | 3368 | 889 | 78 | |
| D2 07 + | 4179 | 4830 | 651 | | 4723 T>A (NS3-69 S>T) |
| D2 07 − | 4851 | 4223 | 628 | 130 | 4723 T>A (NS3-69 S>T) |
| D2 08 + | 4742 | 5506 | 764 | | 5062 G>C (NS3-181 DD>H) |
| D2 08 − | 5582 | 4721 | 861 | 188 | 5062 G>C (NS3-181 DD>H) |
| D2 09 + | 5394 | 6100 | 706 | | |
| D2 09 − | 6669 | 5979 | 690 | 545 | |
| D2 10 + | 6124 | 6996 | 872 | | |
| D2 10 − | 6983 | 6148 | 835 | 218 | |
| D2 11 + | 6778 | 7567 | 789 | | |

TABLE 7-continued Dengue VDV2 individual sequences characteristics

| Name | Start | End | Size | Overlap | Comments |
|---|---|---|---|---|---|
| D2 11 − | 7649 | 6781 | 868 | 317 | |
| D2 12 + | 7365 | 8236 | 971 | | |
| D2 12 − | 8241 | 7332 | 909 | 191 | |
| D2 13 + | 8050 | 8797 | 747 | | |
| D2 13 − | 8819 | 8147 | 672 | | |
| D2 14 + | 8707 | 9700 | 903 | 22 | 9191 G>A (NS5-541 R>K); 9222 A>G (NS5-551E s) |
| D2 14 − | 9654 | 8804 | 850 | 199 | 9191 G>A (NS5-541 R>K); 9222 A>G (NS5-551E s) |
| D2 15 + | 9501 | 10285 | 784 | | 10063 T>A (NS5-832 S>T) |
| D2 15 − | 10347 | 9702 | 645 | 187 | 10063 T>A (NS5-832 S>T) |
| D2 16i + | 10486 | 10687 | 201 | | 10507 A>G |
| D2 16i − | 10694 | 10160 | 534 | 0 | 10507 A>G |

The two extremities of the genome could not be sequenced from PCR amplification, because cDNA synthesis and PCR DNA reaction required oligonucleotides complementary to the ends of the genome. During the amplification step, these oligonucleotides are incorporated into the PCR fragment. The sequence result is that of the synthetic oligonucleotide, and not that of the virus itself. PCR from both ends of the virus genome did work properly, suggesting that the viral sequence was not significantly different from the oligonucleotide sequence (if it had been the case, PCR amplification should have failed or at least should have been of poor quality). We were not able to distinguish them from all other PCR amplifications. So, in the reconstructed genome, both genome ends were considered as identical to oligonucleotide sequences (and also identical to the reference). At 5' end, the sequence is that of nucleotides 1 to 32. At 3' end, the sequence is that of nucleotides 10695 to 10723.

2.3.2 Sequence Comparison

Ten nucleotide differences have been detected with regard to the parent LAV2 genomic sequence. VDV2 vaccine strain is derived from LAV2, through virus sanitization and passage from dog to monkey cells.

Differences between LAV2 and VDV2 can have several origins. First, cloning steps can select a viral subpopulation that is not 100% identical to the major sequence previously detected in LAV2. Second, LAV2 has been produced on PDK cells, whereas VDV2 has been made on Vero cells. Such passage from dog to monkey cells is known to potentially induce virus changes that reflect adaptation to the new cell line. Third, as for all RNA viruses, the lower viral RNA polymerase fidelity triggers a higher genomic mutation rate than DNA polymerases do.

In term of sequences, all 9 nucleotide positions which have been linked to viral attenuation of LAV2 are conserved in VDV2 passage 11.

Furthermore, sequence comparison between VDV2 passage 9 and passage 11 showed the occurrence of two mutations between passages 9 and 11 which are linked to differences in phenotype, viremia and immunogenicity.

TABLE 8

Sequence comparison between LAV2/PDK53 strain and VDV2 passages 9 and 11 strains

| | Nucleotides | | | Amino acids | | | | |
|---|---|---|---|---|---|---|---|---|
| | | VDV2 | | | | | VDV2 | |
| Position | LAV2 | Passage 9 | Passage 11 | Region | Position | LAV2 | Passage 9 | Passage 11 |
| 736 | G | G | C | M | 9 | G | G | R |
| 1619 | G | A | A | E | 228 | G | E | E |
| 1638 | A | G | G | E | 234 | K | K | K |
| 2520 | G | A | A | NS1 | 33 | K | K | K |
| 4723 | T | A | A | NS3 | 69 | S | T | T |
| 5062 | G | C | C | NS3 | 181 | D | H | H |
| 5270 | A/T | A | A | NS3 | 250 | E/V | V | V |

TABLE 8-continued

Sequence comparison between LAV2/PDK53 strain and VDV2 passages 9 and 11 strains

| | Nucleotides | | | | Amino acids | | | |
|---|---|---|---|---|---|---|---|---|
| | | VDV2 | | | | | VDV2 | |
| Position | LAV2 | Passage 9 | Passage 11 | Region | Position | LAV2 | Passage 9 | Passage 11 |
| 9191 | G | G | A | NS5 | 541 | R | R | K |
| 9222 | A | G | G | NS5 | 551 | E | E | E |
| 10063 | T | A | A | NS5 | 832 | S | T | T |
| 10507 | A | G | G | 3' nc | — | — | — | — |

Bold: sequence differences between VDV2 passage 9 and passage 11/

When performing sequence alignment between all available Genbank serotype 2 Dengue genomic sequences, it appears that only two positions are shared by other Dengue 2 strains (1638 and 2520), both silent at amino acid level. All other positions are specific to the VDV2 passage 11 strain, triggering an amino acid substitution (Table 8). Concerning amino acid changes, the four changes in non-structural peptides appear relatively conservative, from a biochemical point of view, whereas the two changes in M and in the envelope bring modification both in charge and hydrophobicity.

Example 3

Characterization

The objective of these studies was to assess whether changes in attenuation markers occurred through passages.

The flow chart shown on FIG. 2 summarises the developed manufacturing process that gives rise to the Filled Product (monovalent), "ready to use" doses Briefly, after 2 successive passages on Vero cells of the VDV2 passage 8, the respective working seeds were obtained. The final virus cultivations are also conducted by infection of a Vero cell suspension. The viruses produced are then harvested. DesoxyRiboNueleic Acid (DNA) is digested according to an enzymatic treatment. Impurities are removed by ultrafiltration. Infectious titers are enhanced by a concentration step. An aqueous buffered solution comprising cryoprotective agents (pH=7.5) is added and this 0.22-μm filtrated mixture is then diluted at the targeted dose within the same solution. The active substance is then filled into glass vials, freeze-dried, and stored before use.

3.1 Phenotypic Markers

Table 9 presents data from three phenotypic assays performed on DEN-2 16681 wt strain, DEN-2 16681/PDK53 vaccine strain, VDV2 passage 9 and VDV2 passage 11 (last adaptation passage): temperature-sensitivity (Ts), growth curves on monkey (Vero) and mosquito (C6/36) cells and neurovirulence in Newborn mice (data obtained at CDC). Reduced mouse neurovirulence (reduced mortality and longer average survival time (AST)), restricted-growth at 39° C. and restricted replication on C6/36 are currently accepted by the scientific community as attenuation criteria for Dengue viruses. Vero-adapted passages exhibit clear Ts profile, and are more restricted than DEN2/PDK53. Final adaptation passage is restricted by about 3 log in this assay. Temperature sensitivity was also confirmed by viral growth curves. On Vero cells, similar replication levels were observed with all tested viruses. On mosquito cells, viral growth of Vero-adapted viruses was clearly restricted (about 3 log) compared to wt DEN2, and slightly restricted (about 0.5 log) compared to DEN2-PDK53. Surprisingly, mouse neurovirulence of Vero-adapted viruses was close to neurovirulence of wt DEN2, and significantly higher than neurovirulence of DEN2/PDK53 vaccine. These data point out the low predictive value of this say, with regard to viral strain attenuation (et clinical data).

Plaque size distribution of VDV2 passages 9 and 11, DEN2/PDK53 and wtDEN2 are compared to FIG. 5. Wt DEN2 exhibits heterogenous profile with 95% of plaques with a size homogeneous profile, with a major population (81%) of plaques<0.6 mm and a minor population (12%) of 1-2 mm plaques. This profile is close to, but distinct from DEN2-PDK53 profile. Noteworthy, the intermediate adaptation passage, VDV2 P9, exhibits a more heteregenous profile, with a major population (70%) of 1-2 mm plaques, and a minor population (25%) of plaques<0.6 mm. These data demonstrate that VDV2 strain was not yet fully adapted at passage 9, and that the two additional passages were required for obtention of a homogeneous population replicating stably in Vero cells.

TABLE 9

Summary of DEN-2 viral phenotypes

| | Temperature sensitivity (Percent titer reduction at 39° C.)$_{Fold-reduction}$ | | | | | Growth curves (Peak $\log_{10}$ pfu/ml) Vero-LS10 | | Neurovirulence in newborn Swiss Webster mice | |
|---|---|---|---|---|---|---|---|---|---|
| Virus | Score | Day 3 | Day 4 | Day 5 | Day 6 | Titer | at Day | Mortality$_n$ | AST (S.D.) |
| D2-16681 | + | n.d. | 92.7$_{13.7}$ | n.d. | 92.2$_{12.8}$ | 7.5 | 8 | 100.0%$_{16}$ | 12.2 (1.5) |
| D2-PDK53 | + | n.d. | 96.6$_{29.4}$ | n.d. | 99.7$_{333.3}$ | 7.3 | 8-10 | 43.75%$_{16}$ | 16.0 (2.4) |

TABLE 9-continued

Summary of DEN-2 viral phenotypes

| Virus | Temperature sensitivity (Percent titer reduction at 39° C.)$_{Fold\ reduction}$ | | | | Growth curves (Peak $\log_{10}$ pfu/ml) Vero-LS10 | | Neurovirulence in newborn Swiss Webster mice | |
|---|---|---|---|---|---|---|---|---|
| | Score | Day 3 | Day 4 | Day 5 | Day 6 | Titer | at Day | Mortality$_n$ | AST (S.D.) |
| VDV2 P9 | + | n.d. | 99.94$_{1666.7}$ | n.d. | 99.97$_{3333.3}$ | 7.5 | 8-10 | 100.0%$_{16}$ | 10.9 (0.7) |
| VDV2 P11 | + | n.d. | 99.92$_{1250.0}$ | n.d. | 99.88$_{833}$ | 7.5 | 10 | 100.0%$_{16}$ | 10.9 (0.6) |

N: number of animals.

Example 4

Immunogencity, Viremia, and Toxicology in Monkeys

The most solid and numerous data that can be obtained in monkeys concern immunogenicity and viremia. Viremia, in particular, has been identified as one of the factors associated with virulence and disease severity in humans, and then constitute an important parameter to consider. Obviously, immunogenicity is a key parameter when testing vaccines.

Inventors have established minimal/maximal values for viremia and immunogenicity.

TABLE 10

Minimal requirements for responses induced by Dengue vaccine candidates in monkeys, as measured in Vero or LLC-MK2 cells by plaque assay (these cells being considered equivalent in such an assay)

| Viremia mean duration (days) (all serotypes being considered) | Viremia mean peak titer (log 10 pfu) (all serotypes being considered) | Mean neutralizing titer Day 30 (for each serotype) PRNT 50 |
|---|---|---|
| ≤3 days | ≤1.5-2 | ≥80 | pfu: plaque forming unit
PRNT 50: Plaque Reduction Neutralization Titer 50 (titre corresponding to a reduction of 50% of plaque number)

4.1 Pre-Clinical Pharmacology, Pharmacokinetics, and Product Metabolism in Animals 4.1.1 Material and Methods 4.1.1.1 Monkey Experiments Monkey experiments were carried out according to European guidelines regarding animal experiments.

Immunizations were performed on cynomolgus monkeys (*Macaca fascicularis*) originating from Mauritius (CRP Le Vallon). Monkeys were quarantined for 6 weeks in the animal facility of Sanofi Pasteur before immunization.

Monkeys were immunized by subcutaneous (SC) route in the arm with vaccines in a volume of 0.5 ml (see each respective section). After light anesthesia with ketamine (Imalgene, Merial), blood was collected by puncture of the inguinal or saphene veins. At days 0 and 28, 5 ml of blood were sampled for evaluating antibody responses while between days 2 and 10 only 1 ml of blood was sampled for evaluating viremia. Blood was collected on ice and kept on ice until serum separation. To do so, blood was centrifuged for 20 minutes at 4° C., and serum collected and stored at −80° C. until testing in Rich Kinney's laboratory. Shipment to USA was performed in dry ice.

4.1.1.2 Viremia and Neutralizing Antibody Responses (Plaque Reduction Neutralization Test, PRNT)

All analyses were performed in the laboratory of R. Kinney in CDC, Fort Collins, USA. Serum samples were shipped and stored at −80° C. until the time of testing. At the time of first thawing, the samples were tested for viremia, and a 1:5 dilution of the serum was made. The 1:5 serum dilutions were inactivated for 30 min at 56° C. before testing for neutralizing antibodies.

4.1.1.2.1 Viremia 0.125 ml of serum was added to 0.125 ml of diluent (RPMI medium) in the first well of 96-well plate and serial 10-fold dilution series were done, transferring 0.025 ml into 0.225 ml of diluent for each dilution. 0.2 ml of $10^{0.3}$-$10^{5.3}$ dilution series was plated in 6-well plate of Vero cells (virus was adsorbed at 37° C. for 1.5 hour, overlayed with 4 ml of agarose lacking neutral red, overlayed 6-7 days later with 2 ml of agarose containing neutral red, and plaques counted). The limit of virus detection was=10 PFU/ml. For controls stock DEN-16681 PDK-53 (LAV2) vaccine was plated.

4.1.1.2.2 PRNT (Plaque Reduction Neutralization Test)

Neutralizing antibodies were quantified as described in Huang et al. (2000). Briefly, 0.2 ml of heat-inactivated, 1:5 dilution of serum was added to the first well of 96-well plate and serial 2-fold dilution series were made, transferring 0.1 ml into 0.1 ml of diluent (RPMI medium) for each dilution. This resulted in a 1:10-1:320 serum dilution series. 0.1 ml of DEN virus (60-160 PFU; parental DEN2 16681 virus) was added to each serum dilution well for a total of 0.2 ml of serum-virus mixture. 96-well plates were incubated overnight at 4° C. 0.1 ml of serum-virus mixtures (containing 30-80 PFU of input virus) were plated in 6-well Vero plates (as indicated above in the Viremia section) and plaques were counted after staining with neutral red. Multiple back titrations of the input viruses at 2-fold, 1-fold, and 0.5-fold test concentrations provided direct experimental determination of the input PFU, which was the basis for determining 50% (PRNT$_{50}$) and 70% (PRNT$_{70}$) endpoint antibody titers. A negative serum result should have a neutralizing antibody titer of <1:10. Sera showing neutralization titers of 320 were retested at dilutions 1:80-1:2560 for determination of endpoint titer.

4.1.2 Evaluation of Monovalent VDV2 Candidate at Passage 9 in Monkeys

Purification/selection of VDV2 candidate has been conducted as described in example 1. The selected clones (based on phenotypic markers and sequence) have been tested after 9 passages in cell culture in Sanofi Pasteur on male cynomolgus macaques (*Macaca fascicularis*, mean weight 3.1 kg) originating from CRP Le Vallon, Mauritius.

After immunization on D0, viremia was followed from D2 to D10, and immunogenicity measured at D0 and D28. All viruses and vaccines, when in liquid form, were kept at −70° C.

LAV2: titre: $10^{3.93}$DICC.sub.50/ml; lyophilized, resuspended in 0.5 ml of PBS (containing $Ca^{2+}$ and $Mg^{2+}$; $CaCl_2.2H_2O$ 0.133 g/l; $MgCl.sub._2.6H_2O$, 0.1 g/l) and administered in totality.

Passage VDV2 DEN2-TV722 (2 plaque purifications+1 amplification): Titre: $10^{5.6}$ DICC$_{50}$/ml; liquid, diluted at $10^{5.3}$ pfu/ml in PBS (containing Ca$^{2+}$ and Mg$^{2+}$; CaCl$_2$.2H$_2$O 0.133 g/l; MgCl$_2$.6H$_2$O, 0.1 g/l); 0.5 ml administered.

Injection was done by SC route in the arm with a 23G1 needle, at a $10^5$ DICC$_{50}$ dose for VDV2.

The results are as presented in Table 11. Titration at day 28 were carried out in triplicate for both PRNT$_{70}$ or and PRNT$_{50}$.

The comparison between VDV2 and LAV2 showed clear differences in viremia, with high viremia of short duration for VDV2 in 3/4 monkeys compared to LAV2, and significant immunogenicity for both types (rather lower for VDV2). This viremia may be considered as too high for VDV2 at this pre-master level after only a few passages on Vero cells. However, wild type DEN-2 (and other types too) induce viremia of longer duration (6 to 7 days) and intensity (up to 5 logs plaque forming units [pfu]) (Monath et al., 2000; Bray et al., 1996).

Viremia and immunogenicity have been measured as usual in CDC by R Kinney. The results are shown in Table 12.

VDV2 passage 11 monovalent vaccine induced a significant immune response, while viremia was low or absent. The absent/low VDV2-induced viremia is to be considered in light of the previous experiment in which the passage 9 VDV2 induced high early viremia. Some evolution between passages 9 and 11 suppressed this high viremia while immunogenicity was maintained. VDV2 therefore constitutes an acceptable candidate.

It is to be noted that in the same experiment, 4 monkeys were vaccinated with a tetravalent formulation involving the same VDV2 passage 11 vaccine; no viremia was detected for VDV1 and VDV2 while VDV3 and VDV4 induced viremia.

Two other experiments involved the administration of VDV2, alone or in combination with the other serotypes.

TABLE 11

VDV2 passage 9 immunogenicity

| | | Neutralizing Antibody Titer | | | | Viremia (PFU/ml in Vero cells) | | | | | | | | | |
|---|---|---|---|---|---|---|---|---|---|---|---|---|---|---|---|
| | | Day (−15) | | Day 28 | | Day | Day | Day | Day | Day | Day | Day | Day | Day | Day |
| Serum | Group | PRNT$_{70}$ | PRNT$_{50}$ | PRNT$_{70}$ | PRNT$_{50}$ | −15 | 2 | 3 | 4 | 5 | 6 | 7 | 8 | 9 | 10 |
| AD 097 | LAV DEN-2 | <10 | <10 | 80/80/160 | 320/160/320 | 0 | 0 | 0 | 0 | 0 | 0 | 5 | 0 | 50 | 20 |
| AC 170 | | <10 | <10 | 160/80/320 | 320/160/640 | 0 | 0 | 0 | 0 | 0 | 5 | 5 | 0 | 0 | 0 |
| AD 677 | | <10 | <10 | 1280/640/2560 | 2560/1280/2560 | 0 | 5 | 0 | 0 | 10 | 50 | 0 | 5 | 0 | 0 |
| AC 182 | | <10 | <10 | 320/320/320 | 640/1280/1280 | 0 | 0 | 5 | 0 | 15 | 5 | 0 | 5 | 0 | 0 |
| AC 658 | VDV DEN-2 | <10 | <10 | 160/160/160 | 320/160/640 | 0 | 550 | 35 | 0 | 0 | 0 | 0 | 0 | 0 | 0 |
| AC 512 | | <10 | <10 | 160/80/160 | 160/160/160 | 0 | 1650 | 35 | 0 | 5 | 0 | 0 | 0 | 0 | 0 |
| AD 608 | | <10 | <10 | 160/320/160 | 320/320/320 | 0 | 1700 | 60 | 100 | 0 | 0 | 0 | 0 | 0 | 0 |
| AD 132 | | <10 | <10 | 80/80/80 | 80/160/160 | 0 | 70 | 10 | 0 | 50 | 10 | 100 | 0 | 0 | 0 |

| Virus | Exp#1 | Exp#2 | Exp#3 |
|---|---|---|---|
| DEN-2 | 60 PFU | 54 PFU | 46 PFU |

4.1.3 Evaluation of Monovalent VDV2 Candidate at Passage 11

As immunogenicity of the vaccines had been tested at the passage 9, a further experiment was designed to test the monovalent passage after two additional passages (passage 10).

Male *Macaca fascicularis* monkeys were used as before, originating from C.R.P. Le Vallon, Ile Maurice (24 monkeys, mean weight 3.4 kg).

Passage 11 VDV2: Batch: Titre: 8.07 log 10 g DICC$_{50}$/ml
Placebo: PBS with Ca$^{2+}$ and Mg$^{2+}$
VDV3: VERO-Derived Vaccine Dengue serotype 3 strain, obtained by sanitization of LAV3 on Vero cells.
VDV4: VERO-Derived Vaccine Dengue serotype 4 strain, obtained by sanitization of LAV4 on Vero cells.
Vaccines were diluted at $10^{5.3}$ DICC$_{50}$/ml in PBS (containing Ca$^{2+}$ and Mg$^{2+}$; CaCl$_2$.2H$_2$O 0.133 g/l; MgCl$_2$.6H$_2$O, 0.1 g/l); 0.5 ml administered by SC route in the arm with a 23G1 needle, corresponding to a dose of $10.^5$ DICC$_{50}$.

In the first one (tetravalent study; 5-log of each serotype), no viremia was detected for VDV2, and VDV1, while high levels of viremia were detected for VDV3 and VDV4.

In the second experiment, VDV2 passage 11 was administered alone or within a tetravalent combination including VDV1. When administered alone, VDV2 passage 11 induced a low viremia (peak 40) in only 1 out of 4 monkeys while the 3 others were negative. When present within tetravalent formulations, VDV2 induced no or dramatically lower viremia than VDV3 and VDV4, even though VDV2 was administered at 4 log while VDV3 and VDV4 were administered at 2 log. This demonstrates the higher safety of VDV2, as far as viremia is concerned. Monovalent VDV2 thus fulfilled the success criteria initially defined in monkeys.

TABLE 12 passage 11 VDV2 immunogenicity and viremia

| | | Neutralizing Antibody Titer | |

TABLE 13

Flow chart for follow up

| Visit Number | V 01 | V 02 | V 03 | V 04 | V 05 | V 06 | V 07 | V 08 | V 09 | V 10 | V 11 | V 12 |
|---|---|---|---|---|---|---|---|---|---|---|---|---|
| Trial timelines¤ | D 0 | D 2 | D 4 | D 6 | D 8 | D 10 | D 12 | D 14 | D 16 | D 28 | D 180 | D 365 |
| Time Windows | | | | | | ±1 d | ±1 d | | | ±4 d | ±15 d | ±30 d |
| Clinical Examination | ✓ | ✓ | ✓ | ✓ | ✓ | ✓ | ✓ | ✓ | ✓ | ✓ | ✓ | ✓ |
| Vital signs (BP, pulse rate) | ✓ | | | | | | | | | | | |
| Oral temperature | ✓ | ✓ | ✓ | ✓ | ✓ | ✓ | ✓ | ✓ | ✓ | ✓ | | |
| Blood Sampling: | | | | | | | | | | | | |
| Serology HBV/HCV/HIV | ✓ | | ✓ | | ✓ | | ✓ | | ✓ | ✓ | | |
| Biological Safety | ✓ | ✓ | ✓ | ✓ | ✓ | ✓ | ✓ | ✓ | ✓ | | | |
| Viremia | ✓ | | | | | | | | ✓ | ✓ | ✓ | ✓ |
| Immunogenicity | ✓ | ✓ | ✓ | ✓ | ✓ | ✓ | ✓ | ✓ | ✓ | ✓ | | |
| Cytokines in serum | ✓ | | | | | | | | | ✓ | | |
| PBMCs for T cell (subset) | ✓ | | | | | | | | | ✓ | | |
| immediate surveillance | ✓ | | | | | | | | | | | |
| Local & systemic events | ✓ | ✓ | ✓ | ✓ | ✓ | ✓ | ✓ | ✓ | ✓ | ✓ | ✓ | ✓ |

V: visit D: day

¤ Time intervals between visits will be calculated from the date of study vaccination which might differ from the date of visit (e.g. in case a temporary exclusion criterion is met). V 06 and V 07 must be done with at least 1-day interval.

The products tested are:

The vaccine evaluated is a lyophilised product in a vial that is reconstituted extemporaneously with the diluent provided separately:

Active ingredient: 4±0.5 $\log_{10}$ $CCID_{50}$ of monovalent Vero dengue virus serotype 2 (VDV2 passage 11) per 0.5 mL dose;

Diluent: Sterile NaCl .sup.4‰ solution for vaccine reconstitution.

The reconstituted vaccine, i.e 0.5 mL of NaCl 4‰ solution of monovalent VDV2, should be used immediately or be maintained until use +2° C. and +8° C.

The 0.5 mL vaccine dose is administered subcutaneously in the deltoid region.

The control vaccine Stamaril®, is a yellow fever vaccine produced by Aventis Pasteur. Stamaril.RTM. is presented as a lyophilised, avian-leukosis-free, stabilised product to be reconstituted with a diluent immediately before use. (Active ingredient: Live attenuated yellow fever virus (17D strain): .gtoreq.1,000 mouse Lethal Dose 50% ($LD_{50}$)/Diluent: Sterile NaCl 4‰ solution).

The control vaccine is administered subcutaneously in the deltoid region.

No subject had clinically significant syndrome related to vaccination. One subject had a transient fever (<38° C.). One subject had a local reaction (induration). No serious adverse event related to vaccination was observed.

All subjects have antibodies response 28 days after vaccination against dengue 2 (titer between 1888 and 6393)

REFERENCES

The following references are incorporated herein by reference as if set forth in their entirety herein:

Bhamarapravati, N and Yoksan S. (1997). Dengue and Dengue Hemorrhagic Fever.Live attenuated tetravalent dengue vaccines, CABI Publishing, 367-379.

Burke D S and Monath T P. Flaviviruses (2001) In Knipe D M and Howley P M, eds. Fields Virology 4th ed. Vol 1, 1043-1125

DeFraites R F, Smoak B L, Trofa A F, Hoke C H, Kanesathasan N, King A, MacArthy P O, et al. Dengue fever among U.S. military personnel—Haiti, September-November, 1994. MMWR 1994; 43: 845-848.

Dunnen and Antonarakis (2000) Mutation nomenclature extensions and suggestions to describe complex mutations: a discussion. Hum Mutation. 15:7-12; Erratum in: Hum Mutat 2002; 20(5):403

Gubler D J. Dengue. (1988) In: Epidemiology of arthropod-borne viral disease. Monath T P M, editor, Boca Raton (Fla.): CRC Press:223-60

Gubler D J, Kuno G. Dengue and Dengue Hemorrhagic Fever. CAB International Publishing 1997

Gubler D. Epidemic dengue/dengue hemorrhagic fever as a public health, social and economic problem in the 21st century. (2002) TRENDS in Microbiology. 10:100-103

Halstead S B and Simasthien P (1970). Observations related to pathogenesis of Dengue haemorrhagic fever. II. Antigenic and biological properties of dengue viruses and their association with disease response in the host. Yale J. Biol. Med; 42: 261-275.

Huang et al. (2000). J. Virol 74; 3020-3028.

Jirakanjanakit N, Khin M M, Yoksan S, Bhamarapravati N. (1999) Dynamics of susceptibility and transmissibility of the live, attenuated, candidate vaccines dengue-1 PDK13, dengue-3 PGMK30F3, and dengue-4 PDK48 after oral infection in Aedes aegypti. Am J Trop Med Hyg., 61(4):672-676

Kautner I, Robinson M J, Kubnle U. (1997) Dengue Virus infection: Epidemiology, pathogenesis, clinical presentation, diagnosis, and prevention. J of Pediatrics; 131:516-524

Monath, T P. (1994) Dengue: the risk to developed and developing countries. Proc Natl Acad Sci; 91: 2395-2400.

Monath T P, Levenbook I, Soike K, Zhang Z X, Ratterree M, Draper K et al. (2000) Chimeric yellow fever virus 17D-Japanese encephalitis virus vaccine: dose-response effectiveness and extended safety testing in rhesus monkeys. Journal of Virology; 74(4):1742-1751

Bray M, Men R, Lai C J. (1996) Monkeys immunized with intertypic chimeric dengue viruses are protected against wild-type virus challenge. J Virol; 70(6):4162-4166

Rigau-Perez J G, Clark G G, Gubler D J, Reiter P, Sanders E J, Vorndam A V. (1998) Dengue and dengue haemorrhagic fever. Lancet; 352: 971-977.

Rothman A L, Ennis F A. (1999) Immunopathogenesis of dengue hemorrhagic fever. Virology; 257: 1-6

Sabin A B. (1952) Research on dengue during World War II. Am J Trop Med Hyg; 1: 30-50

Shirtcliffe P, Cameron E, Nicholson K G, Wiselka M J. (1998) Don't forget dengue! Clinical features of dengue fever in returning travellers. J Roy Coll Phys Lond.; 32: 235-237.

Thompson J D, Higgins D G, and Gibson T J. (1994) CLUSTAL W: improving the sensitivity of progressive multiple sequence alignment through sequence weighting, position-specific gap penalties and weight matrix choice. Nucl. Acids. Res., 22 (22), 4673-4680

Vaughn D W, Green S, Kalayanarooj S, Innis B L, Nimmannitya S, Suntayakorn S, Rothman A L, Ennis F A, Nisalak A. (1997) Dengue in the early febrile phase: viremia and antibody response. J Infect Dis; 176: 322-30.

Vaughn D W, Green S, Kalayanarooj S, Innis B L, Nimmannitya S, Suntayakorn S, Endy T P, Raengsakulrach B, Rothman A L, Ennis F A, Nisalak A. (2000) Dengue viremia titer, antibody response pattern, and virus serotype correlate with disease severity. J Inf Dis; 181: 2-9.

WHO Technical Guide, 1986. Dengue haemorrhagic fever: diagnosis, treatment and control, p 1-2. World Health Organization, Geneva, Switzerland Wu S, Grouard-Vogel G, Sun W, Mascola J, Brachtel E, Putvatana R. (2000) Human skin Langerhans cells are targets of dengue virus infection. Nature Med; 7:816-820

Khin M M, Jirakanjanakit N, Yoksan S, Bhamarapravati N. (1994) Infection, dissemination, transmission, and biological attributes of dengue-2 PDK53 candidate vaccine virus after oral infection in *Aedes aegypti*. Am J Trop Med Hyg.,51(6): 864-869

---

What is claimed is:

1. A fragment of a polyprotein encoded by SEQ ID NO: 1, wherein the fragment comprises envelope (E) protein which comprises a glutamic acid at position 228 of the E protein.

2. The fragment of claim 1, wherein the polyprotein is the polyprotein of sequence SEQ ID NO: 2.

3. A live attenuated dengue-2 virus strain comprising the fragment of claim 1.

4. The live attenuated dengue-2 virus strain of claim 3, further comprising a fragment of a polyprotein encoded by SEQ ID NO: 1, wherein the fragment comprises membrane (M) protein which comprises an arginine at position 9 of the M protein.

5. An immunogenic composition comprising the live attenuated dengue-2 virus strain of claim 3.

6. The immunogenic composition of claim 5, further comprising a live attenuated dengue virus of a serotype other than dengue-2 virus.

7. The immunogenic composition of claim 5, further comprising a live attenuated dengue virus of serotype 1, serotype 3, and serotype 4.

* * * * *

SEQUENCE LISTING

```
<160> NUMBER OF SEQ ID NOS: 42

<210> SEQ ID NO 1
<211> LENGTH: 10723
<212> TYPE: DNA
<213> ORGANISM: Dengue virus
<220> FEATURE:
<221> NAME/KEY: misc_feature
<222> LOCATION: (1)..(10723)
<223> OTHER INFORMATION: VDV2
<220> FEATURE:
<221> NAME/KEY: CDS
<222> LOCATION: (97)..(10272)
<220> FEATURE:
<221> NAME/KEY: misc_feature
<222> LOCATION: (10361)..(10361)
<223> OTHER INFORMATION: unknown

<400> SEQUENCE: 1
agttgttagt ctacgtggac cgacaaagac agattctttg agggagctaa gctcaatgta       60
gttctaacag ttttttaatt agagagcaga tctctg atg aat aac caa cgg aaa       114
                                       Met Asn Asn Gln Arg Lys
                                        1               5 aag gcg aaa aac acg cct ttc aat atg ctg aaa cgc gag aga aac cgc       162
Lys Ala Lys Asn Thr Pro Phe Asn Met Leu Lys Arg Glu Arg Asn Arg
         10                  15                  20 gtg tcg act gtg caa cag ctg aca aag aga ttc tca ctt gga atg ctg       210
Val Ser Thr Val Gln Gln Leu Thr Lys Arg Phe Ser Leu Gly Met Leu
     25                  30                  35 cag gga cga gga cca tta aaa ctg ttc atg gcc ctg gtg gcg ttc ctt       258
Gln Gly Arg Gly Pro Leu Lys Leu Phe Met Ala Leu Val Ala Phe Leu
 40                  45                  50 cgt ttc cta aca atc cca cca aca gca ggg ata ttg aag aga tgg gga       306
Arg Phe Leu Thr Ile Pro Pro Thr Ala Gly Ile Leu Lys Arg Trp Gly
55                  60                  65                  70 aca att aaa aaa tca aaa gct att aat gtt ttg aga ggg ttc agg aaa       354
Thr Ile Lys Lys Ser Lys Ala Ile Asn Val Leu Arg Gly Phe Arg Lys
                 75                  80                  85 gag att gga agg atg ctg aac atc ttg aat agg aga cgc aga tct gca       402
Glu Ile Gly Arg Met Leu Asn Ile Leu Asn Arg Arg Arg Arg Ser Ala
             90                  95                 100 ggc atg atc att atg ctg att cca aca gtg atg gcg ttc cat tta acc       450
Gly Met Ile Ile Met Leu Ile Pro Thr Val Met Ala Phe His Leu Thr
        105                 110                 115 aca cgt aac gga gaa cca cac atg atc gtc agc aga caa gag aaa ggg       498
Thr Arg Asn Gly Glu Pro His Met Ile Val Ser Arg Gln Glu Lys Gly
    120                 125                 130 aaa agt ctt ctg ttt aaa aca gag gtt ggc gtg aac atg tgt acc ctc       546
Lys Ser Leu Leu Phe Lys Thr Glu Val Gly Val Asn Met Cys Thr Leu
```

|     |     |
| --- | --- |
| 135 140 145 150 | |
| atg gcc atg gac ctt ggt gaa ttg tgt gaa gac aca atc acg tac aag<br>Met Ala Met Asp Leu Gly Glu Leu Cys Glu Asp Thr Ile Thr Tyr Lys<br>155 160 165 | 594 |
| tgt ccc ctt ctc agg cag aat gag cca gaa gac ata gac tgt tgg tgc<br>Cys Pro Leu Leu Arg Gln Asn Glu Pro Glu Asp Ile Asp Cys Trp Cys<br>170 175 180 | 642 |
| aac tct acg tcc acg tgg gta act tat ggg acg tgt acc acc atg gga<br>Asn Ser Thr Ser Thr Trp Val Thr Tyr Gly Thr Cys Thr Thr Met Gly<br>185 190 195 | 690 |
| gaa cat aga aga gaa aaa aga tca gtg gca ctc gtt cca cat gtg cga<br>Glu His Arg Arg Glu Lys Arg Ser Val Ala Leu Val Pro His Val Arg<br>200 205 210 | 738 |
| atg gga ctg gag aca cga act gaa aca tgg atg tca tca gaa ggg gcc<br>Met Gly Leu Glu Thr Arg Thr Glu Thr Trp Met Ser Ser Glu Gly Ala<br>215 220 225 230 | 786 |
| tgg aaa cat gtc cag aga att gaa act tgg atc ttg aga cat cca ggc<br>Trp Lys His Val Gln Arg Ile Glu Thr Trp Ile Leu Arg His Pro Gly<br>235 240 245 | 834 |
| ttc acc atg atg gca gca atc ctg gca tac acc ata gga acg aca cat<br>Phe Thr Met Met Ala Ala Ile Leu Ala Tyr Thr Ile Gly Thr Thr His<br>250 255 260 | 882 |
| ttc caa aga gcc ctg att ttc atc tta ctg aca gct gtc act cct tca<br>Phe Gln Arg Ala Leu Ile Phe Ile Leu Leu Thr Ala Val Thr Pro Ser<br>265 270 275 | 930 |
| atg aca atg cgt tgc ata gga atg tca aat aga gac ttt gtg gaa ggg<br>Met Thr Met Arg Cys Ile Gly Met Ser Asn Arg Asp Phe Val Glu Gly<br>280 285 290 | 978 |
| gtt tca gga gga agc tgg gtt gac ata gtc tta gaa cat gga agc tgt<br>Val Ser Gly Gly Ser Trp Val Asp Ile Val Leu Glu His Gly Ser Cys<br>295 300 305 310 | 1026 |
| gtg acg acg atg gca aaa aac aaa cca aca ttg gat ttt gaa ctg ata<br>Val Thr Thr Met Ala Lys Asn Lys Pro Thr Leu Asp Phe Glu Leu Ile<br>315 320 325 | 1074 |
| aaa aca gaa gcc aaa cag cct gcc acc cta agg aag tac tgt ata gag<br>Lys Thr Glu Ala Lys Gln Pro Ala Thr Leu Arg Lys Tyr Cys Ile Glu<br>330 335 340 | 1122 |
| gca aag cta acc aac aca aca aca gaa tct cgc tgc cca aca caa ggg<br>Ala Lys Leu Thr Asn Thr Thr Thr Glu Ser Arg Cys Pro Thr Gln Gly<br>345 350 355 | 1170 |
| gaa ccc agc cta aat gaa gag cag gac aaa agg ttc gtc tgc aaa cac<br>Glu Pro Ser Leu Asn Glu Glu Gln Asp Lys Arg Phe Val Cys Lys His<br>360 365 370 | 1218 |
| tcc atg gta gac aga gga tgg gga aat gga tgt gga cta ttt gga aag<br>Ser Met Val Asp Arg Gly Trp Gly Asn Gly Cys Gly Leu Phe Gly Lys<br>375 380 385 390 | 1266 |
| gga ggc att gtg acc tgt gct atg ttc aga tgc aaa aag aac atg gaa<br>Gly Gly Ile Val Thr Cys Ala Met Phe Arg Cys Lys Lys Asn Met Glu<br>395 400 405 | 1314 |
| gga aaa gtt gtg caa cca gaa aac ttg gaa tac acc att gtg ata aca<br>Gly Lys Val Val Gln Pro Glu Asn Leu Glu Tyr Thr Ile Val Ile Thr<br>410 415 420 | 1362 |
| cct cac tca ggg gaa gag cat gca gtc gga aat gac aca gga aaa cat<br>Pro His Ser Gly Glu Glu His Ala Val Gly Asn Asp Thr Gly Lys His<br>425 430 435 | 1410 |
| ggc aag gaa atc aaa ata aca cca cag agt tcc atc aca gaa gca gaa<br>Gly Lys Glu Ile Lys Ile Thr Pro Gln Ser Ser Ile Thr Glu Ala Glu<br>440 445 450 | 1458 |
| ttg aca ggt tat ggc act gtc aca atg gag tgc tct cca aga acg ggc<br>Leu Thr Gly Tyr Gly Thr Val Thr Met Glu Cys Ser Pro Arg Thr Gly | 1506 |

```
Leu Thr Gly Tyr Gly Thr Val Thr Met Glu Cys Ser Pro Arg Thr Gly
455                 460                 465                 470 ctc gac ttc aat gag atg gtg ttg ctg cag atg gaa aat aaa gct tgg      1554
Leu Asp Phe Asn Glu Met Val Leu Leu Gln Met Glu Asn Lys Ala Trp
                475                 480                 485 ctg gtg cac agg caa tgg ttc cta gac ctg ccg tta cca tgg ttg ccc      1602
Leu Val His Arg Gln Trp Phe Leu Asp Leu Pro Leu Pro Trp Leu Pro
                490                 495                 500 gga gcg gac aca caa gag tca aat tgg ata cag aag gag aca ttg gtc      1650
Gly Ala Asp Thr Gln Glu Ser Asn Trp Ile Gln Lys Glu Thr Leu Val
                505                 510                 515 act ttc aaa aat ccc cat gcg aag aaa cag gat gtt gtt gtt tta gga      1698
Thr Phe Lys Asn Pro His Ala Lys Lys Gln Asp Val Val Val Leu Gly
                520                 525                 530 tcc caa gaa ggg gcc atg cac aca gca ctt aca ggg gcc aca gaa atc      1746
Ser Gln Glu Gly Ala Met His Thr Ala Leu Thr Gly Ala Thr Glu Ile
535                 540                 545                 550 caa atg tca tca gga aac tta ctc ttc aca gga cat ctc aag tgc agg      1794
Gln Met Ser Ser Gly Asn Leu Leu Phe Thr Gly His Leu Lys Cys Arg
                555                 560                 565 ctg aga atg gac aag cta cag ctc aaa gga atg tca tac tct atg tgc      1842
Leu Arg Met Asp Lys Leu Gln Leu Lys Gly Met Ser Tyr Ser Met Cys
                570                 575                 580 aca gga aag ttt aaa gtt gtg aag gaa ata gca gaa aca caa cat gga      1890
Thr Gly Lys Phe Lys Val Val Lys Glu Ile Ala Glu Thr Gln His Gly
                585                 590                 595 aca ata gtt atc aga gtg caa tat gaa ggg gac ggc tct cca tgc aag      1938
Thr Ile Val Ile Arg Val Gln Tyr Glu Gly Asp Gly Ser Pro Cys Lys
600                 605                 610 atc cct ttt gag ata atg gat ttg gaa aaa aga cat gtc tta ggt cgc      1986
Ile Pro Phe Glu Ile Met Asp Leu Glu Lys Arg His Val Leu Gly Arg
615                 620                 625                 630 ctg att aca gtc aac cca att gtg aca gaa aaa gat agc cca gtc aac      2034
Leu Ile Thr Val Asn Pro Ile Val Thr Glu Lys Asp Ser Pro Val Asn
                635                 640                 645 ata gaa gca gaa cct cca ttt gga gac agc tac atc atc ata gga gta      2082
Ile Glu Ala Glu Pro Pro Phe Gly Asp Ser Tyr Ile Ile Ile Gly Val
                650                 655                 660 gag ccg gga caa ctg aag ctc aac tgg ttt aag aaa gga agt tct atc      2130
Glu Pro Gly Gln Leu Lys Leu Asn Trp Phe Lys Lys Gly Ser Ser Ile
                665                 670                 675 ggc caa atg ttt gag aca aca atg agg ggg gcg aag aga atg gcc att      2178
Gly Gln Met Phe Glu Thr Thr Met Arg Gly Ala Lys Arg Met Ala Ile
680                 685                 690 tta ggt gac aca gcc tgg gat ttt gga tcc ttg gga gga gtg ttt aca      2226
Leu Gly Asp Thr Ala Trp Asp Phe Gly Ser Leu Gly Gly Val Phe Thr
695                 700                 705                 710 tct ata gga aag gct ctc cac caa gtc ttt gga gca atc tat gga gct      2274
Ser Ile Gly Lys Ala Leu His Gln Val Phe Gly Ala Ile Tyr Gly Ala
                715                 720                 725 gcc ttc agt ggg gtt tca tgg act atg aaa atc ctc ata gga gtc att      2322
Ala Phe Ser Gly Val Ser Trp Thr Met Lys Ile Leu Ile Gly Val Ile
                730                 735                 740 atc aca tgg ata gga atg aat tca cgc agc acc tca ctg tct gtg aca      2370
Ile Thr Trp Ile Gly Met Asn Ser Arg Ser Thr Ser Leu Ser Val Thr
                745                 750                 755 cta gta ttg gtg gga att gtg aca ctg tat ttg gga gtc atg gtg cag      2418
Leu Val Leu Val Gly Ile Val Thr Leu Tyr Leu Gly Val Met Val Gln
760                 765                 770
```

-continued

```
gcc gat agt ggt tgc gtt gtg agc tgg aaa aac aaa gaa ctg aaa tgt    2466
Ala Asp Ser Gly Cys Val Val Ser Trp Lys Asn Lys Glu Leu Lys Cys
775             780                 785                 790 ggc agt ggg att ttc atc aca gac aac gtg cac aca tgg aca gaa caa    2514
Gly Ser Gly Ile Phe Ile Thr Asp Asn Val His Thr Trp Thr Glu Gln
        795                 800                 805 tac aaa ttc caa cca gaa tcc cct tca aaa cta gct tca gct atc cag    2562
Tyr Lys Phe Gln Pro Glu Ser Pro Ser Lys Leu Ala Ser Ala Ile Gln
810                 815                 820 aaa gcc cat gaa gag gac att tgt gga atc cgc tca gta aca aga ctg    2610
Lys Ala His Glu Glu Asp Ile Cys Gly Ile Arg Ser Val Thr Arg Leu
    825                 830                 835 gag aat ctg atg tgg aaa caa ata aca cca gaa ttg aat cac att cta    2658
Glu Asn Leu Met Trp Lys Gln Ile Thr Pro Glu Leu Asn His Ile Leu
840                 845                 850 tca gaa aat gag gtg aag tta act att atg aca gga gac atc aaa gga    2706
Ser Glu Asn Glu Val Lys Leu Thr Ile Met Thr Gly Asp Ile Lys Gly
855                 860                 865                 870 atc atg cag gca gga aaa cga tct ctg cgg cct cag ccc act gag ctg    2754
Ile Met Gln Ala Gly Lys Arg Ser Leu Arg Pro Gln Pro Thr Glu Leu
            875                 880                 885 aag tat tca tgg aaa aca tgg ggc aaa gca aaa atg ctc tct aca gag    2802
Lys Tyr Ser Trp Lys Thr Trp Gly Lys Ala Lys Met Leu Ser Thr Glu
                890                 895                 900 tct cat aac cag acc ttt ctc att gat ggc ccc gaa aca gca gaa tgc    2850
Ser His Asn Gln Thr Phe Leu Ile Asp Gly Pro Glu Thr Ala Glu Cys
    905                 910                 915 ccc aac aca aat aga gct tgg aat tcg ttg gaa gtt gaa gac tat ggc    2898
Pro Asn Thr Asn Arg Ala Trp Asn Ser Leu Glu Val Glu Asp Tyr Gly
920                 925                 930 ttt gga gta ttc acc acc aat ata tgg cta aaa ttg aaa gaa aaa cag    2946
Phe Gly Val Phe Thr Thr Asn Ile Trp Leu Lys Leu Lys Glu Lys Gln
935                 940                 945                 950 gat gta ttc tgc gac tca aaa ctc atg tca gcg gcc ata aaa gac aac    2994
Asp Val Phe Cys Asp Ser Lys Leu Met Ser Ala Ala Ile Lys Asp Asn
            955                 960                 965 aga gcc gtc cat gcc gat atg ggt tat tgg ata gaa agt gca ctc aat    3042
Arg Ala Val His Ala Asp Met Gly Tyr Trp Ile Glu Ser Ala Leu Asn
                970                 975                 980 gac aca tgg aag ata gag aaa gcc tct ttc att gaa gtt aaa aac tgc    3090
Asp Thr Trp Lys Ile Glu Lys Ala Ser Phe Ile Glu Val Lys Asn Cys
    985                 990                 995 cac tgg  cca aaa tca cac acc  ctc tgg agc aat gga  gtg cta gaa      3135
His Trp  Pro Lys Ser His Thr  Leu Trp Ser Asn Gly  Val Leu Glu
1000                 1005                 1010 agt gag  atg ata att cca aag  aat ctc gct gga cca  gtg tct caa      3180
Ser Glu  Met Ile Ile Pro Lys  Asn Leu Ala Gly Pro  Val Ser Gln
1015                 1020                 1025 cac aac  tat aga cca ggc tac  cat aca caa ata aca  gga cca tgg      3225
His Asn  Tyr Arg Pro Gly Tyr  His Thr Gln Ile Thr  Gly Pro Trp
1030                 1035                 1040 cat cta  ggt aag ctt gag atg  gac ttt gat ttc tgt  gat gga aca      3270
His Leu  Gly Lys Leu Glu Met  Asp Phe Asp Phe Cys  Asp Gly Thr
1045                 1050                 1055 aca gtg  gta gtg act gag gac  tgc gga aat aga gga  ccc tct ttg      3315
Thr Val  Val Val Thr Glu Asp  Cys Gly Asn Arg Gly  Pro Ser Leu
1060                 1065                 1070 aga aca  acc act gcc tct gga  aaa ctc ata aca gaa  tgg tgc tgc      3360
Arg Thr  Thr Thr Ala Ser Gly  Lys Leu Ile Thr Glu  Trp Cys Cys
1075                 1080                 1085
```

-continued

| | | | | | | | | | | | | |
|---|---|---|---|---|---|---|---|---|---|---|---|---|
| cga | tct | tgc | aca | tta | cca | ccg | cta | aga | tac | aga | ggt | gag | gat | ggg | 3405 |
| Arg | Ser | Cys | Thr | Leu | Pro | Pro | Leu | Arg | Tyr | Arg | Gly | Glu | Asp | Gly | |
| | 1090 | | | | 1095 | | | | | 1100 | | | | | |

```
cga tct tgc aca tta cca ccg cta aga tac aga ggt gag gat ggg    3405
Arg Ser Cys Thr Leu Pro Pro Leu Arg Tyr Arg Gly Glu Asp Gly
    1090            1095                1100 tgc tgg tac ggg atg gaa atc aga cca ttg aag gag aaa gaa gag    3450
Cys Trp Tyr Gly Met Glu Ile Arg Pro Leu Lys Glu Lys Glu Glu
1105            1110                1115 aat ttg gtc aac tcc ttg gtc aca gct gga cat ggg cag gtc gac    3495
Asn Leu Val Asn Ser Leu Val Thr Ala Gly His Gly Gln Val Asp
    1120            1125                1130 aac ttt tca cta gga gtc ttg gga atg gca ttg ttc ctg gag gaa    3540
Asn Phe Ser Leu Gly Val Leu Gly Met Ala Leu Phe Leu Glu Glu
1135            1140                1145 atg ctt agg acc cga gta gga acg aaa cat gca ata cta cta gtt    3585
Met Leu Arg Thr Arg Val Gly Thr Lys His Ala Ile Leu Leu Val
    1150            1155                1160 gca gtt tct ttt gtg aca ttg atc aca ggg aac atg tcc ttt aga    3630
Ala Val Ser Phe Val Thr Leu Ile Thr Gly Asn Met Ser Phe Arg
1165            1170                1175 gac ctg gga aga gtg atg gtt atg gta ggc gcc act atg acg gat    3675
Asp Leu Gly Arg Val Met Val Met Val Gly Ala Thr Met Thr Asp
    1180            1185                1190 gac ata ggt atg ggc gtg act tat ctt gcc cta cta gca gcc ttc    3720
Asp Ile Gly Met Gly Val Thr Tyr Leu Ala Leu Leu Ala Ala Phe
1195            1200                1205 aaa gtc aga cca act ttt gca gct gga cta ctc ttg aga aag ctg    3765
Lys Val Arg Pro Thr Phe Ala Ala Gly Leu Leu Leu Arg Lys Leu
    1210            1215                1220 acc tcc aag gaa ttg atg atg act act ata gga att gta ctc ctc    3810
Thr Ser Lys Glu Leu Met Met Thr Thr Ile Gly Ile Val Leu Leu
1225            1230                1235 tcc cag agc acc ata cca gag acc att ctt gag ttg act gat gcg    3855
Ser Gln Ser Thr Ile Pro Glu Thr Ile Leu Glu Leu Thr Asp Ala
    1240            1245                1250 tta gcc tta ggc atg atg gtc ctc aaa atg gtg aga aat atg gaa    3900
Leu Ala Leu Gly Met Met Val Leu Lys Met Val Arg Asn Met Glu
1255            1260                1265 aag tat caa ttg gca gtg act atc atg gct atc ttg tgc gtc cca    3945
Lys Tyr Gln Leu Ala Val Thr Ile Met Ala Ile Leu Cys Val Pro
    1270            1275                1280 aac gca gtg ata tta caa aac gca tgg aaa gtg agt tgc aca ata    3990
Asn Ala Val Ile Leu Gln Asn Ala Trp Lys Val Ser Cys Thr Ile
1285            1290                1295 ttg gca gtg gtg tcc gtt tcc cca ctg ttc tta aca tcc tca cag    4035
Leu Ala Val Val Ser Val Ser Pro Leu Phe Leu Thr Ser Ser Gln
    1300            1305                1310 caa aaa aca gat tgg ata cca tta gca ttg acg atc aaa ggt ctc    4080
Gln Lys Thr Asp Trp Ile Pro Leu Ala Leu Thr Ile Lys Gly Leu
1315            1320                1325 aat cca aca gct att ttt cta aca acc ctc tca aga acc agc aag    4125
Asn Pro Thr Ala Ile Phe Leu Thr Thr Leu Ser Arg Thr Ser Lys
    1330            1335                1340 aaa agg agc tgg cca tta aat gag gct atc atg gca gtc ggg atg    4170
Lys Arg Ser Trp Pro Leu Asn Glu Ala Ile Met Ala Val Gly Met
1345            1350                1355 gtg agc att tta gcc agt tct ctc cta aaa aat gat att ccc atg    4215
Val Ser Ile Leu Ala Ser Ser Leu Leu Lys Asn Asp Ile Pro Met
    1360            1365                1370 aca gga cca tta gtg gct gga ggg ctc ctc act gtg tgc tac gtg    4260
Thr Gly Pro Leu Val Ala Gly Gly Leu Leu Thr Val Cys Tyr Val
1375
```

-continued

```
                1375                1380                1385
ctc act gga cga tcg gcc gat ttg gaa ctg gag aga gca gcc gat     4305
Leu Thr Gly Arg Ser Ala Asp Leu Glu Leu Glu Arg Ala Ala Asp
    1390                1395                1400 gtc aaa tgg gaa gac cag gca gag ata tca gga agc agt cca atc     4350
Val Lys Trp Glu Asp Gln Ala Glu Ile Ser Gly Ser Ser Pro Ile
1405                1410                1415 ctg tca ata aca ata tca gaa gat ggt agc atg tcg ata aaa aat     4395
Leu Ser Ile Thr Ile Ser Glu Asp Gly Ser Met Ser Ile Lys Asn
    1420                1425                1430 gaa gag gaa gaa caa aca ctg acc ata ctc att aga aca gga ttg     4440
Glu Glu Glu Glu Gln Thr Leu Thr Ile Leu Ile Arg Thr Gly Leu
1435                1440                1445 ctg gtg atc tca gga ctt ttt cct gta tca ata cca atc acg gca     4485
Leu Val Ile Ser Gly Leu Phe Pro Val Ser Ile Pro Ile Thr Ala
    1450                1455                1460 gca gca tgg tac ctg tgg gaa gtg aag aaa caa cgg gcc gga gta     4530
Ala Ala Trp Tyr Leu Trp Glu Val Lys Lys Gln Arg Ala Gly Val
1465                1470                1475 ttg tgg gat gtt cct tca ccc cca ccc atg gga aag gct gaa ctg     4575
Leu Trp Asp Val Pro Ser Pro Pro Pro Met Gly Lys Ala Glu Leu
    1480                1485                1490 gaa gat gga gcc tat aga att aag caa aaa ggg att ctt gga tat     4620
Glu Asp Gly Ala Tyr Arg Ile Lys Gln Lys Gly Ile Leu Gly Tyr
1495                1500                1505 tcc cag atc gga gcc gga gtt tac aaa gaa gga aca ttc cat aca     4665
Ser Gln Ile Gly Ala Gly Val Tyr Lys Glu Gly Thr Phe His Thr
    1510                1515                1520 atg tgg cat gtc aca cgt ggc gct gtt cta atg cat aaa gga aag     4710
Met Trp His Val Thr Arg Gly Ala Val Leu Met His Lys Gly Lys
1525                1530                1535 agg att gaa cca aca tgg gcg gac gtc aag aaa gac cta ata tca     4755
Arg Ile Glu Pro Thr Trp Ala Asp Val Lys Lys Asp Leu Ile Ser
    1540                1545                1550 tat gga gga ggc tgg aag tta gaa gga gaa tgg aag gaa gga gaa     4800
Tyr Gly Gly Gly Trp Lys Leu Glu Gly Glu Trp Lys Glu Gly Glu
1555                1560                1565 gaa gtc cag gta ttg gca ctg gag cct gga aaa aat cca aga gcc     4845
Glu Val Gln Val Leu Ala Leu Glu Pro Gly Lys Asn Pro Arg Ala
    1570                1575                1580 gtc caa acg aaa cct ggt ctt ttc aaa acc aac gcc gga aca ata     4890
Val Gln Thr Lys Pro Gly Leu Phe Lys Thr Asn Ala Gly Thr Ile
1585                1590                1595 ggt gct gta tct ctg gac ttt tct cct gga acg tca gga tct cca     4935
Gly Ala Val Ser Leu Asp Phe Ser Pro Gly Thr Ser Gly Ser Pro
    1600                1605                1610 att atc gac aaa aaa gga aaa gtt gtg ggt ctt tat ggt aat ggt     4980
Ile Ile Asp Lys Lys Gly Lys Val Val Gly Leu Tyr Gly Asn Gly
1615                1620                1625 gtt gtt aca agg agt gga gca tat gtg agt gct ata gcc cag act     5025
Val Val Thr Arg Ser Gly Ala Tyr Val Ser Ala Ile Ala Gln Thr
    1630                1635                1640 gaa aaa agc att gaa gac aac cca gag atc gaa gat cac att ttc     5070
Glu Lys Ser Ile Glu Asp Asn Pro Glu Ile Glu Asp His Ile Phe
1645                1650                1655 cga aag aga aga ctg acc atc atg gac ctc cac cca gga gcg gga     5115
Arg Lys Arg Arg Leu Thr Ile Met Asp Leu His Pro Gly Ala Gly
    1660                1665                1670 aag acg aag aga tac ctt ccg gcc ata gtc aga gaa gct ata aaa     5160
Lys Thr Lys Arg Tyr Leu Pro Ala Ile Val Arg Glu Ala Ile Lys
```

```
             Lys Thr Lys Arg Tyr Leu Pro Ala Ile Val Arg Glu Ala Ile Lys
             1675                1680                1685 cgg ggt ttg aga aca tta atc ttg gcc ccc act aga gtt gtg gca               5205
Arg Gly Leu Arg Thr Leu Ile Leu Ala Pro Thr Arg Val Val Ala
1690                1695                1700 gct gaa atg gag gaa gcc ctt aga gga ctt cca ata aga tac cag               5250
Ala Glu Met Glu Glu Ala Leu Arg Gly Leu Pro Ile Arg Tyr Gln
1705                1710                1715 acc cca gcc atc aga gct gag cac acc ggg cgg gag att gtg gac               5295
Thr Pro Ala Ile Arg Ala Glu His Thr Gly Arg Glu Ile Val Asp
1720                1725                1730 cta atg tgt cat gcc aca ttt acc atg agg ctg cta tca cca gtt               5340
Leu Met Cys His Ala Thr Phe Thr Met Arg Leu Leu Ser Pro Val
1735                1740                1745 aga gtg cca aac tac aac ctg att atc atg gac gaa gcc cat ttc               5385
Arg Val Pro Asn Tyr Asn Leu Ile Ile Met Asp Glu Ala His Phe
1750                1755                1760 aca gac cca gca agt ata gca gct aga gga tac atc tca act cga               5430
Thr Asp Pro Ala Ser Ile Ala Ala Arg Gly Tyr Ile Ser Thr Arg
1765                1770                1775 gtg gag atg ggt gag gca gct ggg att ttt atg aca gcc act ccc               5475
Val Glu Met Gly Glu Ala Ala Gly Ile Phe Met Thr Ala Thr Pro
1780                1785                1790 ccg gga agc aga gac cca ttt cct cag agc aat gca cca atc ata               5520
Pro Gly Ser Arg Asp Pro Phe Pro Gln Ser Asn Ala Pro Ile Ile
1795                1800                1805 gat gaa gaa aga gaa atc cct gaa cgc tcg tgg aat tcc gga cat               5565
Asp Glu Glu Arg Glu Ile Pro Glu Arg Ser Trp Asn Ser Gly His
1810                1815                1820 gaa tgg gtc acg gat ttt aaa ggg aag act gtt tgg ttc gtt cca               5610
Glu Trp Val Thr Asp Phe Lys Gly Lys Thr Val Trp Phe Val Pro
1825                1830                1835 agt ata aaa gca gga aat gat ata gca gct tgc ctg agg aaa aat               5655
Ser Ile Lys Ala Gly Asn Asp Ile Ala Ala Cys Leu Arg Lys Asn
1840                1845                1850 gga aag aaa gtg ata caa ctc agt agg aag acc ttt gat tct gag               5700
Gly Lys Lys Val Ile Gln Leu Ser Arg Lys Thr Phe Asp Ser Glu
1855                1860                1865 tat gtc aag act aga acc aat gat tgg gac ttc gtg gtt aca act               5745
Tyr Val Lys Thr Arg Thr Asn Asp Trp Asp Phe Val Val Thr Thr
1870                1875                1880 gac att tca gaa atg ggt gcc aat ttc aag gct gag agg gtt ata               5790
Asp Ile Ser Glu Met Gly Ala Asn Phe Lys Ala Glu Arg Val Ile
1885                1890                1895 gac ccc aga cgc tgc atg aaa cca gtc ata cta aca gat ggt gaa               5835
Asp Pro Arg Arg Cys Met Lys Pro Val Ile Leu Thr Asp Gly Glu
1900                1905                1910 gag cgg gtg att ctg gca gga cct atg cca gtg acc cac tct agt               5880
Glu Arg Val Ile Leu Ala Gly Pro Met Pro Val Thr His Ser Ser
1915                1920                1925 gca gca caa aga aga ggg aga ata gga aga aat cca aaa aat gag               5925
Ala Ala Gln Arg Arg Gly Arg Ile Gly Arg Asn Pro Lys Asn Glu
1930                1935                1940 aat gac cag tac ata tac atg ggg gaa cct ctg gaa aat gat gaa               5970
Asn Asp Gln Tyr Ile Tyr Met Gly Glu Pro Leu Glu Asn Asp Glu
1945                1950                1955 gac tgt gca cac tgg aaa gaa gct aaa atg ctc cta gat aac atc               6015
Asp Cys Ala His Trp Lys Glu Ala Lys Met Leu Leu Asp Asn Ile
1960                1965                1970
```

-continued

| | | |
|---|---|---|
| aac acg cca gaa gga atc att cct agc atg ttc gaa cca gag cgt<br>Asn Thr Pro Glu Gly Ile Ile Pro Ser Met Phe Glu Pro Glu Arg<br>　　　1975　　　　　　　1980　　　　　　　　　1985 | | 6060 |
| gaa aag gtg gat gcc att gat ggc gaa tac cgc ttg aga gga gaa<br>Glu Lys Val Asp Ala Ile Asp Gly Glu Tyr Arg Leu Arg Gly Glu<br>　　　1990　　　　　　　1995　　　　　　　　　2000 | | 6105 |
| gca agg aaa acc ttt gta gac tta atg aga aga gga gac cta cca<br>Ala Arg Lys Thr Phe Val Asp Leu Met Arg Arg Gly Asp Leu Pro<br>　　　2005　　　　　　　2010　　　　　　　　　2015 | | 6150 |
| gtc tgg ttg gcc tac aga gtg gca gct gaa ggc atc aac tac gca<br>Val Trp Leu Ala Tyr Arg Val Ala Ala Glu Gly Ile Asn Tyr Ala<br>　　　2020　　　　　　　2025　　　　　　　　　2030 | | 6195 |
| gac aga agg tgg tgt ttt gat gga gtc aag aac aac caa atc cta<br>Asp Arg Arg Trp Cys Phe Asp Gly Val Lys Asn Asn Gln Ile Leu<br>　　　2035　　　　　　　2040　　　　　　　　　2045 | | 6240 |
| gaa gaa aac gtg gaa gtt gaa atc tgg aca aaa gaa ggg gaa agg<br>Glu Glu Asn Val Glu Val Glu Ile Trp Thr Lys Glu Gly Glu Arg<br>　　　2050　　　　　　　2055　　　　　　　　　2060 | | 6285 |
| aag aaa ttg aaa ccc aga tgg ttg gat gct agg atc tat tct gac<br>Lys Lys Leu Lys Pro Arg Trp Leu Asp Ala Arg Ile Tyr Ser Asp<br>　　　2065　　　　　　　2070　　　　　　　　　2075 | | 6330 |
| cca ctg gcg cta aaa gaa ttt aag gaa ttt gca gcc gga aga aag<br>Pro Leu Ala Leu Lys Glu Phe Lys Glu Phe Ala Ala Gly Arg Lys<br>　　　2080　　　　　　　2085　　　　　　　　　2090 | | 6375 |
| tct ctg acc ctg aac cta atc aca gaa atg ggt agg ctc cca acc<br>Ser Leu Thr Leu Asn Leu Ile Thr Glu Met Gly Arg Leu Pro Thr<br>　　　2095　　　　　　　2100　　　　　　　　　2105 | | 6420 |
| ttc atg act cag aag gca aga gac gca ctg gac aac tta gca gtg<br>Phe Met Thr Gln Lys Ala Arg Asp Ala Leu Asp Asn Leu Ala Val<br>　　　2110　　　　　　　2115　　　　　　　　　2120 | | 6465 |
| ctg cac acg gct gag gca ggt gga agg gcg tac aac cat gct ctc<br>Leu His Thr Ala Glu Ala Gly Gly Arg Ala Tyr Asn His Ala Leu<br>　　　2125　　　　　　　2130　　　　　　　　　2135 | | 6510 |
| agt gaa ctg ccg gag acc ctg gag aca ttg ctt tta ctg aca ctt<br>Ser Glu Leu Pro Glu Thr Leu Glu Thr Leu Leu Leu Leu Thr Leu<br>　　　2140　　　　　　　2145　　　　　　　　　2150 | | 6555 |
| ctg gct aca gtc acg gga ggg atc ttt tta ttc ttg atg agc gca<br>Leu Ala Thr Val Thr Gly Gly Ile Phe Leu Phe Leu Met Ser Ala<br>　　　2155　　　　　　　2160　　　　　　　　　2165 | | 6600 |
| agg ggc ata ggg aag atg acc ctg gga atg tgc tgc ata atc acg<br>Arg Gly Ile Gly Lys Met Thr Leu Gly Met Cys Cys Ile Ile Thr<br>　　　2170　　　　　　　2175　　　　　　　　　2180 | | 6645 |
| gct agc atc ctc cta tgg tac gca caa ata cag cca cac tgg ata<br>Ala Ser Ile Leu Leu Trp Tyr Ala Gln Ile Gln Pro His Trp Ile<br>　　　2185　　　　　　　2190　　　　　　　　　2195 | | 6690 |
| gca gct tca ata ata ctg gag ttt ttt ctc ata gtt ttg ctt att<br>Ala Ala Ser Ile Ile Leu Glu Phe Phe Leu Ile Val Leu Leu Ile<br>　　　2200　　　　　　　2205　　　　　　　　　2210 | | 6735 |
| cca gaa cct gaa aaa cag aga aca ccc caa gac aac caa ctg acc<br>Pro Glu Pro Glu Lys Gln Arg Thr Pro Gln Asp Asn Gln Leu Thr<br>　　　2215　　　　　　　2220　　　　　　　　　2225 | | 6780 |
| tac gtt gtc ata gcc atc ctc aca gtg gtg gcc acc atg gca<br>Tyr Val Val Ile Ala Ile Leu Thr Val Val Ala Ala Thr Met Ala<br>　　　2230　　　　　　　2235　　　　　　　　　2240 | | 6825 |
| aac gag atg ggt ttc cta gaa aaa acg aag aaa gat ctc gga ttg<br>Asn Glu Met Gly Phe Leu Glu Lys Thr Lys Lys Asp Leu Gly Leu<br>　　　2245　　　　　　　2250　　　　　　　　　2255 | | 6870 |
| gga agc att gca acc cag caa ccc gag agc aac atc ctg gac ata<br>Gly Ser Ile Ala Thr Gln Gln Pro Glu Ser Asn Ile Leu Asp Ile<br>　　　2260　　　　　　　2265　　　　　　　　　2270 | | 6915 |

-continued

| | | |
|---|---|---|
| gat cta cgt cct gca tca gca tgg acg ctg tat gcc gtg gcc aca<br>Asp Leu Arg Pro Ala Ser Ala Trp Thr Leu Tyr Ala Val Ala Thr<br>2275                    2280                          2285 | 6960 |
| aca ttt gtt aca cca atg ttg aga cat agc att gaa aat tcc tca<br>Thr Phe Val Thr Pro Met Leu Arg His Ser Ile Glu Asn Ser Ser<br>2290                    2295                          2300 | 7005 |
| gtg aat gtg tcc cta aca gct ata gcc aac caa gcc aca gtg tta<br>Val Asn Val Ser Leu Thr Ala Ile Ala Asn Gln Ala Thr Val Leu<br>2305                    2310                          2315 | 7050 |
| atg ggt ctc ggg aaa gga tgg cca ttg tca aag atg gac atc gga<br>Met Gly Leu Gly Lys Gly Trp Pro Leu Ser Lys Met Asp Ile Gly<br>2320                    2325                          2330 | 7095 |
| gtt ccc ctt ctc gcc att gga tgc tac tca caa gtc aac ccc ata<br>Val Pro Leu Leu Ala Ile Gly Cys Tyr Ser Gln Val Asn Pro Ile<br>2335                    2340                          2345 | 7140 |
| act ctc aca gca gct ctt ttc tta ttg gta gca cat tat gcc atc<br>Thr Leu Thr Ala Ala Leu Phe Leu Leu Val Ala His Tyr Ala Ile<br>2350                    2355                          2360 | 7185 |
| ata ggg cca gga ctc caa gca aaa gca acc aga gaa gct cag aaa<br>Ile Gly Pro Gly Leu Gln Ala Lys Ala Thr Arg Glu Ala Gln Lys<br>2365                    2370                          2375 | 7230 |
| aga gca gcg gcg ggc atc atg aaa aac cca act gtc gat gga ata<br>Arg Ala Ala Ala Gly Ile Met Lys Asn Pro Thr Val Asp Gly Ile<br>2380                    2385                          2390 | 7275 |
| aca gtg att gac cta gat cca ata cct tat gat cca aag ttt gaa<br>Thr Val Ile Asp Leu Asp Pro Ile Pro Tyr Asp Pro Lys Phe Glu<br>2395                    2400                          2405 | 7320 |
| aag cag ttg gga caa gta atg ctc cta gtc ctc tgc gtg act caa<br>Lys Gln Leu Gly Gln Val Met Leu Leu Val Leu Cys Val Thr Gln<br>2410                    2415                          2420 | 7365 |
| gta ttg atg atg agg act aca tgg gct ctg tgt gag gct tta acc<br>Val Leu Met Met Arg Thr Thr Trp Ala Leu Cys Glu Ala Leu Thr<br>2425                    2430                          2435 | 7410 |
| tta gct acc ggg ccc atc tcc aca ttg tgg gaa gga aat cca ggg<br>Leu Ala Thr Gly Pro Ile Ser Thr Leu Trp Glu Gly Asn Pro Gly<br>2440                    2445                          2450 | 7455 |
| agg ttt tgg aac act acc att gcg gtg tca atg gct aac att ttt<br>Arg Phe Trp Asn Thr Thr Ile Ala Val Ser Met Ala Asn Ile Phe<br>2455                    2460                          2465 | 7500 |
| aga ggg agt tac ttg gcc gga gct gga ctt ctc ttt tct att atg<br>Arg Gly Ser Tyr Leu Ala Gly Ala Gly Leu Leu Phe Ser Ile Met<br>2470                    2475                          2480 | 7545 |
| aag aac aca acc aac aca aga agg gga act ggc aac ata gga gag<br>Lys Asn Thr Thr Asn Thr Arg Arg Gly Thr Gly Asn Ile Gly Glu<br>2485                    2490                          2495 | 7590 |
| acg ctt gga gag aaa tgg aaa agc cga ttg aac gca ttg gga aaa<br>Thr Leu Gly Glu Lys Trp Lys Ser Arg Leu Asn Ala Leu Gly Lys<br>2500                    2505                          2510 | 7635 |
| agt gaa ttc cag atc tac aag aaa agt gga atc cag gaa gtg gat<br>Ser Glu Phe Gln Ile Tyr Lys Lys Ser Gly Ile Gln Glu Val Asp<br>2515                    2520                          2525 | 7680 |
| aga acc tta gca aaa gaa ggc att aaa aga gga gaa acg gac cat<br>Arg Thr Leu Ala Lys Glu Gly Ile Lys Arg Gly Glu Thr Asp His<br>2530                    2535                          2540 | 7725 |
| cac gct gtg tcg cga ggc tca gca aaa ctg aga tgg ttc gtt gag<br>His Ala Val Ser Arg Gly Ser Ala Lys Leu Arg Trp Phe Val Glu<br>2545                    2550                          2555 | 7770 |
| aga aac atg gtc aca cca gaa ggg aaa gta gtg gac ctc ggt tgt<br>Arg Asn Met Val Thr Pro Glu Gly Lys Val Val Asp Leu Gly Cys | 7815 |

```
                2560                2565                2570
ggc aga gga ggc tgg tca tac tat tgt gga gga cta aag aat gta       7860
Gly Arg Gly Gly Trp Ser Tyr Tyr Cys Gly Gly Leu Lys Asn Val
    2575                2580                2585 aga gaa gtc aaa ggc cta aca aaa gga gga cca gga cac gaa gaa       7905
Arg Glu Val Lys Gly Leu Thr Lys Gly Gly Pro Gly His Glu Glu
    2590                2595                2600 ccc atc ccc atg tca aca tat ggg tgg aat cta gtg cgt ctt caa       7950
Pro Ile Pro Met Ser Thr Tyr Gly Trp Asn Leu Val Arg Leu Gln
    2605                2610                2615 agt gga gtt gac gtt ttc ttc atc ccg cca gaa aag tgt gac aca       7995
Ser Gly Val Asp Val Phe Phe Ile Pro Pro Glu Lys Cys Asp Thr
    2620                2625                2630 tta ttg tgt gac ata ggg gag tca tca cca aat ccc aca gtg gaa       8040
Leu Leu Cys Asp Ile Gly Glu Ser Ser Pro Asn Pro Thr Val Glu
    2635                2640                2645 gca gga cga aca ctc aga gtc ctt aac tta gta gaa aat tgg ttg       8085
Ala Gly Arg Thr Leu Arg Val Leu Asn Leu Val Glu Asn Trp Leu
    2650                2655                2660 aac aac aac act caa ttt tgc ata aag gtt ctc aac cca tat atg       8130
Asn Asn Asn Thr Gln Phe Cys Ile Lys Val Leu Asn Pro Tyr Met
    2665                2670                2675 ccc tca gtc ata gaa aaa atg gaa gca cta caa agg aaa tat gga       8175
Pro Ser Val Ile Glu Lys Met Glu Ala Leu Gln Arg Lys Tyr Gly
    2680                2685                2690 gga gcc tta gtg agg aat cca ctc tca cga aac tcc aca cat gag       8220
Gly Ala Leu Val Arg Asn Pro Leu Ser Arg Asn Ser Thr His Glu
    2695                2700                2705 atg tac tgg gta tcc aat gct tcc ggg aac ata gtg tca tca gtg       8265
Met Tyr Trp Val Ser Asn Ala Ser Gly Asn Ile Val Ser Ser Val
    2710                2715                2720 aac atg att tca agg atg ttg atc aac aga ttt aca atg aga tac       8310
Asn Met Ile Ser Arg Met Leu Ile Asn Arg Phe Thr Met Arg Tyr
    2725                2730                2735 aag aaa gcc act tac gag ccg gat gtt gac ctc gga agc gga acc       8355
Lys Lys Ala Thr Tyr Glu Pro Asp Val Asp Leu Gly Ser Gly Thr
    2740                2745                2750 cgt aac atc ggg att gaa agt gag ata cca aac cta gat ata att       8400
Arg Asn Ile Gly Ile Glu Ser Glu Ile Pro Asn Leu Asp Ile Ile
    2755                2760                2765 ggg aaa aga ata gaa aaa ata aag caa gag cat gaa aca tca tgg       8445
Gly Lys Arg Ile Glu Lys Ile Lys Gln Glu His Glu Thr Ser Trp
    2770                2775                2780 cac tat gac caa gac cac cca tac aaa acg tgg gca tac cat ggt       8490
His Tyr Asp Gln Asp His Pro Tyr Lys Thr Trp Ala Tyr His Gly
    2785                2790                2795 agc tat gaa aca aaa cag act gga tca gca tca tcc atg gtc aac       8535
Ser Tyr Glu Thr Lys Gln Thr Gly Ser Ala Ser Ser Met Val Asn
    2800                2805                2810 gga gtg gtc agg ctg ctg aca aaa cct tgg gac gtt gtc ccc atg       8580
Gly Val Val Arg Leu Leu Thr Lys Pro Trp Asp Val Val Pro Met
    2815                2820                2825 gtg aca cag atg gca atg aca gac acg act cca ttt gga caa cag       8625
Val Thr Gln Met Ala Met Thr Asp Thr Thr Pro Phe Gly Gln Gln
    2830                2835                2840 cgc gtt ttt aaa gag aaa gtg gac acg aga acc caa gaa ccg aaa       8670
Arg Val Phe Lys Glu Lys Val Asp Thr Arg Thr Gln Glu Pro Lys
    2845                2850                2855 gaa ggc acg aag aaa cta atg aaa ata aca gca gag tgg ctt tgg       8715
```

-continued

| | | | | | | | | | | | | | | | |
|---|---|---|---|---|---|---|---|---|---|---|---|---|---|---|---|
| Glu | Gly | Thr | Lys | Lys | Leu | Met | Lys | Ile | Thr | Ala | Glu | Trp | Leu | Trp | |
| | | | | 2865 | | | | | 2870 | | | | | | |

```
aaa gaa tta ggg aag aaa aag aca ccc agg atg tgc acc aga gaa      8760
Lys Glu Leu Gly Lys Lys Lys Thr Pro Arg Met Cys Thr Arg Glu
2875                2880                2885 gaa ttc aca aga aag gtg aga agc aat gca gcc ttg ggg gcc ata      8805
Glu Phe Thr Arg Lys Val Arg Ser Asn Ala Ala Leu Gly Ala Ile
2890                2895                2900 ttc act gat gag aac aag tgg aag tcg gca cgt gag gct gtt gaa      8850
Phe Thr Asp Glu Asn Lys Trp Lys Ser Ala Arg Glu Ala Val Glu
2905                2910                2915 gat agt agg ttt tgg gag ctg gtt gac aag gaa agg aat ctc cat      8895
Asp Ser Arg Phe Trp Glu Leu Val Asp Lys Glu Arg Asn Leu His
2920                2925                2930 ctt gaa gga aag tgt gaa aca tgt gtg tac aac atg atg gga aaa      8940
Leu Glu Gly Lys Cys Glu Thr Cys Val Tyr Asn Met Met Gly Lys
2935                2940                2945 aga gag aag aag cta ggg gaa ttc ggc aag gca aaa ggc agc aga      8985
Arg Glu Lys Lys Leu Gly Glu Phe Gly Lys Ala Lys Gly Ser Arg
2950                2955                2960 gcc ata tgg tac atg tgg ctt gga gca cgc ttc tta gag ttt gaa      9030
Ala Ile Trp Tyr Met Trp Leu Gly Ala Arg Phe Leu Glu Phe Glu
2965                2970                2975 gcc cta gga ttc tta aat gaa gat cac tgg ttc tcc aga gag aac      9075
Ala Leu Gly Phe Leu Asn Glu Asp His Trp Phe Ser Arg Glu Asn
2980                2985                2990 tcc ctg agt gga gtg gaa gga gaa ggg ctg cac aag cta ggt tac      9120
Ser Leu Ser Gly Val Glu Gly Glu Gly Leu His Lys Leu Gly Tyr
2995                3000                3005 att cta aga gac gtg agc aag aaa gag gga gga gca atg tat gcc      9165
Ile Leu Arg Asp Val Ser Lys Lys Glu Gly Gly Ala Met Tyr Ala
3010                3015                3020 gat gac acc gca gga tgg gat aca aaa atc aca cta gaa gac cta      9210
Asp Asp Thr Ala Gly Trp Asp Thr Lys Ile Thr Leu Glu Asp Leu
3025                3030                3035 aaa aat gaa gag atg gta aca aac cac atg gaa gga gaa cac aag      9255
Lys Asn Glu Glu Met Val Thr Asn His Met Glu Gly Glu His Lys
3040                3045                3050 aaa cta gcc gag gcc att ttc aaa cta acg tac caa aac aag gtg      9300
Lys Leu Ala Glu Ala Ile Phe Lys Leu Thr Tyr Gln Asn Lys Val
3055                3060                3065 gtg cgt gtg caa aga cca aca cca aga ggc aca gta atg gac atc      9345
Val Arg Val Gln Arg Pro Thr Pro Arg Gly Thr Val Met Asp Ile
3070                3075                3080 ata tcg aga aga gac caa aga ggt agt gga caa gtt ggc acc tat      9390
Ile Ser Arg Arg Asp Gln Arg Gly Ser Gly Gln Val Gly Thr Tyr
3085                3090                3095 gga ctc aat act ttc acc aat atg gaa gcc caa cta atc aga cag      9435
Gly Leu Asn Thr Phe Thr Asn Met Glu Ala Gln Leu Ile Arg Gln
3100                3105                3110 atg gag gga gaa gga gtc ttt aaa agc att cag cac cta aca atc      9480
Met Glu Gly Glu Gly Val Phe Lys Ser Ile Gln His Leu Thr Ile
3115                3120                3125 aca gaa gaa atc gct gtg caa aac tgg tta gca aga gtg ggg cgc      9525
Thr Glu Glu Ile Ala Val Gln Asn Trp Leu Ala Arg Val Gly Arg
3130                3135                3140 gaa agg tta tca aga atg gcc atc agt gga gat gat tgt gtt gtg      9570
Glu Arg Leu Ser Arg Met Ala Ile Ser Gly Asp Asp Cys Val Val
3145                3150                3155
```

| | | | | | | | | | | | |
|---|---|---|---|---|---|---|---|---|---|---|---|
| aaa | cct | tta | gat | gac | agg | ttc | gca | agc | gct | tta | aca | gct | cta | aat | 9615 |
| Lys | Pro | Leu | Asp | Asp | Arg | Phe | Ala | Ser | Ala | Leu | Thr | Ala | Leu | Asn | |
| 3160 | | | | 3165 | | | | | 3170 | | | | | | |

| gac | atg | gga | aag | att | agg | aaa | gac | ata | caa | caa | tgg | gaa | cct | tca | 9660 |
|---|---|---|---|---|---|---|---|---|---|---|---|---|---|---|---|
| Asp | Met | Gly | Lys | Ile | Arg | Lys | Asp | Ile | Gln | Gln | Trp | Glu | Pro | Ser | |
| 3175 | | | | | 3180 | | | | | 3185 | | | | | |

| aga | gga | tgg | aat | gat | tgg | aca | caa | gtg | ccc | ttc | tgt | tca | cac | cat | 9705 |
|---|---|---|---|---|---|---|---|---|---|---|---|---|---|---|---|
| Arg | Gly | Trp | Asn | Asp | Trp | Thr | Gln | Val | Pro | Phe | Cys | Ser | His | His | |
| 3190 | | | | | 3195 | | | | 3200 | | | | | | |

| ttc | cat | gag | tta | atc | atg | aaa | gac | ggt | cgc | gta | ctc | gtt | gtt | cca | 9750 |
|---|---|---|---|---|---|---|---|---|---|---|---|---|---|---|---|
| Phe | His | Glu | Leu | Ile | Met | Lys | Asp | Gly | Arg | Val | Leu | Val | Val | Pro | |
| 3205 | | | | 3210 | | | | | 3215 | | | | | | |

| tgt | aga | aac | caa | gat | gaa | ctg | att | ggc | aga | gcc | cga | atc | tcc | caa | 9795 |
|---|---|---|---|---|---|---|---|---|---|---|---|---|---|---|---|
| Cys | Arg | Asn | Gln | Asp | Glu | Leu | Ile | Gly | Arg | Ala | Arg | Ile | Ser | Gln | |
| 3220 | | | | 3225 | | | | | 3230 | | | | | | |

| gga | gca | ggg | tgg | tct | ttg | cgg | gag | acg | gcc | tgt | ttg | ggg | aag | tct | 9840 |
|---|---|---|---|---|---|---|---|---|---|---|---|---|---|---|---|
| Gly | Ala | Gly | Trp | Ser | Leu | Arg | Glu | Thr | Ala | Cys | Leu | Gly | Lys | Ser | |
| 3235 | | | | 3240 | | | | | 3245 | | | | | | |

| tac | gcc | caa | atg | tgg | agc | ttg | atg | tac | ttc | cac | aga | cgc | gac | ctc | 9885 |
|---|---|---|---|---|---|---|---|---|---|---|---|---|---|---|---|
| Tyr | Ala | Gln | Met | Trp | Ser | Leu | Met | Tyr | Phe | His | Arg | Arg | Asp | Leu | |
| 3250 | | | | | 3255 | | | | | 3260 | | | | | |

| agg | ctg | gcg | gca | aat | gct | att | tgc | tcg | gca | gta | cca | tca | cat | tgg | 9930 |
|---|---|---|---|---|---|---|---|---|---|---|---|---|---|---|---|
| Arg | Leu | Ala | Ala | Asn | Ala | Ile | Cys | Ser | Ala | Val | Pro | Ser | His | Trp | |
| 3265 | | | | | 3270 | | | | | 3275 | | | | | |

| gtt | cca | aca | agt | cga | aca | acc | tgg | tcc | ata | cat | gct | aaa | cat | gaa | 9975 |
|---|---|---|---|---|---|---|---|---|---|---|---|---|---|---|---|
| Val | Pro | Thr | Ser | Arg | Thr | Thr | Trp | Ser | Ile | His | Ala | Lys | His | Glu | |
| 3280 | | | | 3285 | | | | | 3290 | | | | | | |

| tgg | atg | aca | acg | gaa | gac | atg | ctg | aca | gtc | tgg | aac | agg | gtg | tgg | 10020 |
|---|---|---|---|---|---|---|---|---|---|---|---|---|---|---|---|
| Trp | Met | Thr | Thr | Glu | Asp | Met | Leu | Thr | Val | Trp | Asn | Arg | Val | Trp | |
| 3295 | | | | | 3300 | | | | | 3305 | | | | | |

| att | caa | gaa | aac | cca | tgg | atg | gaa | gac | aaa | act | cca | gtg | gaa | aca | 10065 |
|---|---|---|---|---|---|---|---|---|---|---|---|---|---|---|---|
| Ile | Gln | Glu | Asn | Pro | Trp | Met | Glu | Asp | Lys | Thr | Pro | Val | Glu | Thr | |
| 3310 | | | | 3315 | | | | | 3320 | | | | | | |

| tgg | gag | gaa | atc | cca | tac | ttg | ggg | aaa | aga | gaa | gac | caa | tgg | tgc | 10110 |
|---|---|---|---|---|---|---|---|---|---|---|---|---|---|---|---|
| Trp | Glu | Glu | Ile | Pro | Tyr | Leu | Gly | Lys | Arg | Glu | Asp | Gln | Trp | Cys | |
| 3325 | | | | 3330 | | | | | 3335 | | | | | | |

| ggc | tca | ttg | att | ggg | tta | aca | agc | agg | gcc | acc | tgg | gca | aag | aac | 10155 |
|---|---|---|---|---|---|---|---|---|---|---|---|---|---|---|---|
| Gly | Ser | Leu | Ile | Gly | Leu | Thr | Ser | Arg | Ala | Thr | Trp | Ala | Lys | Asn | |
| 3340 | | | | 3345 | | | | | 3350 | | | | | | |

| atc | caa | gca | gca | ata | aat | caa | gtt | aga | tcc | ctt | ata | ggc | aat | gaa | 10200 |
|---|---|---|---|---|---|---|---|---|---|---|---|---|---|---|---|
| Ile | Gln | Ala | Ala | Ile | Asn | Gln | Val | Arg | Ser | Leu | Ile | Gly | Asn | Glu | |
| 3355 | | | | 3360 | | | | | 3365 | | | | | | |

| gaa | tac | aca | gat | tac | atg | cca | tcc | atg | aaa | aga | ttc | aga | aga | gaa | 10245 |
|---|---|---|---|---|---|---|---|---|---|---|---|---|---|---|---|
| Glu | Tyr | Thr | Asp | Tyr | Met | Pro | Ser | Met | Lys | Arg | Phe | Arg | Arg | Glu | |
| 3370 | | | | 3375 | | | | | 3380 | | | | | | |

| gag | gaa | gaa | gca | gga | gtt | ctg | tgg | tag | aaagcaaaac | taacatgaaa | 10292 |
|---|---|---|---|---|---|---|---|---|---|---|---|
| Glu | Glu | Glu | Ala | Gly | Val | Leu | Trp | | | | |
| 3385 | | | | | 3390 | | | | | | | caaggctaga agtcaggtcg gattaagcca tagtacggaa aaactatgc tacctgtgag    10352 ccccgtccaa ggacgttaaa agaagtcagg ccatcataaa tgccatagct tgagtaaact    10412 atgcagcctg tagctccacc tgagaaggtg taaaaaatcc gggaggccac aaaccatgga    10472 agctgtacgc atggcgtagt ggactagcgg ttagggggaga cccctcccctt acaaatcgca    10532 gcaacaatgg gggcccaagg cgagatgaag ctgtagtctc gctggaagga ctagaggtta    10592 gaggagaccc ccccgaaaca aaaaacagca tattgacgct gggaaagacc agagatcctg    10652 ctgtctcctc agcatcattc caggcacaga acgccagaaa atggaatggt gctgttgaat    10712 caacaggttc t                                                          10723

<210> SEQ ID NO 2
<211> LENGTH: 3391
<212> TYPE: PRT
<213> ORGANISM: Dengue virus

<400> SEQUENCE: 2

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Glu Val Gly
    130                 135                 140

Val Asn Met Cys Thr Leu Met Ala Met Asp Leu Gly Glu Leu Cys Glu
145                 150                 155                 160

Asp Thr Ile Thr Tyr Lys Cys Pro Leu Leu Arg Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Met Gly Glu His Arg Arg Glu Lys Arg Ser Val Ala
        195                 200                 205

Leu Val Pro His Val Arg Met Gly Leu Glu Thr Arg Thr Glu Thr Trp
    210                 215                 220

Met Ser Ser Glu Gly Ala Trp Lys His Val Gln Arg Ile Glu Thr Trp
225                 230                 235                 240

Ile Leu Arg His Pro Gly Phe Thr Met Met Ala Ala Ile Leu Ala Tyr
                245                 250                 255

Thr Ile Gly Thr Thr His Phe Gln Arg Ala Leu Ile Phe Ile Leu Leu
            260                 265                 270

Thr Ala Val Thr Pro Ser Met Thr Met Arg Cys Ile Gly Met Ser Asn
        275                 280                 285

Arg Asp Phe Val Glu Gly Val Ser Gly Gly Ser Trp Val Asp Ile Val
    290                 295                 300

Leu Glu His Gly Ser Cys Val Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Glu Ser
            340                 345                 350

Arg Cys Pro Thr Gln Gly Glu Pro Ser Leu Asn Glu Glu Gln Asp Lys
        355                 360                 365

Arg Phe Val Cys Lys His Ser Met Val Asp Arg Gly Trp Gly Asn Gly
```

```
                    370             375             380
Cys Gly Leu Phe Gly Lys Gly Ile Val Thr Cys Ala Met Phe Arg
385                 390             395                 400

Cys Lys Lys Asn Met Glu Gly Lys Val Val Gln Pro Glu Asn Leu Glu
                    405             410             415

Tyr Thr Ile Val Ile Thr Pro His Ser Gly Glu His Ala Val Gly
                420             425             430

Asn Asp Thr Gly Lys His Gly Lys Glu Ile Lys Ile Thr Pro Gln Ser
                435             440             445

Ser Ile Thr Glu Ala Glu Leu Thr Gly Tyr Gly Thr Val Thr Met Glu
    450             455             460

Cys Ser Pro Arg Thr Gly Leu Asp Phe Asn Glu Met Val Leu Leu Gln
465             470             475             480

Met Glu Asn Lys Ala Trp Leu Val His Arg Gln Trp Phe Leu Asp Leu
                485             490             495

Pro Leu Pro Trp Leu Pro Gly Ala Asp Thr Gln Glu Ser Asn Trp Ile
                500             505             510

Gln Lys Glu Thr Leu Val Thr Phe Lys Asn Pro His Ala Lys Lys Gln
        515             520             525

Asp Val Val Leu Gly Ser Gln Glu Gly Ala Met His Thr Ala Leu
        530             535             540

Thr Gly Ala Thr Glu Ile Gln Met Ser Ser Gly Asn Leu Leu Phe Thr
545             550             555             560

Gly His Leu Lys Cys Arg Leu Arg Met Asp Lys Leu Gln Leu Lys Gly
                565             570             575

Met Ser Tyr Ser Met Cys Thr Gly Lys Phe Lys Val Val Lys Glu Ile
                580             585             590

Ala Glu Thr Gln His Gly Thr Ile Val Ile Arg Val Gln Tyr Glu Gly
                595             600             605

Asp Gly Ser Pro Cys Lys Ile Pro Phe Glu Ile Met Asp Leu Glu Lys
                610             615             620

Arg His Val Leu Gly Arg Leu Ile Thr Val Asn Pro Ile Val Thr Glu
625             630             635             640

Lys Asp Ser Pro Val Asn Ile Glu Ala Glu Pro Pro Phe Gly Asp Ser
                645             650             655

Tyr Ile Ile Ile Gly Val Glu Pro Gly Gln Leu Lys Leu Asn Trp Phe
                660             665             670

Lys Lys Gly Ser Ser Ile Gly Gln Met Phe Glu Thr Thr Met Arg Gly
                675             680             685

Ala Lys Arg Met Ala Ile Leu Gly Asp Thr Ala Trp Asp Phe Gly Ser
                690             695             700

Leu Gly Gly Val Phe Thr Ser Ile Gly Lys Ala Leu His Gln Val Phe
705                 710             715                 720

Gly Ala Ile Tyr Gly Ala Ala Phe Ser Gly Val Ser Trp Thr Met Lys
                725             730             735

Ile Leu Ile Gly Val Ile Ile Thr Trp Ile Gly Met Asn Ser Arg Ser
                740             745             750

Thr Ser Leu Ser Val Thr Leu Val Leu Val Gly Ile Val Thr Leu Tyr
        755             760             765

Leu Gly Val Met Val Gln Ala Asp Ser Gly Cys Val Val Ser Trp Lys
        770             775             780

Asn Lys Glu Leu Lys Cys Gly Ser Gly Ile Phe Ile Thr Asp Asn Val
785                 790             795                 800
```

```
His Thr Trp Thr Glu Gln Tyr Lys Phe Gln Pro Glu Ser Pro Ser Lys
            805                 810                 815

Leu Ala Ser Ala Ile Gln Lys Ala His Glu Asp Ile Cys Gly Ile
        820                 825                 830

Arg Ser Val Thr Arg Leu Glu Asn Leu Met Trp Lys Gln Ile Thr Pro
            835                 840                 845

Glu Leu Asn His Ile Leu Ser Glu Asn Glu Val Lys Leu Thr Ile Met
        850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
            885                 890                 895

Lys Met Leu Ser Thr Glu Ser His Asn Gln Thr Phe Leu Ile Asp Gly
        900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
        930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
            965                 970                 975

Ile Glu Ser Ala Leu Asn Asp Thr Trp Lys Ile Glu Lys Ala Ser Phe
        980                 985                 990

Ile Glu Val Lys Asn Cys His Trp Pro Lys Ser His Thr Leu Trp Ser
        995                 1000                1005

Asn Gly Val Leu Glu Ser Glu Met Ile Ile Pro Lys Asn Leu Ala
    1010                1015                1020

Gly Pro Val Ser Gln His Asn Tyr Arg Pro Gly Tyr His Thr Gln
    1025                1030                1035

Ile Thr Gly Pro Trp His Leu Gly Lys Leu Glu Met Asp Phe Asp
    1040                1045                1050

Phe Cys Asp Gly Thr Thr Val Val Val Thr Glu Asp Cys Gly Asn
    1055                1060                1065

Arg Gly Pro Ser Leu Arg Thr Thr Thr Ala Ser Gly Lys Leu Ile
    1070                1075                1080

Thr Glu Trp Cys Cys Arg Ser Cys Thr Leu Pro Pro Leu Arg Tyr
    1085                1090                1095

Arg Gly Glu Asp Gly Cys Trp Tyr Gly Met Glu Ile Arg Pro Leu
    1100                1105                1110

Lys Glu Lys Glu Glu Asn Leu Val Asn Ser Leu Val Thr Ala Gly
    1115                1120                1125

His Gly Gln Val Asp Asn Phe Ser Leu Gly Val Leu Gly Met Ala
    1130                1135                1140

Leu Phe Leu Glu Glu Met Leu Arg Thr Arg Val Gly Thr Lys His
    1145                1150                1155

Ala Ile Leu Leu Val Ala Val Ser Phe Val Thr Leu Ile Thr Gly
    1160                1165                1170

Asn Met Ser Phe Arg Asp Leu Gly Arg Val Met Val Met Val Gly
    1175                1180                1185

Ala Thr Met Thr Asp Asp Ile Gly Met Gly Val Thr Tyr Leu Ala
    1190                1195                1200
```

-continued

| | | | | | | | | | | | | |
|---|---|---|---|---|---|---|---|---|---|---|---|---|
| Leu | Leu | Ala | Ala | Phe | Lys | Val | Arg | Pro | Thr | Phe | Ala | Ala Gly Leu |
| 1205 | | | | | 1210 | | | | | 1215 | | |
| Leu | Leu | Arg | Lys | Leu | Thr | Ser | Lys | Glu | Leu | Met | Met | Thr Thr Ile |
| 1220 | | | | | 1225 | | | | | 1230 | | |
| Gly | Ile | Val | Leu | Leu | Ser | Gln | Ser | Thr | Ile | Pro | Glu | Thr Ile Leu |
| 1235 | | | | | 1240 | | | | | 1245 | | |
| Glu | Leu | Thr | Asp | Ala | Leu | Ala | Leu | Gly | Met | Met | Val | Leu Lys Met |
| 1250 | | | | | 1255 | | | | | 1260 | | |
| Val | Arg | Asn | Met | Glu | Lys | Tyr | Gln | Leu | Ala | Val | Thr | Ile Met Ala |
| 1265 | | | | | 1270 | | | | | 1275 | | |
| Ile | Leu | Cys | Val | Pro | Asn | Ala | Val | Ile | Leu | Gln | Asn | Ala Trp Lys |
| 1280 | | | | | 1285 | | | | | 1290 | | |
| Val | Ser | Cys | Thr | Ile | Leu | Ala | Val | Val | Ser | Val | Ser | Pro Leu Phe |
| 1295 | | | | | 1300 | | | | | 1305 | | |
| Leu | Thr | Ser | Ser | Gln | Gln | Lys | Thr | Asp | Trp | Ile | Pro | Leu Ala Leu |
| 1310 | | | | | 1315 | | | | | 1320 | | |
| Thr | Ile | Lys | Gly | Leu | Asn | Pro | Thr | Ala | Ile | Phe | Leu | Thr Thr Leu |
| 1325 | | | | | 1330 | | | | | 1335 | | |
| Ser | Arg | Thr | Ser | Lys | Lys | Arg | Ser | Trp | Pro | Leu | Asn | Glu Ala Ile |
| 1340 | | | | | 1345 | | | | | 1350 | | |
| Met | Ala | Val | Gly | Met | Val | Ser | Ile | Leu | Ala | Ser | Ser | Leu Leu Lys |
| 1355 | | | | | 1360 | | | | | 1365 | | |
| Asn | Asp | Ile | Pro | Met | Thr | Gly | Pro | Leu | Val | Ala | Gly | Gly Leu Leu |
| 1370 | | | | | 1375 | | | | | 1380 | | |
| Thr | Val | Cys | Tyr | Val | Leu | Thr | Gly | Arg | Ser | Ala | Asp | Leu Glu Leu |
| 1385 | | | | | 1390 | | | | | 1395 | | |
| Glu | Arg | Ala | Ala | Asp | Val | Lys | Trp | Glu | Asp | Gln | Ala | Glu Ile Ser |
| 1400 | | | | | 1405 | | | | | 1410 | | |
| Gly | Ser | Ser | Pro | Ile | Leu | Ser | Ile | Thr | Ile | Ser | Glu | Asp Gly Ser |
| 1415 | | | | | 1420 | | | | | 1425 | | |
| Met | Ser | Ile | Lys | Asn | Glu | Glu | Glu | Glu | Gln | Thr | Leu | Thr Ile Leu |
| 1430 | | | | | 1435 | | | | | 1440 | | |
| Ile | Arg | Thr | Gly | Leu | Leu | Val | Ile | Ser | Gly | Leu | Phe | Pro Val Ser |
| 1445 | | | | | 1450 | | | | | 1455 | | |
| Ile | Pro | Ile | Thr | Ala | Ala | Ala | Trp | Tyr | Leu | Trp | Glu | Val Lys Lys |
| 1460 | | | | | 1465 | | | | | 1470 | | |
| Gln | Arg | Ala | Gly | Val | Leu | Trp | Asp | Val | Pro | Ser | Pro | Pro Pro Met |
| 1475 | | | | | 1480 | | | | | 1485 | | |
| Gly | Lys | Ala | Glu | Leu | Glu | Asp | Gly | Ala | Tyr | Arg | Ile | Lys Gln Lys |
| 1490 | | | | | 1495 | | | | | 1500 | | |
| Gly | Ile | Leu | Gly | Tyr | Ser | Gln | Ile | Gly | Ala | Gly | Val | Tyr Lys Glu |
| 1505 | | | | | 1510 | | | | | 1515 | | |
| Gly | Thr | Phe | His | Thr | Met | Trp | His | Val | Thr | Arg | Gly | Ala Val Leu |
| 1520 | | | | | 1525 | | | | | 1530 | | |
| Met | His | Lys | Gly | Lys | Arg | Ile | Glu | Pro | Thr | Trp | Ala | Asp Val Lys |
| 1535 | | | | | 1540 | | | | | 1545 | | |
| Lys | Asp | Leu | Ile | Ser | Tyr | Gly | Gly | Gly | Trp | Lys | Leu | Glu Gly Glu |
| 1550 | | | | | 1555 | | | | | 1560 | | |
| Trp | Lys | Glu | Gly | Glu | Glu | Val | Gln | Val | Leu | Ala | Leu | Glu Pro Gly |
| 1565 | | | | | 1570 | | | | | 1575 | | |
| Lys | Asn | Pro | Arg | Ala | Val | Gln | Thr | Lys | Pro | Gly | Leu | Phe Lys Thr |
| 1580 | | | | | 1585 | | | | | 1590 | | |
| Asn | Ala | Gly | Thr | Ile | Gly | Ala | Val | Ser | Leu | Asp | Phe | Ser Pro Gly |

```
            1595                1600                1605

Thr Ser Gly Ser Pro Ile Ile Asp Lys Lys Gly Lys Val Val Gly
    1610                1615                1620

Leu Tyr Gly Asn Gly Val Val Thr Arg Ser Gly Ala Tyr Val Ser
    1625                1630                1635

Ala Ile Ala Gln Thr Glu Lys Ser Ile Glu Asp Asn Pro Glu Ile
    1640                1645                1650

Glu Asp His Ile Phe Arg Lys Arg Arg Leu Thr Ile Met Asp Leu
    1655                1660                1665

His Pro Gly Ala Gly Lys Thr Lys Arg Tyr Leu Pro Ala Ile Val
    1670                1675                1680

Arg Glu Ala Ile Lys Arg Gly Leu Arg Thr Leu Ile Leu Ala Pro
    1685                1690                1695

Thr Arg Val Val Ala Ala Glu Met Glu Glu Ala Leu Arg Gly Leu
    1700                1705                1710

Pro Ile Arg Tyr Gln Thr Pro Ala Ile Arg Ala Glu His Thr Gly
    1715                1720                1725

Arg Glu Ile Val Asp Leu Met Cys His Ala Thr Phe Thr Met Arg
    1730                1735                1740

Leu Leu Ser Pro Val Arg Val Pro Asn Tyr Asn Leu Ile Ile Met
    1745                1750                1755

Asp Glu Ala His Phe Thr Asp Pro Ala Ser Ile Ala Ala Arg Gly
    1760                1765                1770

Tyr Ile Ser Thr Arg Val Glu Met Gly Glu Ala Ala Gly Ile Phe
    1775                1780                1785

Met Thr Ala Thr Pro Pro Gly Ser Arg Asp Pro Phe Pro Gln Ser
    1790                1795                1800

Asn Ala Pro Ile Ile Asp Glu Glu Arg Glu Ile Pro Glu Arg Ser
    1805                1810                1815

Trp Asn Ser Gly His Glu Trp Val Thr Asp Phe Lys Gly Lys Thr
    1820                1825                1830

Val Trp Phe Val Pro Ser Ile Lys Ala Gly Asn Asp Ile Ala Ala
    1835                1840                1845

Cys Leu Arg Lys Asn Gly Lys Lys Val Ile Gln Leu Ser Arg Lys
    1850                1855                1860

Thr Phe Asp Ser Glu Tyr Val Lys Thr Arg Thr Asn Asp Trp Asp
    1865                1870                1875

Phe Val Val Thr Thr Asp Ile Ser Glu Met Gly Ala Asn Phe Lys
    1880                1885                1890

Ala Glu Arg Val Ile Asp Pro Arg Arg Cys Met Lys Pro Val Ile
    1895                1900                1905

Leu Thr Asp Gly Glu Glu Arg Val Ile Leu Ala Gly Pro Met Pro
    1910                1915                1920

Val Thr His Ser Ser Ala Ala Gln Arg Arg Gly Arg Ile Gly Arg
    1925                1930                1935

Asn Pro Lys Asn Glu Asn Asp Gln Tyr Ile Tyr Met Gly Glu Pro
    1940                1945                1950

Leu Glu Asn Asp Glu Asp Cys Ala His Trp Lys Glu Ala Lys Met
    1955                1960                1965

Leu Leu Asp Asn Ile Asn Thr Pro Glu Gly Ile Ile Pro Ser Met
    1970                1975                1980

Phe Glu Pro Glu Arg Glu Lys Val Asp Ala Ile Asp Gly Glu Tyr
    1985                1990                1995
```

```
Arg Leu Arg Gly Glu Ala Arg Lys Thr Phe Val Asp Leu Met Arg
2000                2005                2010

Arg Gly Asp Leu Pro Val Trp Leu Ala Tyr Arg Val Ala Ala Glu
    2015                2020                2025

Gly Ile Asn Tyr Ala Asp Arg Arg Trp Cys Phe Asp Gly Val Lys
2030                2035                2040

Asn Asn Gln Ile Leu Glu Glu Asn Val Glu Val Glu Ile Trp Thr
    2045                2050                2055

Lys Glu Gly Glu Arg Lys Lys Leu Lys Pro Arg Trp Leu Asp Ala
2060                2065                2070

Arg Ile Tyr Ser Asp Pro Leu Ala Leu Lys Glu Phe Lys Glu Phe
    2075                2080                2085

Ala Ala Gly Arg Lys Ser Leu Thr Leu Asn Leu Ile Thr Glu Met
2090                2095                2100

Gly Arg Leu Pro Thr Phe Met Thr Gln Lys Ala Arg Asp Ala Leu
    2105                2110                2115

Asp Asn Leu Ala Val Leu His Thr Ala Glu Ala Gly Gly Arg Ala
2120                2125                2130

Tyr Asn His Ala Leu Ser Glu Leu Pro Glu Thr Leu Glu Thr Leu
    2135                2140                2145

Leu Leu Leu Thr Leu Leu Ala Thr Val Thr Gly Gly Ile Phe Leu
2150                2155                2160

Phe Leu Met Ser Ala Arg Gly Ile Gly Lys Met Thr Leu Gly Met
    2165                2170                2175

Cys Cys Ile Ile Thr Ala Ser Ile Leu Leu Trp Tyr Ala Gln Ile
2180                2185                2190

Gln Pro His Trp Ile Ala Ala Ser Ile Ile Leu Glu Phe Phe Leu
    2195                2200                2205

Ile Val Leu Leu Ile Pro Glu Pro Glu Lys Gln Arg Thr Pro Gln
2210                2215                2220

Asp Asn Gln Leu Thr Tyr Val Val Ile Ala Ile Leu Thr Val Val
    2225                2230                2235

Ala Ala Thr Met Ala Asn Glu Met Gly Phe Leu Glu Lys Thr Lys
2240                2245                2250

Lys Asp Leu Gly Leu Gly Ser Ile Ala Thr Gln Gln Pro Glu Ser
    2255                2260                2265

Asn Ile Leu Asp Ile Asp Leu Arg Pro Ala Ser Ala Trp Thr Leu
2270                2275                2280

Tyr Ala Val Ala Thr Thr Phe Val Thr Pro Met Leu Arg His Ser
    2285                2290                2295

Ile Glu Asn Ser Ser Val Asn Val Ser Leu Thr Ala Ile Ala Asn
2300                2305                2310

Gln Ala Thr Val Leu Met Gly Leu Gly Lys Gly Trp Pro Leu Ser
    2315                2320                2325

Lys Met Asp Ile Gly Val Pro Leu Leu Ala Ile Gly Cys Tyr Ser
2330                2335                2340

Gln Val Asn Pro Ile Thr Leu Thr Ala Ala Leu Phe Leu Leu Val
    2345                2350                2355

Ala His Tyr Ala Ile Ile Gly Pro Gly Leu Gln Ala Lys Ala Thr
2360                2365                2370

Arg Glu Ala Gln Lys Arg Ala Ala Ala Gly Ile Met Lys Asn Pro
    2375                2380                2385
```

-continued

```
Thr Val Asp Gly Ile Thr Val Ile Asp Leu Asp Pro Ile Pro Tyr
    2390            2395            2400

Asp Pro Lys Phe Glu Lys Gln Leu Gly Gln Val Met Leu Leu Val
    2405            2410            2415

Leu Cys Val Thr Gln Val Leu Met Met Arg Thr Thr Trp Ala Leu
    2420            2425            2430

Cys Glu Ala Leu Thr Leu Ala Thr Gly Pro Ile Ser Thr Leu Trp
    2435            2440            2445

Glu Gly Asn Pro Gly Arg Phe Trp Asn Thr Thr Ile Ala Val Ser
    2450            2455            2460

Met Ala Asn Ile Phe Arg Gly Ser Tyr Leu Ala Gly Ala Gly Leu
    2465            2470            2475

Leu Phe Ser Ile Met Lys Asn Thr Thr Asn Thr Arg Arg Gly Thr
    2480            2485            2490

Gly Asn Ile Gly Glu Thr Leu Gly Glu Lys Trp Lys Ser Arg Leu
    2495            2500            2505

Asn Ala Leu Gly Lys Ser Glu Phe Gln Ile Tyr Lys Lys Ser Gly
    2510            2515            2520

Ile Gln Glu Val Asp Arg Thr Leu Ala Lys Glu Gly Ile Lys Arg
    2525            2530            2535

Gly Glu Thr Asp His His Ala Val Ser Arg Gly Ser Ala Lys Leu
    2540            2545            2550

Arg Trp Phe Val Glu Arg Asn Met Val Thr Pro Glu Gly Lys Val
    2555            2560            2565

Val Asp Leu Gly Cys Gly Arg Gly Gly Trp Ser Tyr Tyr Cys Gly
    2570            2575            2580

Gly Leu Lys Asn Val Arg Glu Val Lys Gly Leu Thr Lys Gly Gly
    2585            2590            2595

Pro Gly His Glu Glu Pro Ile Pro Met Ser Thr Tyr Gly Trp Asn
    2600            2605            2610

Leu Val Arg Leu Gln Ser Gly Val Asp Val Phe Phe Ile Pro Pro
    2615            2620            2625

Glu Lys Cys Asp Thr Leu Leu Cys Asp Ile Gly Glu Ser Ser Pro
    2630            2635            2640

Asn Pro Thr Val Glu Ala Gly Arg Thr Leu Arg Val Leu Asn Leu
    2645            2650            2655

Val Glu Asn Trp Leu Asn Asn Asn Thr Gln Phe Cys Ile Lys Val
    2660            2665            2670

Leu Asn Pro Tyr Met Pro Ser Val Ile Glu Lys Met Glu Ala Leu
    2675            2680            2685

Gln Arg Lys Tyr Gly Gly Ala Leu Val Arg Asn Pro Leu Ser Arg
    2690            2695            2700

Asn Ser Thr His Glu Met Tyr Trp Val Ser Asn Ala Ser Gly Asn
    2705            2710            2715

Ile Val Ser Ser Val Asn Met Ile Ser Arg Met Leu Ile Asn Arg
    2720            2725            2730

Phe Thr Met Arg Tyr Lys Lys Ala Thr Tyr Glu Pro Asp Val Asp
    2735            2740            2745

Leu Gly Ser Gly Thr Arg Asn Ile Gly Ile Glu Ser Glu Ile Pro
    2750            2755            2760

Asn Leu Asp Ile Ile Gly Lys Arg Ile Glu Lys Ile Lys Gln Glu
    2765            2770            2775

His Glu Thr Ser Trp His Tyr Asp Gln Asp His Pro Tyr Lys Thr
```

```
                2780                2785                2790
Trp Ala Tyr His Gly Ser Tyr Glu Thr Lys Gln Thr Gly Ser Ala
    2795                2800                2805

Ser Ser Met Val Asn Gly Val Val Arg Leu Leu Thr Lys Pro Trp
    2810                2815                2820

Asp Val Val Pro Met Val Thr Gln Met Ala Met Thr Asp Thr Thr
    2825                2830                2835

Pro Phe Gly Gln Gln Arg Val Phe Lys Glu Lys Val Asp Thr Arg
    2840                2845                2850

Thr Gln Glu Pro Lys Glu Gly Thr Lys Lys Leu Met Lys Ile Thr
    2855                2860                2865

Ala Glu Trp Leu Trp Lys Glu Leu Gly Lys Lys Lys Thr Pro Arg
    2870                2875                2880

Met Cys Thr Arg Glu Glu Phe Thr Arg Lys Val Arg Ser Asn Ala
    2885                2890                2895

Ala Leu Gly Ala Ile Phe Thr Asp Glu Asn Lys Trp Lys Ser Ala
    2900                2905                2910

Arg Glu Ala Val Glu Asp Ser Arg Phe Trp Glu Leu Val Asp Lys
    2915                2920                2925

Glu Arg Asn Leu His Leu Glu Gly Lys Cys Glu Thr Cys Val Tyr
    2930                2935                2940

Asn Met Met Gly Lys Arg Glu Lys Lys Leu Gly Glu Phe Gly Lys
    2945                2950                2955

Ala Lys Gly Ser Arg Ala Ile Trp Tyr Met Trp Leu Gly Ala Arg
    2960                2965                2970

Phe Leu Glu Phe Glu Ala Leu Gly Phe Leu Asn Glu Asp His Trp
    2975                2980                2985

Phe Ser Arg Glu Asn Ser Leu Ser Gly Val Glu Gly Glu Gly Leu
    2990                2995                3000

His Lys Leu Gly Tyr Ile Leu Arg Asp Val Ser Lys Lys Glu Gly
    3005                3010                3015

Gly Ala Met Tyr Ala Asp Asp Thr Ala Gly Trp Asp Thr Lys Ile
    3020                3025                3030

Thr Leu Glu Asp Leu Lys Asn Glu Glu Met Val Thr Asn His Met
    3035                3040                3045

Glu Gly Glu His Lys Lys Leu Ala Glu Ala Ile Phe Lys Leu Thr
    3050                3055                3060

Tyr Gln Asn Lys Val Val Arg Val Gln Arg Pro Thr Pro Arg Gly
    3065                3070                3075

Thr Val Met Asp Ile Ile Ser Arg Arg Asp Gln Arg Gly Ser Gly
    3080                3085                3090

Gln Val Gly Thr Tyr Gly Leu Asn Thr Phe Thr Asn Met Glu Ala
    3095                3100                3105

Gln Leu Ile Arg Gln Met Glu Gly Glu Gly Val Phe Lys Ser Ile
    3110                3115                3120

Gln His Leu Thr Ile Thr Glu Glu Ile Ala Val Gln Asn Trp Leu
    3125                3130                3135

Ala Arg Val Gly Arg Glu Arg Leu Ser Arg Met Ala Ile Ser Gly
    3140                3145                3150

Asp Asp Cys Val Val Lys Pro Leu Asp Asp Arg Phe Ala Ser Ala
    3155                3160                3165

Leu Thr Ala Leu Asn Asp Met Gly Lys Ile Arg Lys Asp Ile Gln
    3170                3175                3180
```

Gln Trp Glu Pro Ser Arg Gly Trp Asn Asp Trp Thr Gln Val Pro
    3185                3190                3195

Phe Cys Ser His His Phe His Glu Leu Ile Met Lys Asp Gly Arg
    3200                3205                3210

Val Leu Val Val Pro Cys Arg Asn Gln Asp Glu Leu Ile Gly Arg
    3215                3220                3225

Ala Arg Ile Ser Gln Gly Ala Gly Trp Ser Leu Arg Glu Thr Ala
    3230                3235                3240

Cys Leu Gly Lys Ser Tyr Ala Gln Met Trp Ser Leu Met Tyr Phe
    3245                3250                3255

His Arg Arg Asp Leu Arg Leu Ala Ala Asn Ala Ile Cys Ser Ala
    3260                3265                3270

Val Pro Ser His Trp Val Pro Thr Ser Arg Thr Thr Trp Ser Ile
    3275                3280                3285

His Ala Lys His Glu Trp Met Thr Thr Glu Asp Met Leu Thr Val
    3290                3295                3300

Trp Asn Arg Val Trp Ile Gln Glu Asn Pro Trp Met Glu Asp Lys
    3305                3310                3315

Thr Pro Val Glu Thr Trp Glu Glu Ile Pro Tyr Leu Gly Lys Arg
    3320                3325                3330

Glu Asp Gln Trp Cys Gly Ser Leu Ile Gly Leu Thr Ser Arg Ala
    3335                3340                3345

Thr Trp Ala Lys Asn Ile Gln Ala Ala Ile Asn Gln Val Arg Ser
    3350                3355                3360

Leu Ile Gly Asn Glu Glu Tyr Thr Asp Tyr Met Pro Ser Met Lys
    3365                3370                3375

Arg Phe Arg Arg Glu Glu Glu Glu Ala Gly Val Leu Trp
    3380                3385                3390

<210> SEQ ID NO 3
<211> LENGTH: 10723
<212> TYPE: DNA
<213> ORGANISM: Dengue virus
<220> FEATURE:
<221> NAME/KEY: misc_feature
<222> LOCATION: (1)..(10723)
<223> OTHER INFORMATION: Wild-type DEN2 strain 16681

<400> SEQUENCE: 3
agttgttagt ctacgtggac cgacaaagac agattctttg agggagctaa gctcaacgta      60
gttctaacag ttttttaatt agagagcaga tctctgatga ataaccaacg aaaaaaggcg     120
aaaaacacgc ctttcaatat gctgaaacgc gagagaaacc gcgtgtcgac tgtgcaacag     180
ctgacaaaga gattctcact tggaatgctg cagggacgag gaccattaaa actgttcatg     240
gccctggtgg cgttccttcg tttcctaaca atcccaccaa cagcagggat attgaagaga     300
tggggaacaa ttaaaaaatc aaaagctatt aatgttttga gagggttcag aaagagaatt     360
ggaaggatgc tgaacatctt gaataggaga cgcagatctg caggcatgat cattatgctg     420
attccaacag tgatggcgtt ccatttaacc acacgtaacg gagaaccaca catgatcgtc     480
agcagacaag agaagggaa aagtcttctg tttaaaacag aggatggcgt gaacatgtgt     540
accctcatgg ccatggacct tggtgaattg tgtgaagaca caatcacgta caagtgtccc     600
cttctcaggc agaatgagcc agaagacata gactgttggt gcaactctac gtccacgtgg     660
gtaacttatg ggacgtgtac caccatggga gaacatagaa gagaaaaaag atcagtggca     720

```
ctcgttccac atgtgggaat gggactggag acacgaactg aaacatggat gtcatcagaa      780
ggggcctgga acatgtcca gagaattgaa acttggatct tgagacatcc aggcttcacc      840
atgatggcag caatcctggc atacaccata ggaacgacac atttccaaag agccctgatt     900
ttcatcttac tgacagctgt cactccttca atgacaatgc gttgcatagg aatgtcaaat     960
agagactttg tggaaggggt ttcaggagga agctgggttg acatagtctt agaacatgga    1020
agctgtgtga cgacgatggc aaaaaacaaa ccaacattgg attttgaact gataaaaaca    1080
gaagccaaac agcctgccac cctaaggaag tactgtatag aggcaaagct aaccaacaca    1140
acaacagaat ctcgctgccc aacacaaggg gaacccagcc taaatgaaga gcaggacaaa    1200
aggttcgtct gcaaacactc catggtagac agaggatggg gaaatggatg tggactattt    1260
ggaaagggag gcattgtgac ctgtgctatg ttcagatgca aaaagaacat ggaaggaaaa    1320
gttgtgcaac cagaaaactt ggaatacacc attgtgataa cacctcactc aggggaagag    1380
catgcagtcg gaaatgacac aggaaaacat ggcaaggaaa tcaaaataac accacagagt    1440
tccatcacag aagcagaatt gacaggttat ggcactgtca aatggagtg ctctccaaga    1500 acgggcctcg acttcaatga gatggtgttg ctgcagatgg aaaataaagc ttggctggtg    1560
cacaggcaat ggttcctaga cctgccgtta ccatggttgc ccggagcgga cacacaaggg    1620
tcaaattgga tacagaaaga gacattggtc actttcaaaa atcccatgc gaagaaacag    1680 gatgttgttg ttttaggatc ccaagaaggg gccatgcaca cagcacttac aggggccaca    1740
gaaatccaaa tgtcatcagg aaacttactc ttcacaggac atctcaagtg caggctgaga    1800
atggacaagc tacagctcaa aggaatgtca tactctatgt gcacaggaaa gtttaaagtt    1860
gtgaaggaaa tagcagaaac acaacatgga acaatagtta tcagagtgca atatgaaggg    1920
gacggctctc catgcaagat ccctttttgag ataatggatt tggaaaaaag acatgtctta    1980
ggtcgcctga ttacagtcaa cccaattgtg acagaaaaag atagcccagt caacatagaa    2040
gcagaacctc cattcggaga cagctacatc atcataggag tagagccggg acaactgaag    2100
ctcaactggt ttaagaaagg aagttctatc ggccaaatgt ttgagacaac aatgagggggg   2160 gcgaagagaa tggccatttt aggtgacaca gcctgggatt ttggatcctt gggaggagtg    2220
tttacatcta taggaaaggc tctccaccaa gtctttggag caatctatgg agctgccttc    2280 agtgggggttt catggactat gaaaatcctc ataggagtca ttatcacatg gataggaatg    2340
aattcacgca gcacctcact gtctgtgaca ctagtattgg tgggaattgt gacactgtat    2400
ttgggagtca tggtgcaggc cgatagtggt tgcgttgtga ctggaaaaaa caaagaactg    2460
aaatgtggca gtgggatttt catcacagac aacgtgcaca catggacaga acaatacaag    2520
ttccaaccag aatccccttc aaaactagct tcagctatcc agaaagccca tgaagagggc    2580
atttgtggaa tccgctcagt aacaagactg gagaatctga tgtggaaaca aataacacca    2640
gaattgaatc acattctatc agaaaatgag gtgaagttaa ctattatgac aggagacatc    2700
aaaggaatca tgcaggcagg aaaacgatct ctgcggcctc agcccactga gctgaagtat    2760
tcatggaaaa catggggcaa agcaaaaatg ctctctacag agtctcataa ccagaccttt    2820
ctcattgatg gccccgaaac agcagaatgc cccaacacaa atagagcttg gaattcgttg    2880
gaagttgaag actatggctt tggagtattc accaccaata tatggctaaa attgaaagaa    2940
aaacaggatg tattctgcga ctcaaaactc atgtcagcgg ccataaaaga caacagagcc    3000
gtccatgccg atatgggtta ttggatagaa agtgcactca tgacacatg gaagatagag    3060 aaagcctctt tcattgaagt taaaaactgc cactggccaa aatcacacac cctctggagc    3120
```

```
aatggagtgc tagaaagtga gatgataatt ccaaagaatc tcgctggacc agtgtctcaa    3180
cacaactata gaccaggcta ccatacacaa ataacaggac catggcatct aggtaagctt    3240
gagatggact ttgatttctg tgatggaaca acagtggtag tgactgagga ctgcggaaat    3300
agaggaccct ctttgagaac aaccactgcc tctggaaaac tcataacaga atggtgctgc    3360
cgatcttgca cattaccacc gctaagatac agaggtgagg atgggtgctg gtacgggatg    3420
gaaatcagac cattgaagga gaaagaagag aatttggtca actccttggt cacagctgga    3480
catgggcagg tcgacaactt ttcactagga gtcttgggaa tggcattgtt cctggaggaa    3540
atgcttagga cccgagtagg aacgaaacat gcaatactac tagttgcagt ttcttttgtg    3600
acattgatca cagggaacat gtcctttaga gacctgggaa gagtgatggt tatggtaggc    3660
gccactatga cggatgacat aggtatgggc gtgacttatc ttgccctact agcagccttc    3720
aaagtcagac caacttttgc agctggacta ctcttgagaa agctgacctc caaggaattg    3780
atgatgacta ctataggaat tgtactcctc tcccagagca ccataccaga gaccattctt    3840
gagttgactg atgcgttagc cttaggcatg atggtcctca aaatggtgag aaatatggaa    3900
aagtatcaat tggcagtgac tatcatggct atcttgtgcg tcccaaacgc agtgatatta    3960
caaaacgcat ggaaagtgag ttgcacaata ttggcagtgg tgtccgtttc cccactgctc    4020
ttaacatcct cacagcaaaa aacagattgg ataccattag cattgacgat caaaggtctc    4080
aatccaacag ctattttttct aacaacccctc tcaagaacca gcaagaaaag gagctggcca    4140
ttaaatgagg ctatcatggc agtcgggatg gtgagcattt tagccagttc tctcctaaaa    4200
aatgatattc ccatgacagg accattagtg gctggagggc tcctcactgt gtgctacgtg    4260
ctcactggac gatcggccga tttggaactg gagagagcag ccgatgtcaa atgggaagac    4320
caggcagaga tatcaggaag cagtccaatc ctgtcaataa caatatcaga gatggttagc    4380
atgtcgataa aaaatgaaga ggaagaacaa acactgacca tactcattag aacaggattg    4440
ctggtgatct caggacttttt tcctgtatca ataccaatca cggcagcagc atggtacctg    4500
tgggaagtga agaaacaacg ggccggagta ttgtgggatg ttccttcacc cccacccatg    4560
ggaaaggctg aactggaaga tggagcctat agaattaagc aaaaagggat tcttggatat    4620
tcccagatcg gagccggagt ttacaaagaa ggaacattcc atacaatgtg gcatgtcaca    4680
cgtggcgctg ttctaatgca taaggaaaag aggattgaac catcatgggc ggacgtcaag    4740
aaagacctaa tatcatatgg aggaggctgg aagttagaag gagaatggaa ggaaggagaa    4800
gaagtccagg tattggcact ggagcctgga aaaaatccaa gagccgtcca aacgaaacct    4860 ggtctttttca aaccaacgc cggaacaata ggtgctgtat ctctggactt ttctcctgga    4920
acgtcaggat ctccaattat cgacaaaaaa ggaaaagttg tgggtcttta tggtaatggt    4980
gttgttacaa ggagtggagc atatgtgagt gctatagccc agactgaaaa aagcattgaa    5040
gacaacccag atcgaagaa tgacattttc cgaaagagaa gactgaccat catgaccctc    5100
cacccaggag cgggaaagac gaagagatac cttccggcca tagtcagaga agctataaaa    5160
cggggtttga gaacattaat cttggcccccc actagagttg tggcagctga aatggaggaa    5220
gcccttagag gacttccaat aagataccag accccagcca tcagagctga gcacaccggg    5280
cgggagattg tggacctaat gtgtcatgcc acatttacca tgaggctgct atcaccagtt    5340
agagtgccaa actacaacct gattatcatg gacgaagccc atttcacaga cccagcaagt    5400
atagcagcta gaggatacat ctcaactcga gtggagatgg tgaggcagc tgggattttt    5460
```

```
atgacagcca ctcccccggg aagcagagac ccatttcctc agagcaatgc accaatcata    5520
gatgaagaaa gagaaatccc tgaacgttcg tggaattccg acatgaatg ggtcacggat     5580 tttaaaggga agactgtttg gttcgttcca agtataaaag caggaaatga tatagcagct    5640
tgcctgagga aaaatggaaa gaaagtgata caactcagta ggaagacctt tgattctgag    5700
tatgtcaaga ctagaaccaa tgattgggac ttcgtggtta caactgacat ttcagaaatg    5760
ggtgccaatt tcaaggctga gagggttata gaccccagac gctgcatgaa accagtcata    5820
ctaacagatg gtgaagagcg ggtgattctg gcaggaccta tgccagtgac ccactctagt    5880
gcagcacaaa aagagggag aataggaaga aatccaaaaa atgagaatga ccagtacata     5940
tacatggggg aacctctgga aaatgatgaa gactgtgcac actggaaaga agctaaaatg    6000
ctcctagata acatcaacac gccagaagga atcattccta gcatgttcga accagagcgt    6060
gaaaaggtgg atgccattga tggcgaatac cgcttgagag gagaagcaag gaaaaccttt    6120 gtagactta a tgagaagag g agacctacca gtctggttgg cctacagagt ggcagctgaa    6180
ggcatcaact acgcagacag aaggtggtgt tttgatggag tcaagaacaa ccaaatccta    6240
gaagaaaacg tggaagttga aatctggaca aaagaagggg aaaggaagaa attgaaaccc    6300
agatggttgg atgctaggat ctattctgac ccactggcgc taaaagaatt taaggaattt    6360
gcagccggaa gaaagtctct gaccctgaac ctaatcacag aaatgggtag gctcccaacc    6420
ttcatgactc agaaggcaag agacgcactg gacaacttag cagtgctgca cacggctgag    6480
gcaggtggaa gggcgtacaa ccatgctctc agtgaactgc cggagaccct ggagacattg    6540
cttttactga cacttctggc tacagtcacg ggagggatct ttttattctt gatgagcgga    6600
aggggcatag ggaagatgac cctgggaatg tgctgcataa tcacggctag catcctccta    6660
tggtacgcac aaatacagcc acactggata gcagcttcaa taatactgga gttttttctc    6720
atagttttgc ttattccaga acctgaaaaa cagagaacac cccaagacaa ccaactgacc    6780
tacgttgtca tagccatcct cacagtggtg gccgcaacca tggcaaacga gatgggtttc    6840
ctagaaaaaa cgaagaaaga tctcggattg ggaagcattg caacccagca acccgagagc    6900
aacatcctgg acatagatct acgtcctgca tcagcatgga cgctgtatgc cgtggccaca    6960
acatttgtta caccaatgtt gagacatagc attgaaaatt cctcagtgaa tgtgtcccta    7020
acagctatag ccaaccaagc cacagtgtta atgggtctcg ggaaaggatg gccattgtca    7080
aagatggaca tcggagttcc ccttctcgcc attggatgct actcacaagt caaccccata    7140
actctcacag cagctcttt t cttattggta gcacattatg ccatcatagg gccaggactc    7200
caagcaaaag caaccagaga agctcagaaa agagcagcgg cgggcatcat gaaaaaccca    7260
actgtcgatg gaataacagt gattgaccta gatccaatac cttatgatcc aaagtttgaa    7320
aagcagttgg gacaagtaat gctcctagtc ctctgcgtga ctcaagtatt gatgatgagg    7380
actacatggg ctctgtgtga ggctttaacc ttagctaccg ggcccatctc acattgtgg     7440 gaaggaaatc cagggaggtt ttggaacact accattgcgg tgtcaatggc taacattttt    7500
agagggagtt acttggccgg agctggactt ctctttt cta ttatgaagaa cacaaccaac    7560
acaagaaggg gaactggcaa cataggagag acgcttggag agaaatggaa agccgattg     7620 aacgcattgg gaaaaagtga attccagatc tacaagaaaa gtggaatcca ggaagtggat    7680
agaaccttag caaagaagg cattaaaaga ggagaaacgg accatcacgc tgtgtcgcga    7740
ggctcagcaa aactgagatg gttcgttgag agaaacatgg tcacaccaga agggaaagta    7800 gtggaccteg gttgtggcag aggaggctgg tcatactatt gtggaggact aaagaatgta    7860
```

```
agagaagtca aaggcctaac aaaaggagga ccaggacacg aagaacccat ccccatgtca    7920
acatatgggt ggaatctagt gcgtcttcaa agtggagttg acgttttctt catcccgcca    7980
gaaaagtgtg acacattatt gtgtgacata ggggagtcat caccaaatcc cacagtggaa    8040
gcaggacgaa cactcagagt ccttaactta gtagaaaatt ggttgaacaa caacactcaa    8100
ttttgcataa aggttctcaa cccatatatg ccctcagtca tagaaaaaat ggaagcacta    8160
caaaggaaat atggaggagc cttagtgagg aatccactct cacgaaactc cacacatgag    8220
atgtactggg tatccaatgc ttccgggaac atagtgtcat cagtgaacat gatttcaagg    8280
atgttgatca acagatttac aatgagatac aagaaagcca cttacgagcc ggatgttgac    8340
ctcggaagcg gaacccgtaa catcgggatt gaaagtgaga taccaaacct agatataatt    8400
gggaaaagaa tagaaaaaat aaagcaagag catgaaacat catggcacta tgaccaagac    8460
cacccataca aaacgtgggc ataccatggt agctatgaaa caaaacagac tggatcagca    8520
tcatccatgg tcaacggagt ggtcaggctg ctgacaaaac cttgggacgt cgtccccatg    8580
gtgacacaga tggcaatgac agacacgact ccatttggac aacagcgcgt ttttaaagag    8640
aaagtggaca cgagaaccca agaaccgaaa gaaggcacga agaaactaat gaaaataaca    8700
gcagagtggc tttgaaaaga attagggaag aaaagacac ccaggatgtg caccagagaa    8760
gaattcacaa gaaaggtgag aagcaatgca gccttggggg ccatattcac tgatgagaac    8820
aagtggaagt cggcacgtga ggctgttgaa gatagtaggt tttgggagct ggttgacaag    8880
gaaaggaatc tccatcttga aggaaagtgt gaaacatgtg tgtacaacat gatgggaaaa    8940
agagagaaga agctagggga attcggcaag gcaaaggca gcagagccat atggtacatg    9000
tggcttggag cacgcttctt agagtttgaa gccctaggat tcttaaatga agatcactgg    9060
ttctccagag agaactccct gagtggagtg aaggagaag ggctgcacaa gctaggttac    9120
attctaagag acgtgagcaa gaaagaggga ggagcaatgt atgccgatga caccgcagga    9180
tgggatacaa gaatcacact agaagaccta aaaaatgaag aaatggtaac aaaccacatg    9240
gaaggagaac acaagaaact agccgaggcc attttcaaac taacgtacca aaacaaggtg    9300
gtgcgtgtgc aaagaccaac accaagaggc acagtaatgg acatcatatc gagaagagac    9360
caaagaggta gtggacaagt tggcacctat ggactcaata cttttaccaa tatggaagcc    9420
caactaatca gacagatgga gggagaagga gtctttaaaa gcattcagca cctaacaatc    9480
acagaagaaa tcgctgtgca aaactggtta gcaagagtgg ggcgcgaaag gttatcaaga    9540
atggccatca gtgagatgaa ttgtgttgtg aaaccttag atgacaggtt cgcaagcgct    9600
ttaacagctc taaatgacat gggaaagatt aggaaagaca tacaacaatg gaaccttca    9660 agaggatgga tgattggac acaagtgccc ttctgttcac accatttcca tgagttaatc    9720
atgaaagacg gtcgcgtact cgttgttcca tgtagaaacc aagatgaact gattggcaga    9780
gcccgaatct cccaaggagc agggtggtct ttgcgggaga cggcctgttt ggggaagtct    9840
tacgcccaaa tgtggagctt gatgtacttc cacagacgcg acctcaggct ggcggcaaat    9900
gctatttgct cggcagtacc atcacattgg gttccaacaa gtcgaacaac ctggtccata    9960
catgctaaac atgaatggat gacaacgaa gacatgctga cagtctggaa cagggtgtgg   10020
attcaagaaa acccatggat ggaagacaaa actccagtgg aatcatggga ggaaatccca   10080
tacttgggga aaagagaaga ccaatggtgc ggctcattga ttgggttaac aagcagggc   10140 acctgggcaa agaacatcca agcagcaata aatcaagtta gatcccttat aggcaatgaa   10200
```

-continued

```
gaatacacag attacatgcc atccatgaaa agattcagaa gagaagagga agaagcagga      10260
gttctgtggt agaaagcaaa actaacatga aacaaggcta gaagtcaggt cggattaagc      10320
catagtacgg aaaaaactat gctacctgtg agccccgtcc aaggacgtta aaagaagtca      10380
ggccatcata aatgccatag cttgagtaaa ctatgcagcc tgtagctcca cctgagaagg      10440
tgtaaaaaat ccgggaggcc acaaaccatg gaagctgtac gcatggcgta gtggactagc      10500
ggttagagga gacccctccc ttacaaatcg cagcaacaat gggggcccaa ggcgagatga      10560
agctgtagtc tcgctggaag gactagaggt tagaggagac ccccccgaaa caaaaaacag      10620
catattgacg ctgggaaaga ccagagatcc tgctgtctcc tcagcatcat tccaggcaca      10680
gaacgccaga aaatggaatg gtgctgttga atcaacaggt tct                        10723
```

<210> SEQ ID NO 4
<211> LENGTH: 37
<212> TYPE: DNA
<213> ORGANISM: Artificial sequence
<220> FEATURE:
<223> OTHER INFORMATION: primer

<400> SEQUENCE: 4
gttttcccag tcacgacacg tggaccgaca aagacag                               37

<210> SEQ ID NO 5
<211> LENGTH: 36
<212> TYPE: DNA
<213> ORGANISM: Artificial sequence
<220> FEATURE:
<223> OTHER INFORMATION: primer

<400> SEQUENCE: 5
aacagctatg accatgttcc tcctgaaacc ccttcc                                36

<210> SEQ ID NO 6
<211> LENGTH: 36
<212> TYPE: DNA
<213> ORGANISM: Artificial sequence
<220> FEATURE:
<223> OTHER INFORMATION: primer

<400> SEQUENCE: 6
gttttcccag tcacgacatc acgtacaagt gtcccc                                36

<210> SEQ ID NO 7
<211> LENGTH: 37
<212> TYPE: DNA
<213> ORGANISM: Artificial sequence
<220> FEATURE:
<223> OTHER INFORMATION: primer

<400> SEQUENCE: 7
aacagctatg accatgagca acaccatctc attgaag                               37

<210> SEQ ID NO 8
<211> LENGTH: 42
<212> TYPE: DNA
<213> ORGANISM: Artificial
<220> FEATURE:
<223> OTHER INFORMATION: primer

<400> SEQUENCE: 8
gttttcccag tcacgactgc aaccagaaaa cttggaatac ac                         42

<210> SEQ ID NO 9
<211> LENGTH: 39
<212> TYPE: DNA
<213> ORGANISM: Artificial sequence
<220> FEATURE:
<223> OTHER INFORMATION: primer

<400> SEQUENCE: 9
aacagctatg accatggctc catagattgc tccaaagac                              39

<210> SEQ ID NO 10
<211> LENGTH: 41
<212> TYPE: DNA
<213> ORGANISM: Artificial sequence
<220> FEATURE:
<223> OTHER INFORMATION: primer

<400> SEQUENCE: 10
gttttcccag tcacgacccc agtcaacata gaagcagaac c                           41

<210> SEQ ID NO 11
<211> LENGTH: 40
<212> TYPE: DNA
<213> ORGANISM: Artificial sequence
<220> FEATURE:
<223> OTHER INFORMATION: primer

<400> SEQUENCE: 11
aacagctatg accatgccaa agccatagtc ttcaacttcc                             40

<210> SEQ ID NO 12
<211> LENGTH: 36
<212> TYPE: DNA
<213> ORGANISM: Artificial sequence
<220> FEATURE:
<223> OTHER INFORMATION: primer

<400> SEQUENCE: 12
gttttcccag tcacgacatc atgcaggcag gaaaac                                 36

<210> SEQ ID NO 13
<211> LENGTH: 37
<212> TYPE: DNA
<213> ORGANISM: Artificial sequence
<220> FEATURE:
<223> OTHER INFORMATION: primer

<400> SEQUENCE: 13
aacagctatg accatgacca taaccatcac tcttccc                                37

<210> SEQ ID NO 14
<211> LENGTH: 37
<212> TYPE: DNA
<213> ORGANISM: Artificial sequence
<220> FEATURE:
<223> OTHER INFORMATION: primer

<400> SEQUENCE: 14
aacagctatg accatgacca taaccatcac tcttccc                                37

<210> SEQ ID NO 15
<211> LENGTH: 36
<212> TYPE: DNA
<213> ORGANISM: Artificial sequence
<220> FEATURE:
<223> OTHER INFORMATION: primer

<400> SEQUENCE: 15
aacagctatg accatggctc tctccagttc caaatc    36

<210> SEQ ID NO 16
<211> LENGTH: 38
<212> TYPE: DNA
<213> ORGANISM: Artificial sequence
<220> FEATURE:
<223> OTHER INFORMATION: priemr

<400> SEQUENCE: 16
gttttcccag tcacgacaag aaccagcaag aaaaggag    38

<210> SEQ ID NO 17
<211> LENGTH: 38
<212> TYPE: DNA
<213> ORGANISM: Artificial sequence
<220> FEATURE:
<223> OTHER INFORMATION: primer

<400> SEQUENCE: 17
aacagctatg accatgcacc attaccataa agacccac    38

<210> SEQ ID NO 18
<211> LENGTH: 37
<212> TYPE: DNA
<213> ORGANISM: Artificial sequence
<220> FEATURE:
<223> OTHER INFORMATION: primer

<400> SEQUENCE: 18
gttttcccag tcacgacttg aaccatcatg ggcggac    37

<210> SEQ ID NO 19
<211> LENGTH: 41
<212> TYPE: DNA
<213> ORGANISM: Artificial sequence
<220> FEATURE:
<223> OTHER INFORMATION: primer

<400> SEQUENCE: 19
aacagctatg accatgtcct gcttttatac ttggaacgaa c    41

<210> SEQ ID NO 20
<211> LENGTH: 36
<212> TYPE: DNA
<213> ORGANISM: Artificial sequence
<220> FEATURE:
<223> OTHER INFORMATION: primer

<400> SEQUENCE: 20
gttttcccag tcacgacaag cccatttcac agaccc    36

<210> SEQ ID NO 21
<211> LENGTH: 38
<212> TYPE: DNA
<213> ORGANISM: Artificial sequence
<220> FEATURE:
<223> OTHER INFORMATION: primer

<400> SEQUENCE: 21
aacagctatg accatgtcaa tttcttcctt tccccttc    38

<210> SEQ ID NO 22
<211> LENGTH: 38

```
<212> TYPE: DNA
<213> ORGANISM: Artificial sequence
<220> FEATURE:
<223> OTHER INFORMATION: primer

<400> SEQUENCE: 22
gttttcccag tcacgacgag aggagaagca aggaaaac                              38

<210> SEQ ID NO 23
<211> LENGTH: 35
<212> TYPE: DNA
<213> ORGANISM: Artificial sequence
<220> FEATURE:
<223> OTHER INFORMATION: primer

<400> SEQUENCE: 23
aacagctatg accatgaggg acacattcac tgagg                                 35

<210> SEQ ID NO 24
<211> LENGTH: 36
<212> TYPE: DNA
<213> ORGANISM: Artificial sequence
<220> FEATURE:
<223> OTHER INFORMATION: primer

<400> SEQUENCE: 24
gttttcccag tcacgacaca gagaacaccc caagac                                36

<210> SEQ ID NO 25
<211> LENGTH: 35
<212> TYPE: DNA
<213> ORGANISM: Artificial sequence
<220> FEATURE:
<223> OTHER INFORMATION: primer

<400> SEQUENCE: 25
aacagctatg accatgtcca cttcctggat tccac                                 35

<210> SEQ ID NO 26
<211> LENGTH: 39
<212> TYPE: DNA
<213> ORGANISM: Artificial sequence
<220> FEATURE:
<223> OTHER INFORMATION: primer

<400> SEQUENCE: 26
gttttcccag tcacgacaca agtaatgctc ctagtcctc                             39

<210> SEQ ID NO 27
<211> LENGTH: 38
<212> TYPE: DNA
<213> ORGANISM: Artificial sequence
<220> FEATURE:
<223> OTHER INFORMATION: primer

<400> SEQUENCE: 27
aacagctatg accatgttca ctgatgacac tatgttcc                              38

<210> SEQ ID NO 28
<211> LENGTH: 37
<212> TYPE: DNA
<213> ORGANISM: Artificial sequence
<220> FEATURE:
<223> OTHER INFORMATION: primer

<400> SEQUENCE: 28
```
gttttcccag tcacgacgtc atcaccaaat cccacag         37

<210> SEQ ID NO 29
<211> LENGTH: 39
<212> TYPE: DNA
<213> ORGANISM: Artificial sequence
<220> FEATURE:
<223> OTHER INFORMATION: priemr

<400> SEQUENCE: 29
aacagctatg accatggctt cttctctctt tttcccatc         39

<210> SEQ ID NO 30
<211> LENGTH: 36
<212> TYPE: DNA
<213> ORGANISM: Artificial sequence
<220> FEATURE:
<223> OTHER INFORMATION: primer

<400> SEQUENCE: 30
gttttcccag tcacgacaag gtgagaagca atgcag         36

<210> SEQ ID NO 31
<211> LENGTH: 37
<212> TYPE: DNA
<213> ORGANISM: Artificial sequence
<220> FEATURE:
<223> OTHER INFORMATION: primer

<400> SEQUENCE: 31
aacagctatg accatgtgga aatggtgtga acagaag         37

<210> SEQ ID NO 32
<211> LENGTH: 39
<212> TYPE: DNA
<213> ORGANISM: Artificial sequence
<220> FEATURE:
<223> OTHER INFORMATION: primer

<400> SEQUENCE: 32
gttttcccag tcacgacgca ttcagcacct aacaatcac         39

<210> SEQ ID NO 33
<211> LENGTH: 35
<212> TYPE: DNA
<213> ORGANISM: Artificial sequence
<220> FEATURE:
<223> OTHER INFORMATION: primer

<400> SEQUENCE: 33
aacagctatg accatgggca tttatgatgg cctga         35

<210> SEQ ID NO 34
<211> LENGTH: 17
<212> TYPE: DNA
<213> ORGANISM: Artificial sequence
<220> FEATURE:
<223> OTHER INFORMATION: primer

<400> SEQUENCE: 34
ccatggaagc tgtacgc         17

<210> SEQ ID NO 35
<211> LENGTH: 36
<212> TYPE: DNA
<213> ORGANISM: Artificial sequence
<220> FEATURE:
<223> OTHER INFORMATION: primer

<400> SEQUENCE: 35
aacagctatg accatgtgat tcaacagcac cattcc 36

<210> SEQ ID NO 36
<211> LENGTH: 17
<212> TYPE: DNA
<213> ORGANISM: Artificial sequence
<220> FEATURE:
<223> OTHER INFORMATION: primer tail

<400> SEQUENCE: 36
gttttcccag tcacgac 17

<210> SEQ ID NO 37
<211> LENGTH: 16
<212> TYPE: DNA
<213> ORGANISM: Artificial sequence
<220> FEATURE:
<223> OTHER INFORMATION: primer tail

<400> SEQUENCE: 37
aacagctatg accatg 16

<210> SEQ ID NO 38
<211> LENGTH: 10723
<212> TYPE: DNA
<213> ORGANISM: Dengue virus
<220> FEATURE:
<221> NAME/KEY: misc_feature
<222> LOCATION: (1)..(10723)
<223> OTHER INFORMATION: LAV2

<400> SEQUENCE: 38
agttgttagt ctacgtggac cgacaaagac agattctttg agggagctaa gctcaatgta 60
gttctaacag ttttttaatt agagagcaga tctctgatga ataaccaacg gaaaaaggcg 120
aaaaacacgc ctttcaatat gctgaaacgc gagagaaacc gcgtgtcgac tgtgcaacag 180
ctgacaaaga gattctcact tggaatgctg cagggacgag gaccattaaa actgttcatg 240
gccctggtgg cgttccttcg tttcctaaca atcccaccaa cagcagggat attgaagaga 300
tggggaacaa ttaaaaaatc aaaagctatt aatgttttga gagggttcag gaaagagatt 360
ggaaggatgc tgaacatctt gaataggaga cgcagatctg caggcatgat cattatgctg 420
attccaacag tgatggcgtt ccatttaacc acacgtaacg gagaaccaca catgatcgtc 480
agcagacaag agaaagggaa aagtcttctg tttaaaacag aggttggcgt gaacatgtgt 540
accctcatgg ccatggacct tggtgaattg tgtgaagaca caatcacgta caagtgtccc 600
cttctcaggc agaatgagcc agaagacata gactgttggt gcaactctac gtccacgtgg 660
gtaacttatg ggacgtgtac caccatggga gaacatagaa gagaaaaaag atcagtggca 720
ctcgttccac atgtgggaat gggactggag acacgaactg aaacatggat gtcatcagaa 780
ggggcctgga aacatgtcca gagaattgaa acttggatct tgagacatcc aggcttcacc 840
atgatggcag caatcctggc atacaccata ggaacgacac atttccaaag agccctgatt 900
ttcatcttac tgacagctgt cactccttca atgacaatgc gttgcatagg aatgtcaaat 960
agagactttg tggaaggggt ttcaggagga agctgggttg acatagtctt agaacatgga 1020
agctgtgtga cgacgatggc aaaaaacaaa ccaacattgg attttgaact gataaaaaca 1080

```
gaagccaaac agcctgccac cctaaggaag tactgtatag aggcaaagct aaccaacaca    1140
acaacagaat ctcgctgccc aacacaaggg gaacccagcc taaatgaaga gcaggacaaa    1200
aggttcgtct gcaaacactc catggtagac agaggatggg gaaatggatg tggactattt    1260
ggaaagggag gcattgtgac ctgtgctatg ttcagatgca aaaagaacat ggaaggaaaa    1320
gttgtgcaac cagaaaactt ggaatacacc attgtgataa cacctcactc aggggaagag    1380
catgcagtcg gaaatgacac aggaaaacat ggcaaggaaa tcaaaataac accacagagt    1440
tccatcacag aagcagaatt gacaggttat ggcactgtca caatggagtg ctctccaaga    1500
acgggcctcg acttcaatga gatggtgttg ctgcagatgg aaaataaagc ttggctggtg    1560
cacaggcaat ggttcctaga cctgccgtta ccatggttgc ccggagcgga cacacaaggg    1620
tcaaattgga tacagaaaga gacattggtc actttcaaaa atccccatgc gaagaaacag    1680
gatgttgttg ttttaggatc ccaagaaggg gccatgcaca cagcacttac aggggccaca    1740
gaaatccaaa tgtcatcagg aaacttactc ttcacaggac atctcaagtg caggctgaga    1800
atggacaagc tacagctcaa aggaatgtca tactctatgt gcacaggaaa gtttaaagtt    1860
gtgaaggaaa tagcagaaac acaacatgga acaatagtta tcagagtgca atatgaaggg    1920
gacggctctc catgcaagat ccctttgag ataatggatt tggaaaaaag acatgtctta    1980
ggtcgcctga ttacagtcaa cccaattgtg acagaaaaag atagcccagt caacatagaa    2040
gcagaacctc catttggaga cagctacatc atcataggag tagagccggg acaactgaag    2100
ctcaactggt ttaagaaagg aagttctatc ggccaaatgt ttgagacaac aatgagggggg    2160
gcgaagagaa tggccatttt aggtgacaca gcctgggatt ttggatcctt gggaggagtg    2220
tttacatcta taggaaaggc tctccaccaa gtctttggag caatctatgg agctgccttc    2280
agtgggttt catggactat gaaaatcctc ataggagtca ttatcacatg gataggaatg    2340
aattcacgca gcacctcact gtctgtgaca ctagtattgg tgggaattgt gacactgtat    2400
ttgggagtca tggtgcaggc cgatagtggt tgcgttgtga ctggaaaaaa caaagaactg    2460
aaatgtggca gtgggatttt catcacagac aacgtgcaca catggacaga acaatacaag    2520
ttccaaccag aatcccccttc aaaactagct tcagctatcc agaaagccca tgaagaggac    2580
atttgtggaa tccgctcagt aacaagactg gagaatctga tgtggaaaca aataacacca    2640
gaattgaatc acattctatc agaaaatgag gtgaagttaa ctattatgac aggagacatc    2700
aaaggaatca tgcaggcagg aaaacgatct ctgcggcctc agcccactga gctgaagtat    2760
tcatggaaaa catggggcaa agcaaaaatg ctctctacag agtctcataa ccagaccttt    2820
ctcattgatg cccccgaaac agcagaatgc cccaacacaa atagagcttg gaattcgttg    2880
gaagttgaag actatggctt tggagtattc accaccaata tatggctaaa attgaaagaa    2940
aaacaggatg tattctgcga ctcaaaactc atgtcagcgg ccataaaaga caacagagcc    3000
gtccatgccg atatgggtta ttggatagaa agtgcactca atgacacatg gaagatagag    3060
aaagcctctt tcattgaagt taaaaactgc cactggccaa aatcacacac cctctggagc    3120
aatggagtgc tagaaagtga gatgataatt ccaaagaatc tcgctggacc agtgtctcaa    3180
cacaactata gaccaggcta ccatacacaa ataacaggac catggcatct aggtaagctt    3240
gagatggact ttgatttctg tgatggaaca acagtggtag tgactgagga ctgcggaaat    3300
agaggaccct ctttgagaac aaccactgcc tctggaaaac tcataacaga atggtgctgc    3360
cgatcttgca cattaccacc gctaagatac agaggtgagg atgggtgctg gtacgggatg    3420
gaaatcagac cattgaagga gaaagaagag aatttggtca actccttggt cacagctgga    3480
```

```
catgggcagg tcgacaactt ttcactagga gtcttgggaa tggcattgtt cctggaggaa    3540
atgcttagga cccgagtagg aacgaaacat gcaatactac tagttgcagt ttcttttgtg    3600
acattgatca cagggaacat gtcctttaga gacctgggaa gagtgatggt tatggtaggc    3660
gccactatga cggatgacat aggtatgggc gtgacttatc ttgccctact agcagccttc    3720
aaagtcagac caacttttgc agctggacta ctcttgagaa agctgacctc caaggaattg    3780
atgatgacta ctataggaat tgtactcctc tcccagagca ccataccaga gaccattctt    3840
gagttgactg atgcgttagc cttaggcatg atggtcctca aaatggtgag aaatatggaa    3900
aagtatcaat tggcagtgac tatcatggct atcttgtgcg tcccaaacgc agtgatatta    3960
caaaacgcat ggaaagtgag ttgcacaata ttggcagtgg tgtccgtttc cccactgttc    4020
ttaacatcct cacagcaaaa aacagattgg ataccattag cattgacgat caaaggtctc    4080
aatccaacag ctattttct aacaacccte tcaagaacca gcaagaaaag gagctggcca    4140
ttaaatgagg ctatcatggc agtcgggatg gtgagcattt tagccagttc tctcctaaaa    4200
aatgatattc ccatgacagg accattagtg gctggagggc tcctcactgt gtgctacgtg    4260
ctcactggac gatcggccga tttgaactg gagagagcag ccgatgtcaa atgggaagac    4320
caggcagaga tatcaggaag cagtccaatc ctgtcaataa caatatcaga gatggtagc    4380 atgtcgataa aaatgaaga ggaagaacaa acactgacca tactcattag aacaggattg    4440
ctggtgatct caggactttt tcctgtatca ataccaatca cggcagcagc atggtacctg    4500
tgggaagtga agaaacaacg ggccggagta ttgtgggatg ttccttcacc cccacccatg    4560
ggaaaggctg aactggaaga tggagcctat agaattaagc aaaaagggat tcttggatat    4620
tcccagatcg gagccggagt ttacaaagaa ggaacattcc atacaatgtg gcatgtcaca    4680
cgtggcgctg ttctaatgca taaaggaaag aggattgaac catcatgggc ggacgtcaag    4740
aaagacctaa tatcatatgg aggaggctgg aagttagaag gagaatggaa ggaaggagaa    4800
gaagtccagg tattggcact ggagcctgga aaaaatccaa gagccgtcca aacgaaacct    4860
ggtcttttca aaaccaacgc cggaacaata ggtgctgtat ctctggactt ttctcctgga    4920
acgtcaggat ctccaattat cgacaaaaaa ggaaaagttg tgggtcttta tggtaatggt    4980
gttgttacaa ggagtggagc atatgtgagt gctatagccc agactgaaaa aagcattgaa    5040
gacaacccag agatcgaaga tgacattttc cgaaagagaa gactgaccat catggaccte    5100 cacccaggag cgggaaagac gaagagatac cttccggcca tagtcagaga agctataaaa    5160
cggggtttga gaacattaat cttggccccc actagagttg tggcagctga atgcaggaa    5220 gcccttagag gacttccaat aagataccag accccagcca tcagagctgw gcacaccggg    5280
cgggagattg tggacctaat gtgtcatgcc acatttacca tgaggctgct atcaccagtt    5340
agagtgccaa actacaacct gattatcatg gacgaagccc atttcacaga cccagcaagt    5400
atagcagcta gaggatacat ctcaactcga gtggagatgg tgaggcagc tgggattttt    5460 atgacagcca ctcccccggg aagcagagac ccatttcctc agagcaatgc accaatcata    5520
gatgaagaaa gagaaatccc tgaacgctcg tggaattccg acatgaatg ggtcacggat    5580 tttaaggga agactgtttg gttcgttcca agtataaaag caggaaatga tatagcagct    5640
tgcctgagga aaaatggaaa gaaagtgata caactcagta ggaagacctt tgattctgag    5700
tatgtcaaga ctagaaccaa tgattgggac ttcgtggtta caactgacat ttcagaaatg    5760
ggtgccaatt tcaaggctga gagggttata gaccccagac gctgcatgaa accagtcata    5820
```

| | |
|---|---|
| ctaacagatg gtgaagagcg ggtgattctg gcaggaccta tgccagtgac ccactctagt | 5880 |
| gcagcacaaa gaagagggag aataggaaga aatccaaaaa atgagaatga ccagtacata | 5940 |
| tacatggggg aacctctgga aaatgatgaa gactgtgcac actggaaaga agctaaaatg | 6000 |
| ctcctagata acatcaacac gccagaagga atcattccta gcatgttcga accagagcgt | 6060 |
| gaaaaggtgg atgccattga tggcgaatac cgcttgagag gagaagcaag gaaaaccttt | 6120 |
| gtagacttaa tgagaagagg agacctacca gtctggttgg cctacagagt ggcagctgaa | 6180 |
| ggcatcaact acgcagacag aaggtggtgt tttgatggag tcaagaacaa ccaaatccta | 6240 |
| gaagaaaacg tggaagttga aatctggaca aaagaagggg aaaggaagaa attgaaaccc | 6300 |
| agatggttgg atgctaggat ctattctgac ccactggcgc taaaagaatt taaggaattt | 6360 |
| gcagccggaa gaaagtctct gaccctgaac ctaatcacag aaatgggtag gctcccaacc | 6420 |
| ttcatgactc agaaggcaag agacgcactg gacaacttag cagtgctgca cacggctgag | 6480 |
| gcaggtggaa gggcgtacaa ccatgctctc agtgaactgc cggagaccct ggagacattg | 6540 |
| cttttactga cacttctggc tacagtcacg ggagggatct ttttattctt gatgagcgca | 6600 |
| aggggcatag ggaagatgac cctgggaatg tgctgcataa tcacggctag catcctccta | 6660 |
| tggtacgcac aaatacagcc acactggata gcagcttcaa taatactgga gttttttctc | 6720 |
| atagttttgc ttattccaga acctgaaaaa cagagaacac cccaagacaa ccaactgacc | 6780 |
| tacgttgtca tagccatcct cacagtggtg gccgcaacca tggcaaacga gatgggtttc | 6840 |
| ctagaaaaaa cgaagaaaga tctcggattg ggaagcattg caacccagca acccgagagc | 6900 |
| aacatcctgg acatagatct acgtcctgca tcagcatgga cgctgtatgc cgtggccaca | 6960 |
| acatttgtta caccaatgtt gagacatagc attgaaaatt cctcagtgaa tgtgtcccta | 7020 |
| acagctatag ccaaccaagc cacagtgtta atgggtctcg ggaaaggatg gccattgtca | 7080 |
| aagatggaca tcggagttcc ccttctcgcc attggatgct actcacaagt caaccccata | 7140 |
| actctcacag cagctctttt cttattggta gcacattatg ccatcatagg gccaggactc | 7200 |
| caagcaaaag caaccagaga agctcagaaa agagcagcgg cgggcatcat gaaaaaccca | 7260 |
| actgtcgatg gaataacagt gattgaccta gatccaatac cttatgatcc aaagtttgaa | 7320 |
| aagcagttgg gacaagtaat gctcctagtc ctctgcgtga ctcaagtatt gatgatgagg | 7380 |
| actacatggg ctctgtgtga ggctttaacc ttagctaccg ggcccatctc acattgtggg | 7440 |
| gaaggaaatc agggaggtt ttggaacact accattgcgg tgtcaatggc taacattttt | 7500 |
| agagggagtt acttggccgg agctggactt ctcttttcta ttatgaagaa cacaaccaac | 7560 |
| acaagaaggg gaactggcaa cataggagag acgcttggag agaaatggaa aagccgattg | 7620 |
| aacgcattgg gaaaaagtga attccagatc tacaagaaaa gtggaatcca ggaagtggat | 7680 |
| agaaccttag caaaagaagg cattaaaaga ggagaaacgg accatcacgc tgtgtcgcga | 7740 |
| ggctcagcaa aactgagatg gttcgttgag agaaacatgg tcacaccaga agggaaagta | 7800 |
| gtggacctcg gttgtggcag aggaggctgg tcatactatt gtggaggact aaagaatgta | 7860 |
| agagaagtca aaggcctaac aaaaggagga ccaggacacg aagaacccat ccccatgtca | 7920 |
| acatatgggt ggaatctagt gcgtcttcaa agtggagttg acgttttctt catcccgcca | 7980 |
| gaaaagtgtg acacattatt gtgtgacata ggggagtcat caccaaatcc cacagtggaa | 8040 |
| gcaggacgaa cactcagagt ccttaactta gtagaaaatt ggttgaacaa caacactcaa | 8100 |
| ttttgcataa aggttctcaa cccatatatg ccctcagtca tagaaaaaat ggaagcacta | 8160 |
| caaaggaaat atggaggagc cttagtgagg aatccactct cacgaaactc cacacatgag | 8220 |

```
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt tgtccccatg   8580
gtgacacaga tggcaatgac agacacgact ccatttggac aacagcgcgt ttttaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttccacca tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaaccttag atgacaggtt cgcaagcgct   9600
ttaacagctc taaatgacat gggaaagatt aggaaagaca tacaacaatg gaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagaagaa ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agcaagga  10260
gttctgtggt agaaagcaaa actaacgatga aacaaggcta gaagtcaggt cggattaagc  10320
catagtacgg aaaaaactat gctacctgtg agccccgtcc aaggacgtta aaagaagtca  10380
ggccatcata aatgccatag cttgagtaaa ctatgcagcc tgtagctcca cctgagaagg  10440
tgtaaaaaat ccgggaggcc acaaaccatg gaagctgtac gcatggcgta gtggactagc  10500
ggttagagga gacccctccc ttacaaatcg cagcaacaat gggggcccaa ggcgagatga  10560
```
agctgtagtc tcgctggaag gactagaggt tagaggagac ccccccgaaa caaaaaacag 10620
catattgacg ctgggaaaga ccagagatcc tgctgtctcc tcagcatcat tccaggcaca 10680
gaacgccaga aaatggaatg gtgctgttga atcaacaggt tct 10723

<210> SEQ ID NO 39
<211> LENGTH: 10735
<212> TYPE: DNA
<213> ORGANISM: Dengue virus
<220> FEATURE:
<221> NAME/KEY: misc_feature
<222> LOCATION: (1)..(10735)
<223> OTHER INFORMATION: VDV1

<400> SEQUENCE: 39
agttgttagt ctacgtggac cgacaagaac agtttcgaat cggaagcttg cttaacgtag 60
ttctaacagt tttttattag agagcagatc tctgatgatc aaccaacgaa aaaagacggg 120
tcgaccgtct ttcaatatgc tgaaacgcgc gagaaaccgc gtgtcaactg tttcacagtt 180
ggcgaagaga ttctcaaaag gattgctctc aggccaagga cccatgaaat tggtgatggc 240
tttcatagca ttcttaagat ttctagccat acccccaaca gcaggaattt tggctagatg 300
gggctcattc aagaagaatg gagcgattaa agtgttacgg ggtttcaaga gagaaatctc 360
aaacatgcta aacataatga acaggaggaa aagatccgtg accatgctcc ttatgctgct 420
gcccacagcc ctggcgttcc atctgacgac acgaggggga gagccgcata tgatagttag 480
caagcaggaa agaggaaagt cacttttgtt caagacctct gcaggtgtca acatgtgcac 540
cctcattgcg atggatttgg gagagttgtg tgaggacacg atgacctaca aatgcccccg 600
gatcactgag gcggaaccag atgacgttga ctgttggtgc aatgccacgg acacatgggt 660
gacctatgga acgtgctctc aaactggcga acaccgacga gacaaacgtt ccgtcgcatt 720
ggccccacac gtggggcttg gcctagaaac aagagccgaa acgtggatgt cctctgaagg 780
tgcttggaaa cagatacaaa aagtagagac ttgggctctg agacatccag gattcacggt 840
gatagccctt tttctagcac atgccatagg aacatccatc acccagaaag ggatcatttt 900
cattttgctg atgctggtaa caccatctat ggccatgcga tgcgtgggaa taggcaacag 960
agacttcgtg gaaggactgt caggagcaac atgggtggat gtggtactgg agcatggaag 1020
ttgcgtcacc accatggcaa aaaacaaacc aacactggac attgaactct tgaagacgga 1080
ggtcacaaac cctgcagttc tgcgtaaatt gtgcattgaa gctaaaatat caaacaccac 1140
caccgattcg agatgtccaa cacaaggaga agccacactg gtggaagaac aagacgcgaa 1200
ctttgtgtgc cgacgaacgt tcgtggacag aggctggggc aatggctgtg ggctattcgg 1260
aaaaggtagt ctaataacgt gtgccaagtt taagtgtgtg acaaaactag aaggaaagat 1320
agctcaatat gaaaacctaa aatattcagt gatagtcacc gtccacactg gagatcagca 1380
ccaggtggga aatgagacta cagaacatgg aacaactgca accataacac ctcaagctcc 1440
tacgtcggaa atacagctga ccgactacgg aacccttaca ttagattgtt cacctaggac 1500
agggctagat tttaacgaga tggtgttgct gacaatgaaa aagaaatcat ggcttgtcca 1560
caaacagtgg tttctagact taccactgcc ttggacctct ggggctttaa catcccaaga 1620
gacttggaac agacaagatt tactggtcac atttaagaca gctcatgcaa agaagcagga 1680
agtagtcgta ctaggatcac aagaaggagc aatgcacact gcgctgactg gagcgacaga 1740
aatccaaacg tcaggaacga caacaatttt cgcaggacac ctaaaatgca gactaaaaat 1800
ggacaaacta actttaaaag ggatgtcata tgtgatgtgc acaggctcat tcaagttaga 1860

```
gaaagaagtg gctgagaccc agcatggaac tgttctggtg caggttaaat atgaaggaac    1920
agacgcacca tgcaagattc ccttttcgac ccaagatgag aaaggagcaa cccagaatgg    1980
gagattaata acagccaacc ccatagtcac tgacaaagaa aaaccagtca atattgaggc    2040
agaaccaccc tttggtgaga gctacatcgt ggtaggagca ggtgaaaaag ctttgaaact    2100
aagctggttc aagaaaggaa gcagcatagg gaaaatgttt gaagcaactg cccgaggagc    2160
acgaaggatg gccattctgg agacaccgc atgggacttc ggttctatag gaggagtgtt     2220
cacgtctatg ggaaaactgg tacaccaggt ttttggaact gcatatggag ttttgtttag    2280
cggagtttct tggaccatga aataggaat agggattctg ctgacatggc taggattaaa     2340
ttcaaggaac acgtcccttt cggtgatgtg catcgcagtt ggcatggtca cactgtacct    2400
aggagtcatg gttcaggcag attcgggatg tgtaatcaac tggaaaggca gagaacttaa    2460
atgtggaagc ggcattttg tcactaatga agttcacact tggacagagc aatacaaatt     2520
ccaggctgac tcccccaaga gactatcagc agccattggg aaggcatggg aggagggtgt    2580
gtgtggaatc cgatcagcca ctcgtctcga gaacatcatg tggaaacaaa tatcaaatga    2640
attgaaccac atcctacttg aaaatgacat gaaatttaca gtggtcgtgg agacgttag     2700
tggaatcttg gcccaaggaa aaaaaatgat taggccacaa cccatggaac acaaatactc    2760
gtggaaaagc tggggaaaag ctaaaatcat aggagcggat gtacagaaca ccaccttcat    2820
catcgacggc ccaaacaccc cagaatgccc tgacaatcaa agagcatgga atatttggga    2880
agtagaggac tatggatttg ggatttcac gacaaacata tggttgaaat tgcgtgactc     2940
ctacacccaa gtatgtgacc accggctgat gtcagctgcc attaaggaca gcaaggcagt    3000
ccatgctgac atggggtact ggatagaaag tgaaaagaac gagacatgga gttggcgag    3060
agcctccttt atagaagtta agacatgcat ctggccaaaa tcccacactc tatggagcaa    3120
tggagttctg gaaagtgaaa tgataattcc aaagatatat ggaggaccaa tatctcagca    3180
caactacaga ccaggatatt tcacacaaac agcagggccg tggcacctag caagttgga     3240
actagatttc gatttttgtg aaggtaccac agttgttgtg gatgaacatt gtggaaatcg    3300
aggaccatct ctcagaacca caacagtcac aggaaagata atccatgaat ggtgctgcag    3360
atcttgtacg ctaccccccc tacgtttcaa aggggaagac gggtgttggt acggcatgga    3420
aatcagacca gtgaaggaca aggaagagaa cctggtcaag tcaatggtct ctgcagggtc    3480
aggagaagtg gacagctttt cactaggact gctatgcata tcaataatga ttgaagaagt    3540
gatgagatcc agatggagca aaaaaatgct gatgactgga acactggctg tgttcctcct    3600
tcttataatg ggacaattga catggagtga tctgatcagg ttatgtatta tggttggagc    3660
caacgcttca gacaagatgg ggatgggaac aacgtaccta gctttaatgg ccactttcaa    3720
aatgagacca atgttcgccg tcgggctatt atttcgcaga ctaacatcta gagaagttct    3780
tcttcttaca attggcttga gcctggtggc atccgtggag ctaccaagtt ccctagagga    3840
gctggggat ggacttgcaa taggcatcat gatgttgaaa ttattgactg atttcagtc     3900
acaccagcta tgggctactc tgctatcctt gacatttatt aaaacaactt tttcattgca    3960
ctatgcatgg aagacaatgg ctatggtact gtcaattgta tctctcttcc ctttatgcct    4020
gtccacgacc tctcaaaaaa caacatggct tccggtgctg ttgggatctc ttggatgcaa    4080
accactaccc atgtttctta aacagaaaaa caaaatctgg ggaaggaaga ttggccccct    4140
caatgaagga attatggctg ttggaatagt tagtattcta ctaagttcac ttttaaaaaa    4200
```

```
tgatgtgccg ctagccggcc cattaatagc tggaggcatg ctaatagcat gttatgtcat    4260
atccggaagc tcagctgatt tatcactgga gaaagcggct gaggtctcct gggaggaaga    4320
agcagaacac tcaggcgcct cacacaacat actagtagag gttcaagatg atggaaccat    4380
gaagataaaa gatgaagaga gagatgacac gctcaccatt ctccttaaag caactctgct    4440
ggcagtctca ggggtgtacc caatgtcaat accagcgacc ctttttgtgt ggtattttg    4500 gcagaaaaag aaacagagat caggagtgct atgggacaca cccagccccc cagaagtgga    4560
aagagcagtt cttgatgatg gcatctatag aattttgcaa agaggactgt tgggcaggtc    4620
ccaagtagga gtaggagttt tccaagaagg cgtgttccac acaatgtggc acgtcactag    4680
gggagctgtc ctcatgtatc aaggaaaaag gctggaacca agctgggcca gtgtcaaaaa    4740
agacttgatc tcatatggag gaggttggag gtttcaagga tcctggaaca cgggagaaga    4800
agtacaggtg attgctgttg aaccgggaaa aaaccccaaa aatgtacaaa caacgccggg    4860
taccttcaag accctgaag gcgaagttgg agccatagcc ttagacttta aacctggcac    4920
atctggatct cccatcgtaa acagagaggg aaaaatagta ggtctttatg gaaatggagt    4980
ggtgacaaca agcggaactt acgttagtgc catagctcaa gctaaggcat cacaagaagg    5040
gcctctacca gagattgagg acaaggtgtt taggaaaaga aacttaacaa taatggacct    5100
acatccagga tcgggaaaaa caagaagata ccttccagcc atagtccgtg aggccataaa    5160
aaggaagctg cgcacgctaa tcctagctcc cacaagagtt gtcgcttctg aaatggcaga    5220
ggcactcaag ggagtgccaa taaggtatca gacaacagca gtgaagagtg aacacacagg    5280
aaaggagata gttgacctta tgtgccacgc cactttcacc atgcgcctcc tgtctcccgt    5340
gagagttccc aattataaca tgattatcat ggatgaagca cacttcaccg atccagccag    5400
catagcagcc agagggtaca tctcaacccg agtgggtatg ggtgaagcag ctgcgatctt    5460
tatgacagcc actcccccag gatcggtgga ggcctttcca cagagcaatg caattatcca    5520
agatgaggaa agagacattc ctgagagatc atggaactca ggctatgact ggatcactga    5580
ttttccaggt aaaacagtct ggtttgttcc aagcatcaaa tcaggaaatg acattgccaa    5640
ctgtttaaga aaaacgggaa aacgggtgat ccaattgagc agaaaaacct ttgacactga    5700
gtaccagaaa acaaaaaaca acgactggga ctatgtcgtc acaacagaca tttccgaaat    5760
gggagcaaat ttccgggccg acagggtaat agacccaagg cggtgtctga accggtaat    5820 actaaaagat ggtccagagc gcgtcattct agccggaccg atgccagtga ctgtggccag    5880
tgccgcccag aggagaggaa gaattggaag gaaccaaaac aaggaaggtg atcagtatat    5940
ttacatggga cagccttta aaaatgatga ggaccacgct cattggacag aagcaaagat    6000
gctccttgac aatataaaca caccagaagg gattatccca gccctctttg agccggagag    6060
agaaaagagt gcagctatag acggggaata cagactgcgg ggtgaagcaa ggaaaacgtt    6120
cgtggagctc atgagaagag gggatctacc agtctggcta tcctacaaag ttgcctcaga    6180
aggcttccag tactccgaca gaaggtggtg cttcgatggg gaaaggaaca accaggtgtt    6240
ggaggagaac atggacgtgg agatctggac aaaagaagga gaaagaaaga aactacgacc    6300
tcgctggttg gacgccagaa catactctga cccactggct ctgcgcgagt ttaaagagtt    6360
tgcagcagga agaagaagcg tctcaggtga cctaatatta gaaataggga acttccaca    6420 acatttgacg caaagggccc agaatgcttt ggacaacttg gtcatgttgc acaattccga    6480
acaaggagga aaagcctata gacatgctat ggaagaactg ccagacacaa tagaaacgtt    6540
gatgctccta gccttgatag ctgtgttgac tggtggagtg acgctgttct tcctatcagg    6600
```

```
aagaggtcta ggaaaaacat ctatcggctt actctgcgtg atggcctcaa gcgcactgtt    6660
atggatggcc agtgtggagc cccattggat agcggcctcc atcatactgg agttctttct    6720
gatggtactg cttattccag agccagacag acagcgcact ccacaggaca accagctagc    6780
atatgtggtg ataggtctgt tattcgtgat attgacagtg gcagccaatg agatgggatt    6840
attggaaacc acaagaaag acctgggat tggccatgta gctgctgaaa accaccacca    6900
tgctacaatg ctggacgtag acctacatcc agcttcagcc tggaccctct atgcagtggc    6960
cacaacaatc atcactccta tgatgagaca cacaattgaa aacacaacgg caaatatttc    7020
cctgacagcc atcgcaaacc aagcagctat attgatggga cttgacaagg gatggccaat    7080
atcgaagatg gacataggag ttccacttct cgccttgggg tgctattccc aagtgaatcc    7140
gctgacactg atagcggcag tattgatgct agtagctcat tacgccataa ttggacctgg    7200
actgcaagca aaagctacta gagaagctca aaaaagaaca gcggctggaa taatgaaaaa    7260
tccaactgtc gacgggattg ttgcaataga cttagatccc gtggtttacg atgcaaaatt    7320
tgaaaaacag ctaggccaaa taatgttgtt gatactttgc acatcacaga ttcttttgat    7380
gcggactaca tgggccttgt gtgaatccat cacattggct actggacctc tgaccactct    7440
ttgggaggga tctccaggaa aattctggaa caccacaata gcggtatcca tggcaaacat    7500
tttcagggga agttatctag caggagcagg tctggccttc tcattaatga aatctctagg    7560
aggaggtagg agaggcacgg gagcccaagg ggaaacactg ggagaaaaat ggaaaagaca    7620
actaaaccaa ctgagcaagt cagaattcaa tacttacaag aggagtggga ttatggaggt    7680
ggatagatcc gaagccaaag agggactgaa aagaggagaa acaaccaaac acgcagtatc    7740
gagaggaacg gccaaactga ggtggttcgt ggagaggaac cttgtgaaac cagaagggaa    7800
agtcatagac ctcggttgtg gaagaggtgg ctggtcatat tattgcgctg ggctgaagaa    7860
agtcacagaa gtgaaaggat acacaaaagg aggacctgga catgaggaac caatcccaat    7920
ggcgacctat ggatggaacc tagtaaggct gcactccgga aagatgtat tttttatacc    7980 acctgagaaa tgtgacaccc ttttgtgtga tattggtgag tcctctccga acccaactat    8040
agaggaagga gaacgttac gtgttctgaa aatggtggaa ccatggctca gaggaaacca    8100 atttgcata aaaattctaa atccctatat gccgagcgtg gtagaaactc tggaacaaat    8160
gcaaagaaaa catggaggaa tgctagtgcg aaacccactc tcaagaaatt ccacccatga    8220
aatgtactgg gtttcatgtg aacaggaaa cattgtgtca gcagtaaaca tgacatctag    8280
aatgttgcta aatcggttca caatggctca caggaagcca acatatgaaa gagacgtgga    8340
cttaggcgct ggaacaagac atgtggcagt agaaccagag gtagccaacc tagatatcat    8400
tggccagagg atagagaata taaaaatga acataagtca acatggcatt atgatgagga    8460
caatccatac aaaacatggg cctatcatgg atcatatgag gttaagccat caggatcggc    8520
ctcatccatg gtcaatggcg tggtgagatt gctcaccaaa ccatgggatg ttatccccat    8580
ggtcacacaa atagccatga ctgataccac accctttgga caacagaggg tgtttaaaga    8640
gaaagttgac acgcgcacac caaaagcaaa acgtggcaca gcacaaatta tggaagtgac    8700
agccaggtgg ttatggggtt cctttctag aaacaaaaaa cccagaattt gcacaagaga    8760
ggagtttaca agaaaagtta ggtcaaacgc agctattgga gcagtgttcg ttgatgaaaa    8820
tcaatggaac tcggcaaaag aagcagtgga agacgaacgg ttctgggaac ttgtccacag    8880
agagagggag cttcataaac aggggaaatg tgccacgtgt gtctacaata tgatgggaa    8940
```

-continued

```
gagagagaaa aaattaggag agttcggaaa ggcaaaagga agtcgtgcaa tatggtacat    9000
gtggttggga gcacgcttcc tagagtttga agcccttggt ttcatgaatg aagatcactg    9060
gttcagtaga gagaattcac tcagtggagt ggaaggagaa ggactccaca aacttggata    9120
catactcaga gacatatcaa ggattccagg ggggaacatg tatgcagatg acacagccgg    9180
atgggacaca agaataacag aggatgatct ccagaatgag gctaaaatca ctgacatcat    9240
ggagcccgaa catgccctgc tggctacgtc aatctttaag ctgacctacc aaaataaggt    9300
ggtaagggtg cagagaccag caaaaaatgg aaccgtgatg gatgttatat ccagacgtga    9360
ccagagaggc agtggacagg ttggaactta tggcttaaac actttcacca acatggaggc    9420
ccaactgata agacaaatgg agtctgaggg aatcttttta cccagcgaat ggaaaccccc    9480
aaatctagcc ggaagagttc tcgactggtt ggaaaaatat ggtgtcgaaa ggctgaaaag    9540
aatggcaatc agcggagatg actgtgtggt gaaaccaatt gatgacaggt tcgcaacagc    9600
cttaacagct ttgaatgaca tgggaaaagt aagaaaagac ataccacaat gggaacettc    9660
aaaaggatgg aatgattggc aacaagtgcc tttctgttca caccacttcc accagctaat    9720
tatgaaggat gggagggaga tagtggtgcc atgccgcaac caagatgaac ttgtggggag    9780
ggccagagta tcacaaggcg ccggatggag cctgagagaa accgcatgcc taggcaagtc    9840
atatgcacaa atgtggcagc tgatgtattt ccacaggaga gacctgagac tggcggctaa    9900
cgctatttgt tcagccgttc cagttgattg ggtcccaacc agccgcacca cctggtcgat    9960
ccatgcccat caccaatgga tgacaacaga agacatgtta tcagtatgga ataggggctg   10020
gatagaggaa aacccatgga tggaggataa gactcatgtg tccagttggg aagaagttcc   10080
atacctagga aagagggaag atcagtggtg tggatccctg ataggcttaa cagcaagggc   10140
cacctgggcc actaatatac aagtggccat aaaccaagtg agaaggctca ttgggaatga   10200
gaattatcta gattacatga tcaatgaaga gattcaag aatgagagtg atcccgaagg   10260
ggcactctgg taagtcaaca cattcacaaa ataaaggaaa ataaaaaatc aaatgaggca   10320
agaagtcagg ccagattaag ccatagtacg gtaagagcta tgctgcctgt gagccccgtc   10380
caaggacgta aaatgaagtc aggccgaaag ccacggtttg agcaagccgt gctgcctgtg   10440
gctccatcgt ggggatgtaa aaacccggga ggctgcaacc catggaagct gtacgcatgg   10500
ggtagcagac tagtggttag aggagacccc tcccaagaca caacgcagca gcggggccca   10560
acaccagggg aagctgtacc ctggtggtaa ggactagagg ttagaggaga ccccccgcgt   10620
aacaataaac agcatattga cgctgggaga accagagatt cctgctgtct ctacagcatc   10680
attccaggca cagaacgcca gaaaatggaa tggtgctgtt gaatcaacag gttct         10735
```

<210> SEQ ID NO 40
<211> LENGTH: 10735
<212> TYPE: DNA
<213> ORGANISM: Dengue virus
<220> FEATURE:
<221> NAME/KEY: misc_feature
<222> LOCATION: (1)..(10735)
<223> OTHER INFORMATION: LAV1/PDK13

<400> SEQUENCE: 40

```
agttgttagt ctacgtggac cgacaagaac agtttcgaat cggaagcttg cttaacgtag      60
ttctaacagt tttttattag agagcagatc tctgatgatc aaccaacgaa aaaagacggg     120
tcgaccgtct ttcaatatgc tgaaacgcgc gagaaaccgc gtgtcaactg tttcacagtt     180
ggcgaagaga ttctcaaaag gattgctctc aggccaagga cccatgaaat tggtgatggc     240
```

```
tttcatagca ttcttaagat ttctagccat accccccaaca gcaggaattt tggctagatg      300
gggctcattc aagaagaatg gagcgattaa agtgttacgg ggtttcaaga gagaaatctc      360
aaacatgcta aacataatga acaggaggaa aagatccgtg accatgctcc ttatgctgct      420
gcccacagcc ctggcgttcc atctgacgac acgaggggga gagccgcata tgatagttag      480
caagcaggaa agaggaaagt cacttttgtt caagacctct gcaggtgtca acatgtgcac      540
cctcattgcg atggatttgg gagagttgtg tgaggacacg atgacctaca aatgcccccg      600
gatcactgag gcggaaccag atgacgttga ctgttggtgc aatgccacgg acacatgggt      660
gacctatgga acgtgctctc aaactggcga acaccgacga acaaacgtt ccgtcgcatt       720 ggccccacac gtggggcttg cctagaaac aagagccgaa acgtggatgt cctctgaagg       780
tgcttggaaa cagatacaaa aagtagagac ttgggctctg agacatccag gattcacggt      840
gatagccctt tttctagcac atgccatagg aacatccatc acccagaaag ggatcatttt      900 catttttgctg atgctggtaa caccatctat ggccatgcga tgcgtgggaa taggcaacag     960
agacttcgtg gaaggactgt caggagcaac atgggtggat gtggtactgg agcatggaag    1020
ttgcgtcacc accatggcaa aaaacaaacc aacactggac attgaactct tgaagacgga    1080
ggtcacaaac cctgcagttc tgcgtaaatt gtgcattgaa gctaaaatat caaacaccac    1140
caccgattcg agatgtccaa cacaaggaga agccacactg gtggaagaac aagacgcgaa    1200
ctttgtgtgc cgacgaacgt tcgtggacag aggctggggc aatggctgtg ggctattcgg    1260
aaaaggtagt ctaataacgt gtgccaagtt taagtgtgtg acaaaactag aaggaaagat    1320
agctcaatat gaaaacctaa aatattcagt gatagtcacc gtccacactg gagatcagca    1380
ccaggtggga aatgagacta cagaacatgg aacaactgca accataacac ctcaagctcc    1440
tacgtcggaa atacagctga ccgactacgg aaccctaca ttagattgtt cacctaggac     1500
agggctagat tttaacgaga tggtgttgct gacaatgaaa aagaaatcat ggcttgtcca    1560
caaacagtgg tttctagact taccactgcc ttggaccctct ggggctttaa catcccaaga   1620
gacttggaac agacaagatt tactggtcac atttaagaca gctcatgcaa agaagcagga    1680
agtagtcgta ctaggatcac aagaaggagc aatgcacact gcgctgactg gagcgacaga    1740
aatccaaacg tcaggaacga caacaatttt cgcaggacac ctaaaatgca gactaaaaat    1800
ggacaaacta actttaaaag ggatgtcata tgtgatgtgc acaggctcat tcaagttaga    1860
gaaagaagtg gctgagaccc agcatggaac tgttctggtg caggttaaat atgaaggaac    1920
agacgcacca tgcaagattc cttttcgac ccaagatgag aaaggagcaa cccagaatgg     1980
gagattaata acagccaacc ccatagtcac tgacaaagaa aaaccagtca atattgaggc    2040
agaaccaccc tttggtgaga gctacatcgt ggtaggagca ggtgaaaaag ctttgaaact    2100
aagctggttc aagaaaggaa gcagcatagg gaaaatgttt gaagcaactg cccgaggagc    2160
acgaaggatg gccattctgg gagacaccgc atgggactc ggttctatag gaggagtgtt     2220
cacgtctatg ggaaaactgg tacaccaggt ttttggaact gcatatggag ttttgttag     2280 cggagttttct tggaccatga aaataggaat agggattctg ctgacatggc taggattaaa   2340
ttcaaggaac acgtccttt cggtgatgtg catcgcagtt ggcatggtca cactgtacct     2400
aggagtcatg gttcaggcag attcgggatg tgtaatcaac tggaaaggca gagaacttaa    2460
atgtggaagc ggcattttg tcactaatga agttcacact tggacagagc aatacaaatt    2520
ccaggctgac tcccccaaga gactatcagc agccattggg aaggcatggg aggagggtgt   2580
```

-continued

```
gtgtggaatc cgatcagcca ctcgtctcga gaacatcatg tggaaacaaa tatcaaatga    2640
attgaaccac atcctacttg aaaatgacat gaaatttaca gtggtcgtgg gagacgttag    2700
tggaatcttg gcccaaggga aaaaaatgat taggccacaa cccatggaac acaaatactc    2760
gtggaaaagc tggggaaaag ctaaaatcat aggagcggat gtacagaaca ccaccttcat    2820
catcgacggc ccaaacaccc cagaatgccc tgacaatcaa agagcatgga atatttggga    2880
agtagaggac tatggatttg ggattttcac gacaaacata tggttgaaat tgcgtgactc    2940
ctacacccaa gtatgtgacc accggctgat gtcagctgcc attaaggaca gcaaggcagt    3000
ccatgctgac atggggtact ggatagaaag tgaaaagaac gagacatgga agttggcgag    3060
agcctccttt atagaagtta agacatgcat ctggccaaaa tcccacactc tatggagcaa    3120
tggagttctg gaaagtgaaa tgataattcc aaagatatat ggaggaccaa tatctcagca    3180
caactacaga ccaggatatt tcacacaaac agcagggccg tggcacctag gcaagttgga    3240
actagatttc gatttttgtg aaggtaccac agttgttgtg gatgaacatt gtggaaatcg    3300
aggaccatct ctcagaacca caacagtcac aggaaagata atccatgaat ggtgctgcag    3360
atcttgtacg ctaccccccc tacgtttcaa aggggaagac gggtgttggt acggcatgga    3420
aatcagacca gtgaaggaca aggaagagaa cctggtcaag tcaatggtct ctgcagggtc    3480
aggagaagtg gacagctttt cactaggact gctatgcata tcaataatga ttgaagaagt    3540
gatgagatcc agatggagca aaaaaatgct gatgactgga cactggctg tgttcctcct    3600 tcttataatg ggacaattga catggagtga tctgatcagg ttatgtatta tggttggagc    3660
caacgcttca gacaagatgg ggatgggaac aacgtaccta gctttaatgg ccactttcaa    3720
aatgagacca atgttcgccg tcgggctatt atttcgcaga ctaacatcta gagaagttct    3780
tcttcttaca attggcttga gcctggtggc atccgtggag ctaccaagtt ccctagagga    3840
gctgggggat ggacttgcaa taggcatcat gatgttgaaa ttattgactg attttcagtc    3900
acaccagcta tgggctactc tgctatcctt gacatttatt aaaacaactt tttcattgca    3960
ctatgcatgg aagacaatgg ctatggtact gtcaattgta tctctcttcc ctttatgcct    4020
gtccacgacc tctcaaaaaa caacatggct tccggtgctg ttgggatctc ttggatgcaa    4080
accactaccc atgtttctta acagaaaaa caaaatctgg ggaaggaaga gttggcccct    4140
caatgaagga attatggctg ttggaatagt tagtattcta ctaagttcac ttttaaaaaa    4200
tgatgtgccg ctagccggcc cattaatagc tggaggcatg ctaatagcat gttatgtcat    4260
atccggaagc tcagctgatt tatcactgga gaaagcggct gaggtctcct gggaggaaga    4320
agcagaacac tcaggcgcct cacacaacat actagtagag gttcaagatg atggaaccat    4380
gaagataaaa gatgaagaga gagatgacac gctcaccatt ctccttaaag caactctgct    4440
ggcagtctca ggggtgtacc caatgtcaat accagcgacc ctttttgtgt ggtattttg    4500 gcagaaaaag aaacagagat caggagtgct atgggacaca cccagccccc cagaagtgga    4560
aagagcagtt cttgatgatg gcatctatag aattttgcaa agaggactgt gggcaggtc    4620 ccaagtagga gtaggagttt ccaagaagg cgtgttccac acaatgtggc acgtcactag    4680
gggagctgtc ctcatgtatc aaggaaaag gctggaacca agctgggca gtgtcaaaaa    4740 agacttgatc tcatatggag gaggttggag gtttcaagga tcctggaaca cgggagaaga    4800
agtacaggtg attgctgttg aaccgggaaa aaaccccaaa aatgtacaaa caacgccggg    4860
taccttcaag acccctgaag gcgaagttgg agccatagcc ttagactta aacctggcac    4920 atctggatct cccatcgtaa acagagaggg aaaaatagta ggtctttatg gaaatggagt    4980
```

```
ggtgacaaca agcggaactt acgttagtgc catagctcaa gctaaggcat cacaagaagg    5040
gcctctacca gagattgagg acaaggtgtt taggaaaaga aacttaacaa taatggacct    5100
acatccagga tcgggaaaaa caagaagata ccttccagcc atagtccgtg aggccataaa    5160
aaggaagctg cgcacgctaa tcctagctcc cacaagagtt gtcgcttctg aaatggcaga    5220
ggcactcaag ggagtgccaa taaggtatca gacaacagca gtgaagagtg aacacacagg    5280
aaaggagata gttgacctta tgtgccacgc cactttcacc atgcgcctcc tgtctcccgt    5340
gagagttccc aattataaca tgattatcat ggatgaagca cacttcaccg atccagccag    5400
catagcagcc agagggtaca tctcaacccg agtgggtatg ggtgaagcag ctgcgatctt    5460
tatgacagcc actcccccag gatcggtgga ggcctttcca cagagcaatg caattatcca    5520
agatgaggaa agagacattc ctgagagatc atggaactca ggctatgact ggatcactga    5580
ttttccaggt aaaacagtct ggtttgttcc aagcatcaaa tcaggaaatg acattgccaa    5640
ctgtttaaga aaaacgggaa acggtgat  ccaattgagc agaaaaacct ttgacactga    5700
gtaccagaaa acaaaaaaca acgactggga ctatgtcgtc acaacagaca tttccgaaat    5760
gggagcaaat ttccgggccg acagggtaat agacccaagg cggtgtctga accggtaat    5820
actaaaagat ggtccagagc gcgtcattct agccggaccg atgccagtga ctgtggccag    5880
tgccgcccag aggagaggaa gaattggaag gaaccaaaac aaggaaggtg atcagtatat    5940
ttacatggga cagcctttaa acaatgatga ggaccacgct cattggacag aagcaaagat    6000
gctccttgac aatataaaca caccagaagg gattatccca gccctctttg agccggagag    6060
agaaaagagt gcagctatag acggggaata cagactgcgg ggtgaagcaa ggaaaacgtt    6120
cgtggagctc atgagaagag gggatctacc agtctggcta tcctacaaag ttgcctcaga    6180
aggcttccag tactccgaca aaggtggtg cttcgatggg gaaaggaaca accaggtgtt    6240
ggaggagaac atggacgtgg agatctggac aaaagaagga gaaagaaaga aactacgacc    6300
tcgctggttg gacgccagaa catactctga cccactggct ctgcgcgagt ttaaagagtt    6360
tgcagcagga agaagaagcg tctcaggtga cctaatatta gaaataggga aacttccaca    6420
acatttgacg caaagggccc agaatgcttt ggacaacttg gtcatgttgc acaattccga    6480
acaaggagga aaagcctata gacatgctat ggaagaactg ccagacacaa tagaaacgtt    6540
gatgctccta gccttgatag ctgtgttgac tggtggagtg acgctgttct tcctatcagg    6600
aagaggtcta ggaaaaacat ctatcggctt actctgcgtg atggcctcaa gcgcactgtt    6660
atggatggcc agtgtggagc cccattggat agcggcctcc atcatactgg agttctttct    6720
gatggtactg cttattccag agccagacag acagcgcact ccacaggaca accagctagc    6780
atatgtggtg ataggtctgt tattcgtgat attgacagtg gcagccaatg agatgggatt    6840
attggaaacc acaaagaaag acctggggat tggccatgta gctgctgaaa accaccacca    6900
tgctacaatg ctggacgtag acctacatcc agcttcagcc tggaccctct atgcagtggc    6960
cacaacaatc atcactccta tgatgagaca cacaattgaa aacacaacgg caaatatttc    7020
cctgacagcc atcgcaaacc aagcagctat attgatggga cttgacaagg atggccaat    7080
atcgaagatg gacataggag ttccacttct cgccttgggg tgctattccc aagtgaatcc    7140
gctgacactg atagcggcag tattgatgct agtagctcat tacgccataa ttggacctgg    7200
actgcaagca aaagctacta gagaagctca aaaaagaaca gcggctggaa taatgaaaaa    7260
tccaactgtc gacgggattg ttgcaataga cttagatccc gtggtttacg atgcaaaatt    7320
```

```
tgaaaaacag ctaggccaaa taatgttgtt gatactttgc acatcacaga ttcttttgat      7380
gcggactaca tgggccttgt gtgaatccat cacattggct actggacctc tgaccactct      7440
ttgggaggga tctccaggaa aattctggaa caccacaata gcggtatcca tggcaaacat      7500
tttcaggggg agttatctag caggagcagg tctggccttc tcattaatga aatctctagg      7560
aggaggtagg agaggcacgg gagcccaagg ggaaacactg ggagaaaaat ggaaaagaca      7620
actaaaccaa ctgagcaagt cagaattcaa tacttacaag aggagtggga ttatggaggt      7680
ggatagatcc gaagccaaag agggactgaa aagaggagaa acaaccaaac acgcagtatc      7740
gagaggaacg gccaaactga ggtggttcgt ggagaggaac cttgtgaaac cagaagggaa      7800
agtcatagac ctcggttgtg aagaggtgg ctggtcatat tattgcgctg ggctgaagaa       7860
agtcacagaa gtgaaaggat acacaaaagg aggacctgga catgaggaac caatcccaat      7920
ggcgacctat ggatggaacc tagtaaagct gcactccgga aaagatgtat tttttatacc      7980
acctgagaaa tgtgacaccc ttttgtgtga tattggtgag tcctctccga acccaactat      8040
agaggaagga agaacgttac gtgttctgaa atggtggaa ccatggctca gaggaaacca       8100
attttgcata aaaattctaa atccctatat gccgagcgtg gtagaaactc tggaacaaat      8160
gcaaagaaaa catggaggaa tgctagtgcg aaacccactc tcaagaaatt ccacccatga      8220
aatgtactgg gtttcatgtg aacaggaaa cattgtgtca gcagtaaaca tgacatctag       8280
aatgttgcta aatcggttca caatggctca caggaagcca acatatgaaa gagacgtgga      8340
cttaggcgct ggaacaagac atgtggcagt agaaccagag gtagccaacc tagatatcat      8400
tggccagagg atagagaata taaaaaatga acataagtca acatggcatt atgatgagga      8460
caatccatac aaaacatggg cctatcatgg atcatatgag gttaagccat caggatcggc      8520
ctcatccatg gtcaatggcg tggtgagatt gctcaccaaa ccatgggatg ttatccccat      8580
ggtcacacaa atagccatga ctgataccac acccttggga caacagaggg tgtttaaaga      8640
gaaagttgac acgcgcacac caaaagcaaa acgtggcaca gcacaaatta tggaagtgac      8700
agccaggtgg ttatggggtt tcctttctag aaacaaaaaa cccagaattt gcacaagaga      8760
ggagtttaca agaaaagtta ggtcaaacgc agctattgga gcagtgttcg ttgatgaaaa      8820
tcaatggaac tcggcaaaag aagcagtgga agacgaacgg ttctgggaac ttgtccacag      8880
agagagggag cttcataaac agggaaatg tgccacgtgt gtctacaata tgatggggaa      8940
gagagagaaa aaattaggag agttcggaaa ggcaaaagga agtcgtgcaa tatggtacat      9000
gtggttggga gcacgcttcc tagagtttga agcccttggt ttcatgaatg aagatcactg      9060
gttcagtaga gagaattcac tcagtggagt ggaaggagaa ggactccaca acttggata     9120 catactcaga gacatatcaa ggattccagg ggggaacatg tatgcagatg acacagccgg      9180
atgggacaca agaataacag aggatgatct ccagaatgag gctaaaatca ctgacatcat      9240
ggagcccgaa catgccctgc tggctacgtc aatctttaag ctgacctacc aaaataaggt      9300
ggtaagggtg cagagaccag caaaaaatgg aaccgtgatg gatgttatat ccagacgtga      9360
ccagagaggc agtggacagg ttggaactta tggcttaaac actttcacca acatggaggc      9420
ccaactgata agacaaatgg agtctgaggg aatcttttta cccagcgaat ggaaaccc       9480 aaatctagcc ggaagagttc tcgactggtt ggaaaaatat ggtgtcgaaa ggctgaaaag      9540
aatggcaatc agcggagatg actgtgtggt gaaaccaatt gatgacaggt tcgcaacagc      9600
cttaacagct ttgaatgaca tgggaaaagt aagaaaagac ataccacaat gggaaccttc      9660
aaaaggatgg aatgattggc aacaagtgcc tttctgttca caccacttcc accagctaat      9720
```

```
tatgaaggat gggagggaga tagtggtgcc atgccgcaac caagatgaac ttgtggggag    9780
ggccagagta tcacaaggcg ccggatggag cctgagagaa accgcatgcc taggcaagtc    9840
atatgcacaa atgtggcagc tgatgtattt ccacaggaga gacctgagac tggcggctaa    9900
cgctatttgt tcagccgttc cagttgattg ggtcccaacc agccgcacca cctggtcgat    9960
ccatgcccat caccaatgga tgacaacaga agacatgtta tcagtatgga atagggtctg   10020
gatagaggaa aacccatgga tggaggataa gactcatgtg tccagttggg aagaagttcc   10080
atacctagga aagagggaag atcagtggtg tggatccctg ataggcttaa cagcaagggc   10140
cacctgggcc actaatatac aagtggccat aaaccaagtg agaaggctca ttgggaatga   10200
gaattatcta gattacatga catcaatgaa gagattcaag aatgagagtg atcccgaagg   10260
ggcactctgg taagtcaaca cattcacaaa ataaaggaaa ataaaaaatc aaatgaggca   10320
agaagtcagg ccagattaag ccatagtacg gtaagagcta tgctgcctgt gagccccgtc   10380
caaggacgta aaatgaagtc aggccgaaag ccacggtttg agcaagccgt gctgcctgtg   10440
gctccatcgt ggggatgtaa aaacccggga ggctgcaacc catggaagct gtacgcatgg   10500
ggtagcagac tagtggttag aggagacccc tcccaagaca caacgcagca gcggggccca   10560
acaccagggg aagctgtacc ctggtggtaa ggactagagg ttagaggaga ccccccgcgt   10620
aacaataaac agcatattga cgctgggaga gaccagagat cctgctgtct ctacagcatc   10680
attccaggca cagaacgcca gaaaatggaa tggtgctgtt gaatcaacag gttct         10735
```

```
<210> SEQ ID NO 41
<211> LENGTH: 10699
<212> TYPE: DNA
<213> ORGANISM: Dengue virus
<220> FEATURE:
<221> NAME/KEY: misc_feature
<222> LOCATION: (1)..(10699)
<223> OTHER INFORMATION: LAV3

<400> SEQUENCE: 41
```

```
agttgttagt ctacgtggac cgacaagaac agtttcgact cggaagcttg cttaacgtag     60
tgctgacagt tttttattag agagcagatc tctgatgaac aaccaacgga aaaagacggg    120
aaaaccgtct atcaatatgc tgaaacgcgt gagaaaccgt gtgtcaactg gatcacagtt    180
ggcgaagaga ttctcaagag gattgctgaa cggccaagga ccaatgaaat tggttatggc    240
atttatagct ttcctcagat ttctagccat tccaccgaca gcaggagtct tggctagatg    300
gggtaccttt aagaagtcgg gggctattaa ggtcttaaaa ggcttcaaga aggagatctc    360
aaacatgctg agcattatca acaaacggaa aaagacatcg ctctgtctca tgatgatgtt    420
accagcaaca cttgctttcc acttaacttc acgagatgga gagccgcgca tgattgtggg    480
gaagaatgaa agaggaaaat ccctactttt caagacagcc tctggaatca acatgtgcac    540
actcatagct atggatctgg agagatgtgt gatgacacg tcacttaca aatgccccca    600 cattaccgaa gtggagcctg aagacattga ctgctggtgc aaccttacat cgacatgggt    660
gacttatgga acatgcaatc aagctggaga gcatagacgc gataagagat cagtggcgtt    720
agctccccat gttggcatgg gactggacac acgcactcaa acctggatgt cggctgaagg    780
agcttggaga caagtcgaga aggtagagac atgggcctt aggcacccag ggtttaccat    840
actagcccta tttcttgccc attacatagg cacttccttg acccagaaag tggttatttt    900
tatactatta atgctggtta ccccatccat gacaatgaga tgtgtaggag taggaaacag    960
```

```
agattttgtg gaaggcctat cgggagctac gtgggttgac gtggtgctcg agcacggtgg    1020
gtgtgtgact accatggcta agaacaagcc cacgctggac atagagcttc agaagaccga    1080
ggccacccaa ctggcgaccc taaggaagct atgcattgag ggaaaaatta ccaacataac    1140
aaccgactca agatgtccca cccaagggga agcgatttta cctgaggagc aggaccagaa    1200
ctacgtgtgt aagcatacat acgtggacag aggctggga aacggttgtg gtttgtttgg    1260
caagggaagc ttggtgacat gcgcgaaatt tcaatgttta gaatcaatag agggaaaagt    1320
ggtgcaacat gagaacctca aatacaccgt catcatcaca gtgcacacag agaccaaca    1380 ccaggtggga aatgaaacgc agggagtcac ggctgagata acaccccagg catcaaccgc    1440
tgaagccatt ttacctgaat atggaaccct cgggctagaa tgctcaccac ggacaggttt    1500
ggatttcaat gaaatgatct yattgacaat gaagaacaaa gcatggatgg tacatagaca    1560
atggttcttt gacttacccc taccatggac atcaggagct acagcagaaa caccaacttg    1620
gaacaggaaa gagcttcttg tgacatttaa aaatgcacat gcaaaaaagc aagaagtagt    1680
tgttcttgga tcacaagagg gagcaatgca tacagcactg acaggagcta cagagatcca    1740
aacctcagga ggcacaagta tctttgcggg gcacttaaaa tgtagactca agatggacaa    1800
attggaactc aaagggatga gctatgcaat gtgcttgggt agctttgtgt tgaagaaaga    1860
agtctccgaa acgcagcatg ggacaatact cattaaggtt gagtacaaag ggaagatgc    1920 accctgcaag attcctttct ccacggagga tggacaagga aaagctcaca atggcagact    1980
gatcacagcc aatccagtgg tgaccaagaa ggaggagcct gtcaacattg aggctgaacc    2040
tccttttgga gaaagtaaca tagtaattgg aattggagac aaagccctga aaatcaactg    2100
gtacaagaag ggaagctcga ttgggaagat gttcgaggct actgccagag gtgcaaggcg    2160
catggccatc ttgggagaca cagcctggga cttggatca gtgggtggtg ttttgaattc    2220
attagggaaa atggtccacc aaatatttgg gagtgcttac acagccctat ttggtggagt    2280
ctcctggatg atgaaaattg gaataggtgt cctcttaacc tggataggt tgaactcaaa    2340 aaatacttct atgtcatttt catgcatcgc gataggaatc attacactct atctgggagc    2400
cgtggtgcaa gctgacatgg ggtgtgtcat aaactgaaa ggcaaagaac tcaaatgtgg    2460
aagtggaatt ttcgtcacta atgaggtcca cacctggaca gagcaataca aatttcaagc    2520
agactccccc aagagactgg caacagccat tgcaggcgct tgggaaaatg gagtgtgcgg    2580
aattaggtca caaccagaa tggagaacct cttgtggaag caaatagcca atgaactgaa    2640
ttacatatta tgggaaaaca acattaaatt aacggtagtt gtaggcgaca taactggggt    2700
cttagagcaa gggaaaagaa cactaacacc acaacccatg gagctaaaat attcttggaa    2760
aacatgggga aaggcaaaaa tagtgacagc tgaaacacaa aattcctctt tcataataga    2820
tgggccaagc acaccggagt gtccaagtgc ctcaagagca tggaatgtgt gggaggtgga    2880
ggattacggg ttcggagttt tcacaaccaa catatggctg aaactccgag aggtgtacac    2940
ccaactatgt gaccataggc taatgtcggc agccgtcaag gatgagaggg ctgtacatgc    3000
cgacatgggc tattggatag aaagccaaaa gaatgggagt tggaagctag aaaaagcatc    3060
cttcatagag gtgaaaacct gcacatggcc aaaatcacac actctctgga gcaatggtgt    3120
gctagagagt gacatgatta tcccaaagag tctagctggt cccatttcgc aacacaacca    3180
caggcccggg taccacaccc aaacggcagg accctggcac ttaggaaaat tggagctgga    3240
cttcaactat tgtgaaggaa caacagttgt catctcagaa aactgtggga caagaggccc    3300
atcattgaga acaacaacgg tgtcagggaa gttgatacac gaatggtgct gccgctcgtg    3360
```

```
cacacttcct cccctacgat acatgggaga agacggctgc tggtatggca tggaaatcag   3420
acccattaat gagaaagaag agaatatggt aaagtctcta gcctcagcag ggagtggaaa   3480
ggtggacaac ttcacaatgg gtgtcttgtg tttggcaatc ctctttgaag aggtgatgag   3540
aggaaaattt gggaaaaaac acatgattgc agggggttctc ttcacgtttg tgctcctcct   3600
ctcagggcaa ataacatgga gagacatggc gcacacactc ataatgattg ggtccaacgc   3660
ctctgacaga atggggatgg gcgtcactta cctagctcta attgcaacat ttaaaattca   3720
gccactcctg gctttgggat tcttcctgag gaaactgaca tctagagaaa atttattgct   3780
gggagttggg ttggccatgg cagcaacgtt acgactgcca gaggacattg aacagatggc   3840
gaatggaatt gctttggggc tcatggctct taaactgata acacaatttg aaacatacca   3900
actatggacg gcattagttt ccctaacgtg ttcaaataca attttcacgt tgactgttgc   3960
ctggagaaca gccactctga ttttagccgg aatttcgctt ttgccagtgt gccagtcttc   4020
gagcatgagg aaaacagatt ggctcccaat gactgtggca gctatgggag ctcaacccct   4080 accactttt attttcagtc tgaaagatac actcaaaagg agaagctggc cactgaatga   4140
gggggtgatg gcagttggac ttgtgagcat tctagctagt tctctcctta ggaatgatgt   4200
gcctatggct ggaccattag tggctggggg cttgctgata gcgtgctacg tcataactgg   4260
cacgtcagca gacctcactg tagaaaaagc agcagatgta acatgggagg aagaggccga   4320
gcaaacagga gtgtcccaca atttaatggt cacagttgat gatgatggaa caatgagaat   4380
aaaagatgac gagactgaga acatcttaac agtgctttta aaaacagcac tactaatagt   4440
atcaggcatc tttccatact ccatacccgc aacactgttg gtctggcata cttggcaaaa   4500
gcaaacccaa agatccggcg tcctatggga cgtacccagc cccccagaga cacagaaagc   4560
ggaactggaa gaagggtgct ataggatcaa acagcaagga atttttggga aacccaagt   4620 gggggttgga gtacagaaag aaggagtttt ccacaccatg tggcatgtca caagaggggc   4680
agtgttgaca cacaatggga aaagactgga accaaactgg gctagcgtga aaaagatct   4740 gatttcatac ggaggaggat ggagattgag tgcacaatgg aaaaggggg aggaggtgca   4800 ggttattgcc gtagagcctg ggaagaaccc aaagaacttt caaccatgc caggcatttt   4860 tcagacaaca acaggggaaa taggagcaat tgcactggat ttcaagcctg gaacttcagg   4920
atctcccatc ataaacagag agggaaagt agtgggactg tatggcaatg gagtggttac   4980
aaagaatgga ggctatgtca gtggaatagc gcaaacaaat gcagaaccag atggaccgac   5040
accagagttg gaagaagaga tgttcaaaaa gcgaaatcta accataatgg atctccatcc   5100
tgggtcagga aagacgcgga aatatcttcc agctattgtt agagaggcaa tcaagagacg   5160
cttaaggact ctaattttgg caccaacaag ggtagttgca gctgagatgg aagaagcatt   5220
gaaagggctc ccaataaggt atcaaacaac tgcaacaaaa tctgaacaca caggaagaga   5280
gattgttgat ctaatgtgtc acgcaacgtt cacaatgcgc ttgctgtcac cagtcagggt   5340
tccaaactac aacttgataa taatggatga ggcccatttc acagacccag ccagtatagc   5400
ggctagaggg tacatatcaa ctcgtgtagg aatgggagag gcagccgcaa ttttcatgac   5460
agcaacaccc cctggaacag ctgatgcctt tcctcagagc aacgctccaa ttcaagatga   5520
agagagagac ataccggaac gctcatggaa ttcaggcaat gaatggatta ctgactttgt   5580
tgggaagaca gtgtggtttg tccctagcat caaagccgga aatgacatag caaactgctt   5640
gcggaaaaat ggaaaaaagg ttattcaact cagcaggaag acctttgaca cagaatatca   5700
```

```
aaagaccaaa ctgaatgatt gggactttgt ggtgacaaca gacatttcag aaatgggagc    5760
caatttcaaa gcagatagag tgatcgaccc aagaagatgt ctcaagccgg tgattttgac    5820
agatggaccc gagcgggtga tcctggctgg accaatgcca gtcaccgtag cgagcgctgc    5880
gcaaaggaga gggagagttg gcaggaaccc acaaaaagaa aatgaccagt acatattcat    5940
gggccagcct ctcaacaatg atgaagacca tgctcactgg acagaagcaa aaatgctgct    6000
ggacaacatc aacacaccag aagggattat accagctctc tttgaaccag aaagggagaa    6060
gtcagccgcc atagacggcg aataccgcct gaagggtgag tccaggaaga ctttcgtgga    6120
actcatgagg aggggtgacc tcccagtttg gctagcccat aaagtagcat cagaagggat    6180
caaatataca gatagaaaat ggtgctttga tggaacgt aataatcaaa ttttagagga    6240
gaatatggat gtggaaatct ggacaaagga aggagaaaag aaaaaactga gacctaggtg    6300
gcttgatgcc cgcacttatt cagatccttt agcactcaaa gaattcaagg attttgcagc    6360
tggcagaaag tcaatcgccc ttgatcttgt gacagaaata ggaagagtgc cttcacactt    6420
agcccacaga acgagaaacg ccctggataa tttggtgatg ctgcacacgt cagaacatgg    6480 cggtaggggcc tacaggcatg cagtggagga actaccagaa cgatggaaaa cactcttact    6540
cctgggactg atgatcttgt taacaggtgg agcaatgctc ttcttgatat caggtaaagg    6600
gattggaaag acttcaatag gactcatttg tgtaattgct ccagcggca tgttatggat    6660 ggctgatgtc ccactccaat ggatcgcatc ggctatagtc ctggagtttt ttatgatggt    6720
gttgctcata ccagaaccag aaaagcagag aactccccaa gacaaccaac tcgcatatgt    6780 cgtgatagge atacttacat tggctgcaat agtagcggcc aatgaaatgg gactgttgga    6840
aactacaaag agagatttag gaatgtctaa agaaccaggt gttgtttctc caaccagcta    6900
tttggatgtg gacttgcacc cagcatcagc ctggacattg tacgccgtgg ccacaacagt    6960
aataacacca atgttgagac acaccataga gaattccaca gcaaatgtgt ctctggcagc    7020
catagctaac caggcagtgg tcctgatggg tttagacaaa ggatggccga tatcgaaaat    7080
ggacttgggc gtaccactat tggcactggg ttgctattca caagtgaacc cactaactct    7140
tgcagcggca gtacttttgc tagtcacaca ttatgcaatt ataggtccag gattgcaggc    7200
aaaagccacc cgtgaagctc agaaaaggac agctgctgga ataatgaaga atccaacggt    7260
ggatggaata atgacaatag acctagatcc tgtaatatat gattcaaaat ttgaaaagca    7320
actaggacag gtcatgctcc tggttctgtg tgcagtccaa cttttattga tgagaacatc    7380
atgggccttg tgtgaagttc taaccctagc cacaggacca ataacaacac tctgggaagg    7440
atcacctggg aagttctgga acaccacgat agctgtttcc atggcgaaca tctttagagg    7500 gagctatta gcaggagctg gcttgctttt ttctatcatg aaatcagttg aacaggaaa    7560 gagaggaaca gggtcacaag gtgaaacctt aggagaaaag tggaaaaaga aattaaatca    7620
gttatcccgg aaagagtttg acctttacaa gaaatccgga atcaccgaag tggatagaac    7680
agaagccaaa gaagggttaa aaagaggaga ataacacac catgccgtgt ccagaggcag    7740
cgcaaaactt caatggttcg tggagagaaa catggtcatt cctgaaggaa gagtcataga    7800
cctaggctgt ggaagaggag ctggtcata ttactgtgca ggactgaaaa aagttacaga    7860
agtgcgagga tacacaaaag gcggcccagg acacgaagaa ccagtaccta tgtctacata    7920
cggatggaac atagtcaagt taatgagtgg aaaggatgtt ttttatctgc cacctgaaaa    7980
gtgtgatacc ctattgtgtg acattggaga atcttcacca gcccaacag tggaagaaag    8040 cagaaccata agagttttga gatggttga accatggcta aagaacaacc agttttgcat    8100
```

```
taaagtattg aacccataca tgccaactgt gattgagcac ttagaaagac tacaaaggaa    8160
acatggagga atgcttgtga gaaatccact ctcacgaaac tccacgcacg aaatgtattg    8220
gatatccaat ggtacaggca atatcgtctc ttcagtcaac atggtatcca gattgctact    8280
gaacagattc acaatgacac acaggagacc caccatagaa aaagatgtgg atctaggagc    8340
aggaacccga catgtcaatg cggaaccaga acacccaac atggatgtca ttggggaaag     8400
aataaaaagg atcaaagagg agcatagttc aacatggcac tatgatgatg aaaatcctta    8460
caaaacgtgg gcttaccatg gatcctatga agtaaaagcc acaggctcag cctcctccat    8520
gataaatgga gtcgtgaaac tcctcacaaa accatgggat gtggtgccca tggtgacaca    8580
gatggcaatg acagatacaa ctccattcgg ccagcaaaga gttttttaaag agaaagtgga   8640
caccaggaca cctaggccca tgccaggaac aagaaaggtt atggagatca cagcggagtg    8700
gctttggagg accctgggaa ggaacaaaag acccagatta tgcacaaggg aggaattcac    8760
aaagaaggtc agaaccaacg cagctatggg cgctgtcttc acagaagaga accaatggga    8820
cagtgcgaga gctgctgttg aggacgaaga attttggaaa cttgtggaca gagaacgtga    8880
actccacaaa ctgggcaagt gtggaagctg cgtttacaac atgatgggca agagagagaa    8940
aaaacttgga gagtttggta aagcaaaagg cagtagggct atatggtaca tgtggttggg    9000
agccaggtac cttgagttcg aggcgctcgg attcctcaat gaagaccact ggttctcgcg    9060
tgaaaactct tacagtggag tagaaggaga aggactgcac aagctgggat acatcttgag    9120
agatatttcc aagatacccg gaggagccat gtatgctgat gacacagccg gttgggacac    9180
aagaataaca gaagatgacc tgcacaatga ggaaaaaatc acacagcaga tggaccctga    9240
acacaggcag ctagcgaacg ctatattcaa gctcacatac caaaacaaag tggtcaaagt    9300
ccaacgacca actccaaagg gcacggtaat ggacatcata tctaggaaag accaaagagg    9360
cagtggacag gtgggaactt atggtctgaa cacattcacc aacatggaag cccagctaat    9420
cagacaaatg gaaggagaag gcgtgttgtc aaaggcagac ctcgagaacc cccatccgct    9480
agagaagaaa attacacaat ggttggaaac taaggagtg gaaaggttaa aaagaatggc    9540
catcagcggg gatgattgcg ttgtgaaacc aatcgacgac agattcgcca atgccctgct    9600
tgccctgaac gatatgggaa aggttagaaa ggacatacct caatggcagc catcaaaggg    9660
atggcatgat tggcaacagg tccccttctg ctcccaccac tttcatgaat tgatcatgaa    9720
agatggaaga aagttggtag ttccctgcag accccaggac gaactaatag gaagagcgag    9780
aatctcccaa ggagcaggat ggagccttag agaaactgca tgtctaggga aagcctacgc    9840
tcaaatgtgg gctctcatgt atttcacag aagagatctt agactagcat ccaacgccat    9900
atgttcagca gtaccagtcc actggtccc cacgagcaga acgacatggt ctattcatgc    9960
tcaccatcag tggatgacta cagaagacat gcttactgtc tggaacaggg tgtggataga   10020
ggacaatcca tggatggaag acaaaactcc agtcacaacg tgggaagatg ttccatatct   10080
agggaagaga gaagaccaat ggtgcggatc actcatagg ctcacttcca gagcaacctg    10140
ggcccagaac atactcacag caatccaaca ggtgagaagc ctcataggca atgaagagtt   10200
tctggactac atgccttcga tgaagagatt caggaaggag gaggagtcag agggagccat   10260
ttggtaaaag caggaggtaa actgtcaggc cacattaagc cacagtacgg aagaagctgt   10320
gcagcctgtg agccccgtcc aaggacgtta aagaagaag tcaggcccaa aagccacggt    10380
ttgagcaaac cgtgctgcct gtagctccgt cgtggggacg taaagcctgg gaggctgcaa   10440
```

```
accgtggaag ctgtacgcac ggtgtagcag actagtggtt agaggagacc cctcccatga    10500
cacaacgcag cagcggggcc cgagcactga gggaagctgt acctccttgc aaaggactag    10560
aggttagagg agaccccccg caaacaaaaa cagcatattg acgctgggag agaccagaga    10620
tcctgctgtc tcctcagcat cattccaggc acagaacgcc agaaaatgga atggtgctgt    10680
tgaatcaaca ggttctagt                                                10699
```

<210> SEQ ID NO 42
<211> LENGTH: 10648
<212> TYPE: DNA
<213> ORGANISM: Dengue virus
<220> FEATURE:
<221> NAME/KEY: misc_feature
<222> LOCATION: (1)..(10648)
<223> OTHER INFORMATION: LAV4

<400> SEQUENCE: 42
agttgttagt ctgtgtggac cgacaaggac agttccaaat cggaagcttg cttaacacag 60
ttctaacagt ttgtttgaat agagagcaga tctctggaaa aatgaaccaa cgaaaaaagg 120
tggttagacc acctttcaat atgctgaaac gcgagagaaa ccgcgtatca acccctcaag 180
ggttggtgaa gagattctca accggacttt tttctgggaa aggaccctta cggatggtgc 240
tagcattcat cacgtttttg cgagtccttt ccatcccacc aacagcaggg attctgaaaa 300
gatggggaca gttgaagaaa aataaggcca tcaggatact gattggattc aggaaggaga 360
taggccgcat gctgaacatc ttgaacggga gaaaaaggtc aacgataaca ttgctgtgct 420
tgattcccac cgtaatggcg tttcacttgt caacaagaga tggcgaaccc ctcatgatag 480
tggcaaaaca tgaaaggggg agacctctct tgtttaagac aacagagggg atcaacaaat 540
gcactctcat tgccatggac ttgggtgaaa tgtgtgagga cactgtcacg tataaatgcc 600
ccttactggt caataccgaa cctgaagaca ttgattgctg gtgcaatctc acgtctacct 660
gggtcatgta tgggacatgc acccagagcg gagaacggag acgagagaag cgctcagtag 720
ctttaacacc acattcagga atgggattgg aaacaagagc tgagacatgg atgtcatcgg 780
aaggggcttg gaagcatgct cagagagtag agagctggat actcagaaac ccaggattcg 840
cgctcttggc aggatttatg gcttatatga ttgggcaaac aggaatccag cgaactgtct 900
tctttgtcct aatgatgctg gtcgccccat cctacggaat gcgatgcgta ggagtaggaa 960
acagagactt tgtggaagga gtctcaggtg gagcatgggt cgatctggtg ctagaacatg 1020
gaggatgcgt cacaaccatg gcccagggaa aaccaacctt ggattttgaa ctgactaaga 1080
caacagccaa ggaagtggct ctgttaagaa cctattgcat tgaagcctca atatcaaaca 1140
taaccacggc aacaagatgt ccaacgcaag gagagcctta tctaaaagag gaacaagacc 1200
aacagtacat ctgccggaga gatgtggtag acagagggtg gggcaatggc tgtggcttgt 1260
ttggaaaagg aggagttgtg acatgtgcga agttttcatg ttcggggaag ataacaggca 1320
atttggtcca aattgagaac cttgaataca cagtggttgt aacagtccac aatggagaca 1380
cccatgcagt aggaaatgac acatccaatc atggagttac agccacgata actcccaggt 1440
caccatcggt ggaagtcaaa ttgccggact atggagaact aacactcgat tgtgaaccca 1500
ggtctggaat tgactttaat gagatgattc tgatgaaaat gaaaaagaaa acatggcttg 1560
tgcataagca atggtttttg gatctacctc taccatggac agcaggagca gacacatcag 1620
aggttcactg gaattacaaa gagagaatgg tgacatttaa ggttcctcat gccaagagac 1680
aggatgtgac agtgctggga tctcaggaag gagccatgca ttctgccctc gctggagcca 1740

```
cagaagtgga ctccggtgat ggaaatcaca tgtttgcagg acatctcaag tgcaaagtcc    1800
gtatggagaa attgagaatc aagggaatgt catacacgat gtgttcagga agttctcaa    1860 ttgacaaaga gatggcagaa acacagcatg ggacaacagt ggtgaaagtc aagtatgaag    1920
gtgctggagc tccgtgtaaa gtccccatag agataagaga tgtgaacaag aaaaagtgg    1980 ttgggcgtat catctcatcc acccctttgg ctgagaatac caacagtgca accaacatag    2040
agttagaacc cccctttggg gacagctaca tagtgatagg tgttggaaac agtgcattaa    2100
cactccattg gttcaggaaa gggagttcca ttggcaagat gtttgagtcc acatacagag    2160
gtgcaaaacg aatggccatt ctaggtgaaa cagcttggga ttttggttcc gttggtggac    2220
tgttcacatc attgggaaag gctgtgcacc aggttttttgg aagtgtgtat acaaccatgt    2280
ttggaggagt ctcatggatg attagaatcc taattgggtt cctagtgttg tggattggca    2340
cgaactcaag gaacacttca atggctatga cgtgcatagc tgttggagga atcactctgt    2400
ttctgggctt cacagttcaa gcagacatgg gttgtgtggt gtcatggagt gggaaagaat    2460
tgaagtgtgg aagcggaatt tttgtggttg acaacgtgca cacttggaca gaacagtaca    2520
aatttcaacc ggagtcccca gcgagactag cgtctgcaat attgaatgcc acaaagatg    2580 gggtctgtgg aattagatca accacgaggc tggaaaatgt catgtggaag caaataacca    2640
acgagctaaa ttatgttctc tgggaaggag gacatgacct cactgtagtg ctggggatg    2700 tgaaggggt gttgaccaaa ggcaagagag cactcacacc cccagtgaat gatctgaaat    2760
attcatggaa gacatgggga aaagcaaaaa tcttcacccc agaagcaaga aatagcacat    2820
ttttaataga cggaccagac acctccgaat gccccaatga acgaagagca tggaactttc    2880
ttgaggtgga agactatgga tttggcatgt tcacgaccaa catatggatg aaattccgag    2940
aaggaagttc agaagtgtgt gaccacaggt taatgtcagc ggcaattaaa gatcagaaag    3000
ctgtgcatgc tgacatgggt tattggatag agagctcaaa aaaccagacc tggcagatag    3060
agaaagcatc tcttattgaa gtgaaaacat gtctgtggcc caagacccac acattgtgga    3120
gcaatggagt gctggaaagc cagatgctca ttccaaaatc atatgcgggc cctttttcac    3180
accacaatta ccgccagggc tatgccacgc aaaccgtggg cccatggcac ttaggcaaat    3240
tagagataga cttttgagaa tgccccggaa caacagtcgc aattcaggag gattgtgacc    3300
atagaggccc atctttgagg accaccactg catctggaaa actagtcacg caatggtgct    3360
gccgctcctg cacgatgcct cccttaaggt tcttgggaga agatgggtgc tggtatggga    3420
tggagattag gccccttgagt gaaaaagaag agaaacatggt caaatcacag gtaacggccg    3480
gacagggcac atcagaaact ttttctatgg gtctgttgtg cctgaccttg tttgtggaag    3540
aatgcttgag gagaagagtc actaggaaac acatgatatt ggttgtggtg atcactcttt    3600
gtgccatcat cctaggaggc ctcacatgga tggacttact acgagccctc atcatgttgg    3660
gggacactat gtctggtaga ataggaggac agatccacct agccatcatg gcagtgttca    3720
agatgtcacc aggatacgtg ctgggtgtgt ttttaaggaa actcacttca agagagacag    3780
cactaatggt aataggaatg gccatgacaa cggtgctttc aattccacat gaccttatgg    3840
aactcattga tggaatatca ctggggctaa ttttgctaaa aatagtgaca cattttgaca    3900
acacccaagt gggaaccttta gccctttcct tgaccttcat aagatcaaca atgccattgg    3960
tcatggcttg gaggaccatt atggctgtgt tgtttgtggt cacactcatt cctttgtgca    4020
ggacaagctg tcttcaaaaa cagtctcatt gggtagaaat aacagcactc atcctaggag    4080
```

```
cccaagctct gccagtgtac ctaatgactc ttatgaaagg agcctcaaga agatcttggc   4140
ctcttaacga gggcataatg gctgtgggtt tggttagtct cttaggaagc gctcttttaa   4200
agaatgatgt cccctttagct ggcccaatgg tggcaggagg cttacttctg gcggcttacg   4260
tgatgagtgg tagctcagca gatctgtcac tagagaaggc cgccaatgtg cagtgggatg   4320
aaatggcaga cataacaggc tcaagcccaa tcatagaagt gaagcaggat gaagatggct   4380 cttctctccat acgggacgtc gaggaaacca atatgataac ccttttggtg aaactggcac   4440
tgataacagt gtcaggtctc tacccttgg caattccagt cacaatgacc ttatggtaca   4500
tgtggcaagt gaaaacacaa agatcaggag ccctgtggga cgtcccctca cccgctgcca   4560
ctcaaaaagc cgcactgtct gaaggagtgt acaggatcat gcaaagaggg ttatttggga   4620
aaactcaggt tggagtaggg atacacatgg aaggtgtatt tcacacaatg tggcatgtaa   4680
caagaggatc agtgatctgc catgagactg ggagattgga gccatcttgg gctgacgtca   4740
ggaatgacat gatatcatac ggtgggggat ggagacttgg agacaaatgg gacaaagaag   4800
aagatgttca ggtcctcgcc atagaaccag gaaaaaatcc taaacatgtc caaacgaaac   4860
ccggcctttt caagacccta actggagaaa ttggagcagt aacattagat ttcaaacccg   4920
gaacgtctgg ttctcccatc atcaacagga aggaaaagt catcggactc tatggaaatg   4980
gagtagttac caaatcaggt gattacgtca gtgccataac gcaagccgaa agaattggag   5040
agccagatta tgaagtggat gaggacattt ttcgaaagaa aagattaact ataatggact   5100
tacaccccgg agctggaaag acaaaaagaa ttcttccatc aatagtgaga gaagccttaa   5160
aaaggaggct gcgaaccttg attttggctc ccacgagagt ggtggcggcc gagatggaag   5220
aggccctacg tggactgcca atccgttatc agaccccagc tgtgaaatca gaacacacag   5280
gaagagagat tgtagacctc atgtgtcatg caaccttcac aacaagactt ttgtcatcaa   5340
ccagagttcc aaattacaac ctcatagtga tggatgaagc acatttcacc gatccttcta   5400
gtgtcgcggc tagaggatac atctcgacca gggtggaaat gggagaggca gcagccatct   5460
tcatgaccgc aaccccctccc ggagcgacag atcccttttcc ccagagcaac agcccaatag   5520
aagacatcga gagggaaatt ccggaaaggt catggaacac agggttcgac tggataacag   5580
actaccaagg gaaaactgtg tggtttgttc ccagcataaa agctggaaat gacattgcaa   5640
attgtttgag aaagtcggga aagaaagtta tccagttgag taggaaaaacc tttgatacag   5700 agtatccaaa aacgaaactc acggactggg atttttgtggt cactacagac atatctgaaa   5760
tgggggccaa ttttagagct gggagagtga tagaccctag gagatgcctc aagccagtta   5820
tcctaacaga tgggccagag agagtcattt tagcaggtcc tattccagtg actccagcaa   5880
gcgctgctca gagaagaggg cgaataggaa ggaacccagc acaagaagac gaccaatacg   5940
ttttctccgg agacccacta aaaaatgatg aagatcatgc ccactggaca gaagcaaaga   6000
tgctgcttga caatatctac acccccagaag ggatcattcc aacattgttt ggtccggaaa   6060
gggaaaaaac ccaagccatt gatggagagt ttcgcctcag aggggaacaa aggaagactt   6120
ttgtggaatt aatgaggaga ggagaccttc cggtgtggct gagctataag gtagcttctg   6180
ctggcatttc ttacaaagat cgggaatggt gcttcacagg ggaaaggaat aaccaaattt   6240
tagaagaaaa catggaggtt gaaatttgga ctagagaggg agaaaagaaa aagctaaggc   6300
caagatggtt agatgcacgt gtatacgctg accccatggc tttgaaggat tttaaggagt   6360
ttgctagtgg aaggaagagc ataactctcg acatcctaac agagattgcc agtttgccaa   6420
cttacctttc ctctagggcc aagctcgccc ttgataacat agtcatgctc cacacaacag   6480
```

```
aaagaggagg gagggcctac caacacgccc tgaacgaact cccggagtca ctggaaacac   6540
ttatgcttgt agctttacta ggtgctatga cagcaggtat cttcctgttt ttcatgcaag   6600
ggaaaggaat agggaaattg tcaatggggtt tgataaccat tgcggtggct agtggcttgt   6660
tctgggtagc agaaattcaa ccccagtgga tagcggcctc aatcatacta gagttttttc   6720
tcatggtact gttgataccg gaaccagaaa acaaaggac cccacaagac aatcaattga    6780
tctacgtcat attgaccatt ctcaccatta ttggtctcat agcagccaac gagatggggc   6840
tgattgaaaa aacaaaaacg gattttgggt tttaccaggt aaaaacagaa accaccatcc   6900
tcgatgtgga cttgagacca gcttcagcat ggacgctcta tgcagtagcc accacawttc   6960
tgactcccat gctgagacac accatagaaa acacgtcggc caacctatct ctagcagcca   7020
ttgccaacca ggcggccgtc ctaatggggc ttggaaaagg atggccgctc cacagaatgg   7080
acctcggtgt gccgctgtta gcaatgggat gctattctca agtgaaccca caaactttga   7140
cagcatcctt agtcatgctt tcagtccatt atgcaataat aggtccagga ttgcaggcaa   7200
aagccacaag agaggcccag aaaaggacag ctgctgggat catgaaaaac cccacggtgg   7260
acgggataac agtaatagat ctagaaccaa tatcctatga cccaaaattt gaaaagcaat   7320
tagggcaggt catgctactc gtcttgtgtg ctggacaact actcttgatg agaacaacat   7380
gggctttctg tgaagtcttg actttggcca caggaccaat cttgaccttg tgggagggca   7440
acccgggaag gttttggaac acgaccatag ccgtatccac cgccaacatt ttcaggggaa   7500
gttacctggc gggagctgga ctggcttttt cactcataaa gaatgyacaa accccctagga   7560 ggggaactgg gaccacagga gagacactgg gagagaagtg aagagacag ctaaactcat     7620 takacagaaa agagtttgaa gagtataaaa gaagtggaat actagaagtg gacaggactg    7680
aagccaagtc tgccctgaaa gatgggtcta aaatcaagca tgcagtatct agagggtcca   7740
gtaagattag atggattgtt gagagaggga tggtaaagcc aaaagggaaa gttgtagatc   7800
ttggctgtgg gagaggagga tggtcttatt acatggcgac gctcaagaac gtgactgaag   7860
tgaaagggta tacaaaagga ggtccaggac atgaagaacc gattcccatg gctacttatg   7920
gctggaattt ggtcaaactc cattcagggg ttgacgtgtt ctacaaaccc acagagcaag   7980 tggacacccct gctctgtgat attggggagt catcttctaa tccaacaata gaggaaggaa   8040
gaacattaag agttttgaag atggtggagc catggctctc ttcaaaacct gaattctgca   8100
tcaaagtcct taacccctac atgccaacag tcatagaaga gctggagaaa ctgcagagaa   8160
aacatggtgg gaaccttgtc agatgccgc tgtccaggac ctccacccat gagatgtatt    8220
gggtgtcagg agcgtcggga acattgtga gctctgtgaa cacaacatca agatgttgt      8280 tgaacaggtt cacaacaagg cataggaaac ccacttatga aaggacgta gatcttgggg    8340 caggaacgag aagtgtctcc actgaaacag aaaaaccaga catgacaatt attgggagaa   8400
ggcttcagcg attgcaagag gagcacaaag aaacctggca ttatgatcag gaaaacccat   8460
acagaacctg gcgtatcat ggaagctatg aagctccttc gacaggctct gcatcctcca     8520
tggtgaacgg ggtagtaaaa ctgctaacaa aaccttggga tgtggttcca atggtgaccc   8580
agttagccat gacagacaca accccttttg gcaacaaag agtgttcaaa gagaaggtgg    8640
ataccagaac accacaacca aaacccggta cacgaatggt tatgaccacg acagccaatt   8700
ggctgtgggc cctccttggg aagaagaaaa atcccagact gtgcacaagg gaagagttca   8760
tctcaaaagt tagatcaaac gcagccatag gcgcagtctt tcaggaagaa cagggatgga   8820
```

```
catcagccag tgaagctgtg aatgacagcc ggttttggga actggttgac aaagaaaggg    8880
ccctacacca ggaagggaaa tgtgaatcgt gtgtctacaa catgatggga aaacgtgaga    8940
aaaagttagg agagtttggc agagccaagg gaagccgagc aatctggtac atgtggctgg    9000
gagcgcggtt tctggaattt gaagccctgg gttttttgaa tgaagatcac tggtttggca    9060
gagaaaattc atggagtgga gtggaagggg aaggtctgca cagattggga tatatcctgg    9120
aggagataga caagaaggat ggagacctaa tgtatgctga tgacacagca ggctgggaca    9180
caagaatcac tgaggatgac cttcaaaatg aagaactgat cacggaacag atggcccccc    9240
accacaagat cctagccaaa gccattttca aactaaccta tcaaaacaaa gtggtgaaag    9300
tcctcagacc cacaccgaga ggagcggtga tggatatcat atccaggaaa gaccaaagag    9360
gtagtggaca agttggaaca tatggtttga acacattcac caacatggaa gttcaactca    9420
tccgccaaat ggaagctgaa ggagtcatca cacaagatga catgcagaac ccaaaagggt    9480
tgaaagaaag agttgagaaa tggctgaaag agtgtggtgt cgacaggtta aagaggatgg    9540
caatcagtgg agacgattgc gtggtgaagc ccctggatga gaggtttggc acttccctcc    9600
tcttcttgaa cgacatggga aaggtgagga agacattcc gcagtgggaa ccatctaagg    9660
gatggaaaaa ctggcaagag gttcctttt gctcccacca ctttcacaag atcttcatga    9720
aggatggccg ctcactagtt gttccatgta gaaaccagga tgaactgata gggagagcca    9780
gaatctcgca gggggctgga tggagcttaa gagaaacagc ctgcctgggc aaagcttacg    9840
cccagatgtg gtcgctcatg tacttccaca gaagggatct gcgtttagcc tccatggcca    9900
tatgctcagc agttccaacg gaatggtttc caacaagcag aacaacatgg tcaatccacg    9960
ctcatcatca gtggatgacc actgaagata tgctcaaagt gtggaacaga gtgtggatag   10020
aagcaaccc taatatgact gacaagactc cagtccattc gtgggaagat ataccttacc   10080
tagggaaaag agaggatttg tggtgtggat ccctgattgg acttttcttcc agagccacct   10140
gggcgaagaa cattcacacg gccataaccc aggtcagaaa cctgatcgga aaagaggaat   10200
acgtggatta catgccagta atgaaagat acagcgctcc ttcagagagt gaaggagttc   10260
tgtaattacc aacaacaaac accaaaggct attgaagtca ggccacttgt gccacggctt   10320
gagcaaaccg tgctgcctgt agctccgcca ataatgggag gcgtgaaatc cctagggagg   10380
ccatgcgcca cggaagctgt acgcgtggca tattggacta gcggttagag gagacccctc   10440
ccatcactga caaaacgcag caaaagggggg cccgaagcca ggaggaagct gtactcctgg   10500
tggaaggact agaggttaga ggagaccccc caacacaaa aacagcatat tgacgctggg   10560
aaagaccaga gatcctgctg tctctgcaac atcaatccag gcacagagcg aagcaagatg   10620
gattggtgtt gttgatccaa caggttct                                     10648
```